(12) United States Patent
Bremberg et al.

(10) Patent No.: US 7,173,035 B2
(45) Date of Patent: Feb. 6, 2007

(54) ARYLSULFONAMIDE COMPOUNDS

(75) Inventors: Ulf Bremberg, Lipplands Väsby (SE); Patrizia Caldirola, Uppsala (SE); Annika J. Jensen, Uppsala (SE); Gary Johansson, Uppsala (SE); Lori Sutin, Knivasta (SE); Andrew Mott, Knivsta (SE); Jan Tejbrant, Enskede (SE)

(73) Assignee: Biovitrum AB (SE)

( * ) Notice: Subject to any disclaimer, the term of this patent is extended or adjusted under 35 U.S.C. 154(b) by 396 days.

(21) Appl. No.: 10/143,335

(22) Filed: May 10, 2002

(65) Prior Publication Data

US 2003/0149019 A1    Aug. 7, 2003

Related U.S. Application Data

(60) Provisional application No. 60/294,132, filed on May 29, 2001, provisional application No. 60/294,102, filed on May 29, 2001.

(30) Foreign Application Priority Data

| May 11, 2001 | (SE) | ..................... 0101659 |
| May 11, 2001 | (SE) | ..................... 0101660 |
| Jun. 5, 2001 | (SE) | ..................... 0101958 |

(51) Int. Cl.
*A61P 25/00* (2006.01)
*A61K 31/497* (2006.01)
*A61K 31/4965* (2006.01)
*C07D 401/00* (2006.01)
*C07D 241/00* (2006.01)

(52) U.S. Cl. ..................... 514/253.06; 514/254.04; 514/255.03; 544/363; 544/367; 544/395

(58) Field of Classification Search ........... 514/253.06, 514/254.04, 255.03; 544/363, 367, 395
See application file for complete search history.

(56) References Cited

U.S. PATENT DOCUMENTS

| 3,876,632 | A | * | 4/1975 | Sturm et al. ................ 544/357 |
| 6,342,512 | B1 | * | 1/2002 | Kirsch et al. ............... 514/326 |
| 6,399,617 | B1 | * | 6/2002 | Caldirola et al. ...... 514/253.05 |
| 6,632,838 | B1 | * | 10/2003 | Kirsch et al. ............... 514/602 |
| 2003/0149020 | A1 | | 8/2003 | Bremberg et al. ..... 514/211.01 |

FOREIGN PATENT DOCUMENTS

| DE | 24 59 394 A1 * | 6/1976 |
| EP | 0331232 A2 | 9/1989 |
| EP | 0815861 A1 | 1/1998 |
| FR | 2033597 A5 | 12/1970 |
| WO | WO 9715555 A2 | 5/1997 |
| WO | WO 9806697 A1 | 2/1998 |
| WO | WO 9827081 A1 | 6/1998 |
| WO | WO 9902502 A2 | 1/1999 |
| WO | WO 9937623 A2 | 7/1999 |
| WO | WO 9938845 A1 | 8/1999 |
| WO | WO 9942465 A2 | 8/1999 |
| WO | WO 0005225 A1 | 2/2000 |
| WO | WO 0012623 A2 | 3/2000 |
| WO | WO 00122073 A1 | 3/2000 |
| WO | WO 2001/16094 A1 * | 3/2001 |

OTHER PUBLICATIONS

Baxter et al., Amination of NN'-Dibenzenesulphonyl-1,4-benzoquinone Di-imines: Photochemical Formation of Benzimidazoles, Journal of the Chemical Society, Section C, 1968, vol. 14, pp. 1747-1752.*
Jones et al., The Medical Benefit of 5-HT Research, Pharmacology, Biochemistry and Behavior, vol. 71, pp. 555-568, 2002.*
Hirst et al., Characterization of [1251]-SB-258585 Binding to Human Recombinant and Native 5-HT6 Receptors in Rat, Pig and Human Brain Tissue, British Journal of Pharmacology, vol. 130, No. 7, pp. 1597-1605, Aug. 2000.*
Liao et al., New Selective and Potent 5-HT1B/1D Antagonists: Chemistry and Pharmacological Evaluation of N-Piperazinylphenyl Biphenylcarboxamides and Biphenylsulfonamides, Journal of Medicinal Chemistry, vol. 43, No. 3, pp. 517-525 Feb. 10, 2000.*
Bromidge et al., "5-Chloro-N-(4-methoxy-3-piperazin-1-yl-phenyl)-3-methyl-2-benzothiophenesulfonamide . . . ", 1999, J.Med. chem., vol. 42;202-205.
Issac et al., "6-Bicyclopiperazinyl1-1-arylsulfonylindoles . . . ", 2000, Bioorganic & Medicinal Chemistry Letters, vol. 10; 1719-1721, 2000.

(Continued)

*Primary Examiner*—Brenda Coleman
(74) *Attorney, Agent, or Firm*—Fish & Richardson P.C.

(57) ABSTRACT

The present invention relates to substituted bis-arylsulfonamide and arylsulfonamide compounds of the general formula (I) or the formula (II), which compounds are potentially useful for the prophylaxis and treatment of medical conditions relating to obesity, type II diabetes and/or disorders of the central nervous system.

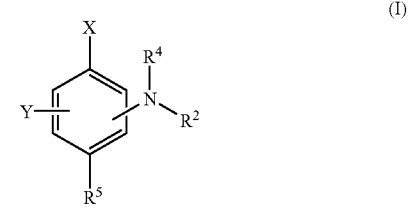

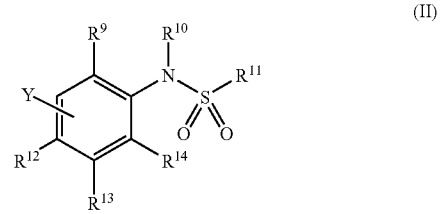

31 Claims, No Drawings

OTHER PUBLICATIONS

Bentley et al., "Effect of the 5-HT$_6$ Antagonist, Ro 04-6790 on Food Consumption in Rats Trained to a Fixed Feeding Regime", *British Journal of Pharmacology*, 126 (1999): suppl.

Bourson et al., "Involvement of HT$_6$ Receptors in Nigro-Striatal Function in Rodents", *British Journal of Pharmacology*, 125:1562-1566 (1998).

Dawson et al., "Selective Enhancement of Glutamatergic Neurotransmission in the Frontal Cortex and Dorsal Hippocampus by antagonism of the 5-HT$_6$ Receptor", *Monitoring Molecules in Neuroscience*, pp. 318-319, Jun. 16-19, 2001.

Dawson et al., "The 5-HT$_6$ Receptor Antagonist SB-271046 Selectively Enhances Excitatory Neurotransmission in the Rat Frontal Cortex and Hippocampus", *Neuropsychopharmacology*, 25(5)P:662-668 (2001).

Dawson et al., "Potentiation of Amphetamine-Induced Changes in Dopamine and 5-HT by a 5-HT$_6$ Receptor Antagonist", *Brain Research Bulletin*, 59(6):513-521 (2003).

Foley et al., "The 5-HT$_6$ReceptorAntagonist SB-271045 Reverses Scopolamine-Disrupted Consolidation of a Passive Avoidance Task and Ameliorates Spatial Task Deficits in Aged Rats", *Neuropsychopharmacology*, 29:93-100 (2004).

Frantz et al., "5-HT$_6$Receptor Antagonism Potentiates the Behavioral and Neurochemical Effects of Amphetamine but not Cocaine", *Neuropharmacology*, 42:170-180 (2002).

Lacroix et al., "5-HT$_6$ Receptor Antagonist SB-271046 Enhances Extracellular Levels of Monoamines in the Rat Medial Prefrontal Cortex", *Synapse*, 51:158-164 (2004).

Matsumoto et al., "Characterization of Endogenous Serotonin-Mediated Regulation of Dopamine Release in Rat Prefrontal Cortex", *European Journal of Pharmacology*, 383:39-48 (1999).

Meneses, Role of 5-HT$_6$Receptors in Memory Formation, *Drug News & Perspectives*, 14(7):396-400 (2001).

Meneses, "Effects of the 5-HT$_6$Receptor Antagonist Ro 04-6790 on Learning Consolidation", *Behavioural Brain Research*, 118:107-110 (2001).

Minabe et al., "Effect of the Acute and Chronic Administration of the Selective 5-HT$_6$Receptor Antagonist SB-271046 on the Activity of Midbrain Dopamine Neurons in Rats: In Vivo Electrophysiological Study", *Synapse*, 52:20-28 (2004).

Otano et al., "Anxiogenic-Like Effects and Reduced Stereological Counting of Immunolabelled 5-Hydroxytryptamine$_6$Receptos in Rat Nucleus Accumbens by Antisense Oligonucleotides", *Neuroscience*, 92(3):1001-1009 (1999).

Riemer et al., "Influence of the 5-HT$_6$Receptor on Acetylcholine Release in the Cortex: Pharmacological Characterization of 4-(2-Bromo-6-pyrrolidine-1-ylpyridine-4-sulfonyl)phenylamine, a Potent and Selective 5-HT$_6$Receptor Antagonist", *J. Med. Chem.*, 46:1273-1276 (2003).

Roberts et al., "Distribution of 5-HT$_6$Receptors in Rat Brain: An Autoradiographic Binding Study Using the Radiolabelled 5-HT$_6$Receptor Antagonist [$^{125}$I]SB-258585", *Brain Research*, 934:49-57 (2002).

Rogers et al., "5-HT$_6$Receptor Antagonists Enhance Retention of a Water Maze Task in the Rat", *Psychopharmacology*, 158:114-119 (2001).

Shirazi-Southall et al., "Effects of Typical and Atypical Antipsychotics and Receptor Selective Compounds on Acetylcholine Efflux in the Hippocampus of the Rat", *Neuropsychopharmacology*, 26(5):583-594 (2002).

Sleight et al., *Brit. J. Pharmacol.*, (1998) 124, 556-562.

Tsai et al., "Association Analysis of the 5-HT$_6$Receptor Polymorphism C267T in Alzheimer's Disease", *Neuroscience Letters*, 276:138-139 (1999).

Woolley et al., "A Role for 5-HT$_6$Receptors in Retention of Spatial Learning in the Morris Water Maze", *Neuropharmacology*, 41:210-219 (2001).

Woolley et al., "Reversal of a Cholinergic-Induced Deficit in a Rodent Model of Recognition Memory by the Selective 5-HT$_6$Receptor Antagonist, Ro 04-6790", *Psychopharmacology*, 170:358-367 (2003).

Woolley et al., "5-HT$_6$Receptors", *Current Drug Targets—CNS & Neurological Disorders*, 3:59-79 (2004).

\* cited by examiner

ARYLSULFONAMIDE COMPOUNDS

RELATED APPLICATIONS

This application claims the benefit of U.S. provisional application No. 60/294,102, filed on May 29, 2001 and U.S. provisional application No. 60/294,132, filed on May 29, 2001, the contents of which are incorporated herein by reference.

TECHNICAL FIELD

The present invention relates to substituted bis-arylsulfonamide and arylsulfonamide compounds, to pharmaceutical compositions comprising these compounds, and to the use of the compounds for the prophylaxis and treatment of medical conditions relating to obesity, type II diabetes and/or disorders of the central nervous system.

BACKGROUND

Obesity is a condition characterized by an increase in body fat content resulting in excess body weight above accepted norms. Obesity is the most important nutritional disorder in the western world and represents a major health problem in all industrialized countries. This disorder leads to increased mortality due to increased incidences of diseases such as cardiovascular disease, digestive disease, respiratory disease, cancer and type II diabetes. Searching for compounds, which reduce body weight has been going on for many decades. One line of research has been activation of serotonergic systems, either by direct activation of serotonin receptor subtypes or by inhibiting serotonin reuptake. The exact receptor subtype profile required is however not known.

Serotonin (5-hydroxytryptamine or 5-HT), a key transmitter of the peripheral and central nervous system, modulates a wide range of physiological and pathological functions, including anxiety, sleep regulation, aggression, feeding and depression. Multiple serotonin receptor subtypes have been identified and cloned. One of these, the 5-HT$_6$ receptor, was cloned by several groups in 1993 (Ruat, M. et al. (1993) Biochem. Biophys. Res. Commun. 193: 268–276; Sebben, M. et al. (1994) NeuroReport 5: 2553–2557). This receptor is positively coupled to adenylyl cyclase and displays affinity for antidepressants such as clozapine. Recently, the effect of 5-HT$_6$ antagonist and 5-HT$_6$ antisense oligonucleotides to reduce food intake in rats has been reported (Bentley, J. C. et al. (1999) Br J Pharmac. Suppl. 126, P66; Bentley, J. C. et al. (1997) J. Psychopharmacol. Suppl. A64, 255).

Compounds with enhanced affinity and selectivity for the 5-HT$_6$ receptor have been identified, e.g. in WO 00/34242 and by Isaac, M. et al. (2000) 6-Bicyclopiperazinyl-1-arylsulfonylindoles and 6-Bicyclopiperidinyl-1-arylsulfonylindoles derivatives as novel, potent and selective 5-HT$_6$ receptor antagonists. Bioorganic & Medicinal Chemistry Letters 10: 1719–1721.

DISCLOSURE OF THE INVENTION

It has surprisingly been found that the compounds of formula (I) and (II) show affinity for the 5-HT$_6$ receptor as antagonists at a low nanomolar range. Compounds according to the invention and their pharmaceutically acceptable salts have 5-HT$_6$ receptor antagonist activity and are believed to be of potential use in the treatment or prophylaxis of obesity and type II diabetes, as well as in the treatment or prophylaxis of disorders of the central nervous system such as anxiety, depression, panic attacks, memory disorders, sleep disorders, binge disorders, migraine, anorexia, bulimia, obsessive compulsive disorders, psychoses, Alzheimer's disease, Parkinson's disease, Huntington's chorea and/or schizophrenia, drug abuse, Attention Deficit Hyperactive Disorders (ADHD).

Definitions

Unless otherwise stated or indicated, the following definitions shall apply throughout the specification and the appended claims:

The term "$C_{1-6}$ alkyl" denotes a straight or branched alkyl group having from 1 to 6 carbon atoms. Examples of said lower alkyl include methyl, ethyl, n-propyl, iso-propyl, n-butyl, iso-butyl, sec-butyl, t-butyl and straight- and branched-chain pentyl and hexyl.

The term "$C_{1-6}$ alkoxy" denotes a straight or branched alkoxy group having from 1 to 6 carbon atoms. Examples of said lower alkoxy include methoxy, ethoxy, n-propoxy, iso-propoxy, n-butoxy, iso-butoxy, sec-butoxy, t-butoxy and straight- and branched-chain pentoxy and hexoxy.

The term "halogen" shall mean fluorine, chlorine, bromine or iodine.

The terms "$C_{4-6}$ cycloalkyl" and "$C_{3-7}$ cycloalkyl" denote a cyclic alkyl group having a ring size from $C_4$ to $C_6$ or from $C_3$ to $C_7$, respectively. Examples of said cycloalkyl include cyclopropyl, cyclobutyl, cyclopentyl, cyclohexyl, methylcyclohexyl and cycloheptyl.

Compounds of Formula I

In a first aspect, this invention provides a compound of the general formula (I)

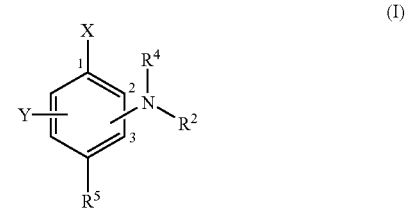

(I)

or a pharmaceutically acceptable salt thereof, wherein
X is

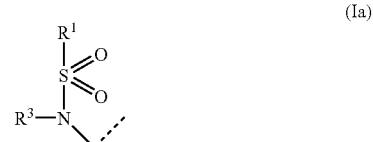

(Ia)

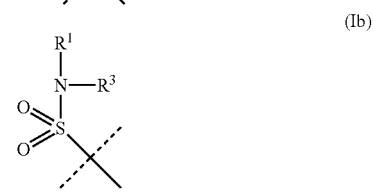

(Ib)

$R^1$ and $R^3$ are independently
(a) H
(b) $C_{1-6}$ alkyl,
(c) $C_{1-6}$ alkoxy,
(d) straight or branched $C_{1-6}$ hydroxyalkyl,
(e) straight or branched $C_{1-6}$ alkylhalides; or
(f) a group Ar;
Ar is
(a) phenyl,
(b) 1-naphthyl,
(c) 2-naphthyl,
(d) benzyl,
(e) cinnamoyl,
(f) a 5 to 7-membered, partially or completely saturated, heterocyclic ring containing 1 to 4 heteroatoms, selected from oxygen, nitrogen and sulfur, or
(g) a bicyclic ring system consisting of two heterocyclic rings as defined under (f), or a bicyclic ring system consisting of one benzene ring and one heterocyclic ring as defined under (f);
alternatively, $R^1$ and $R^3$ are linked to form a group $(CH_2)_2O$, $(CH_2)_4O$, or $(CH_2)_{3-5}$ i (Ib);
optionally, the group Ar is substituted with
(a) Y, or
(b) a 5 to 7-membered, partially or completely saturated, heterocyclic ring each containing 1 to 4 heteroatoms selected from oxygen, nitrogen or sulfur;
Y is
(a) H,
(b) halogen,
(c) $C_{1-6}$ alkyl,
(d) $CF_3$,
(e) hydroxy,
(f) $C_{1-6}$ alkoxy,
(g) $C_{1-4}$ alkenyl;
(h) phenyl;
(i) phenoxy,
(j) benzyloxy,
(k) benzoyl,
(l) $OCF_3$,
(m) CN,
(n) straight or branched $C_{1-6}$ hydroxyalkyl,
(o) straight or branched $C_{1-6}$ alkylhalides,
(p) $NH_2$,
(q) $NHR^6$,
(r) $NR^6R^7$,
(s) $NO_2$,
(t) —$CONR^6R^7$,
(u) $NHSO_2R^6$,
(v) $NR^6COR^7$,
(x) $SO_2NR^6R^7$,
(z) —C(=O)$R^6$,
(aa) —$CO_2R^6$, or
(ab) $S(O)_nR^6$; wherein n is 0, 1, 2 or 3;
$R^2$ and $R^4$ are independently:
(a) —$SO_2R^1$,
(b) H,
(c) $C_{1-6}$ alkyl,
(d) $C_1$-$C_3$ alkenyl,
(e) $C_1$-$C_3$ alkylaryl,
(f) Ar as defined above for $R^1$,
(g) —C(=O)$R^6$,
(h) —C(O)$NR^6R^7$,
(i) —C(S)$NR^6R^7$,
(j) —$CO_2R^6$;
(k) —C(S)$R^6$;
(l) straight or branched $C_{1-6}$ hydroxyalkyl, or
(m) straight or branched $C_{1-6}$ alkylhalides;

alternatively, $R^2$ and $R^4$ are linked to form a group $(CH_2)_2O$, $(CH_2)_4O$, or $(CH_2)_{3-5}$ in formula (Ia);
$R^5$ is selected from the group consisting of the following chemical groups:

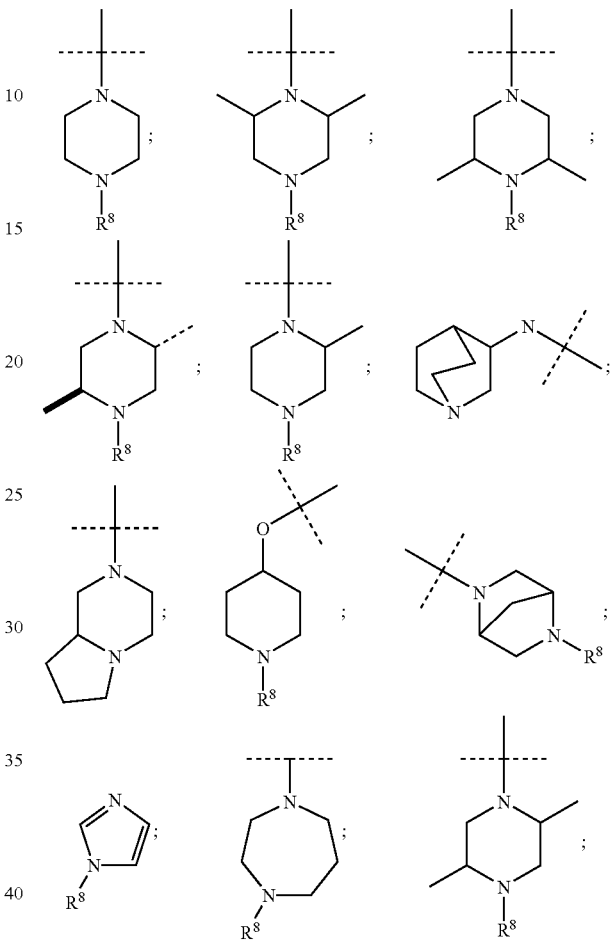

$R^6$ and $R^7$ are independently
(a) H,
(b) $C_{1-6}$ alkyl,
(c) $C_{3-7}$ cycloalkyl, or
(d) Ar, as defined above in $R^1$;
alternatively, $R^6$ and $R^7$ are linked to form a group $(CH_2)_2O$, $(CH_2)_4O$ or $(CH_2)_{3-5}$;
$R^8$ is
(a) H, or
(b) $C_{1-6}$ alkyl.
Preferred compounds of the general formula (I) are those wherein:
X is

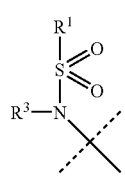

(Ia)

-continued

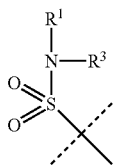
(Ib)

R¹ is
(e) a group Ar; or
(f) $C_{1-6}$ alkyl
Ar is
(a) phenyl,
(b) 1-naphthyl,
(c) 2-naphthyl, or
(f) a 5 to 7-membered, partially or completely saturated, heterocyclic ring containing 1 to 4 heteroatoms, selected from oxygen, nitrogen and sulfur;
the group Ar is substituted with Y, wherein Y is
(a) H,
(b) halogen,
(c) $C_{1-6}$ alkyl,
(d) $CF_3$,
(f) $C_{1-6}$ alkoxy,
(g) $C_{1-4}$ alkenyl;
(h) phenyl;
(l) $OCF_3$, or
(n) straight or branched $C_{1-6}$ hydroxyalkyl;
the group

is attached to the phenyl ring in 2-position or in 3-position;
R² and R⁴ are indipendently
(a) H
(b) C1-3 alkyl, in particular methyl or ethyl
(c) —$SO_2R^1$; or
(d) are linked to form a group $(CH_2)_4O$
R⁵ is selected from the group consisting of the following chemical groups:

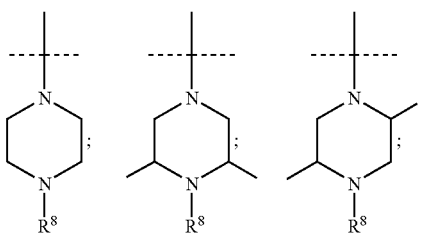

wherein R⁸ is
(a) H, or
(b) $C_{1-6}$ alkyl, in particular methyl.
R⁶ and R⁷ are independently
(a) H,
(b) $C_{1-6}$ alkyl,
(c) $C_{3-7}$ cycloalkyl, or
(d) Ar.

N-[2-[ethyl(phenylsulfonyl)amino]-4-(4-methyl-1-piperazinyl)phenyl]benzenesulfonamide hydrochloride
3-fluoro-N-[2-{[(3-fluorophenyl)sulfonyl]amino}-4-(4-methyl-1-piperazinyl)phenyl]benzenesulfonamide hydrochloride
N-{4-(4-methyl-1-piperazinyl)-2-[(8-quinolinylsulfonyl)amino]phenyl}-8-quinolinesulfonamide hydrochloride
4-methyl-N-{4-(4-methyl-1-piperazinyl)-2-[(methylsulfonyl)amino]phenyl}benzenesulfonamide hydrochloride
N-{4-(1-piperazinyl)-2-[(phenylsulfonyl)amino]phenyl}-1-naphthalenesulfonamide hydrochloride
N-[2-[(phenylsulfonyl)amino]-4-(1-piperazinyl)phenyl]-8-quinolinesulfonamide hydrochloride
2-methyl-N-[2-[(phenylsulfonyl)amino]-4-(1-piperazinyl)phenyl]benzenesulfonamide hydrochloride
4-butoxy-N-[2-[(phenylsulfonyl)amino]-4-(1-piperazinyl)phenyl]benzenesulfonamide hydrochloride
5-fluoro-2-methyl-N-[2-[(phenylsulfonyl)amino]-4-(1-piperazinyl)phenyl]benzenesulfonamide hydrochloride
2-methoxy-4-methyl-N-[2-[(phenylsulfonyl)amino]-4-(1-piperazinyl)phenyl]benzenesulfonamide hydrochloride
N-{4-(1,4-diazepan-1-yl)-2-[(phenylsulfonyl)amino]phenyl}benzenesulfonamide hydrochloride
N-{5-(1,4-diazepan-1-yl)-2-[(phenylsulfonyl)amino]phenyl}-N-ethylbenzenesulfonamide hydrochloride
N-{4-(1,4-diazepan-1-yl)-2-[(phenylsulfonyl)amino]phenyl}-2-naphthalenesulfonamide hydrochloride
N-{4-(1,4-diazepan-1-yl)-2-[methyl(phenylsulfonyl)amino]phenyl}benzenesulfonamide hydrochloride
N-{4-(1,4-diazepan-1-yl)-2-[(methylsulfonyl)amino]phenyl}-1-naphthalenesulfonamide hydrochloride
N-{4-(1,4-diazepan-1-yl)-2-[(methylsulfonyl)amino]phenyl}-2-naphthalenesulfonamide hydrochloride
N-{4-(1,4-diazepan-1-yl)-2-[methyl(methylsulfonyl)amino]phenyl}-1-naphthalenesulfonamide hydrochloride
N-{4-(1,4-diazepan-1-yl)-2-[(phenylsulfonyl)amino]phenyl}-8-quinolinesulfonamide hydrochloride
N-{4-(1,4-diazepan-1-yl)-2-[(phenylsulfonyl)amino]phenyl}-2,4,6-trimethylbenzenesulfonamide hydrochloride
N-{4-(1,4-diazepan-1-yl)-2-[(phenylsulfonyl)amino]phenyl}-4-methylbenzenesulfonamide hydrochloride
N-{4-(1,4-diazepan-1-yl)-2-[(phenylsulfonyl)amino]phenyl}-2-methylbenzenesulfonamide hydrochloride
N-{4-(1,4-diazepan-1-yl)-2-[(phenylsulfonyl)amino]phenyl}-5-fluoro-2-methylbenzenesulfonamide hydrochloride
N-{5-(1,4-diazepan-1-yl)-2-[methyl(phenylsulfonyl)amino]phenyl}-4-methylbenzenesulfonamide hydrochloride
3-amino-4-(1,4-diazepan-1-yl)-N-(2-methoxyphenyl)benzenesulfonamide hydrochloride
3-amino-N-(3-chlorophenyl)-4-(1,4-diazepan-1-yl)benzenesulfonamide hydrochloride
3-amino-N-(2-chlorophenyl)-4-(1,4-diazepan-1-yl)benzenesulfonamide hydrochloride
3-amino-4-(4-methyl-1,4-diazepan-1-yl)-N-phenylbenzenesulfonamide hydrochloride
3-amino-N-(2-methoxyphenyl)-4-(1-piperazinyl)benzenesulfonamide hydrochloride
2-[1,4]Diazepan-1-yl-5-(3,4-dihydro-1H-isoquinoline-2-sulfonyl)-aniline dihydrochloride hydrochloride
3-Amino-2-chloro-N-naphthalen-1-yl-4-piperazin-1-yl-benzenesulfonamide, hydrochloride hydrochloride

TABLE I

Compounds of the formula I wherein $R^2$ is $-SO_2-R^{1'}$

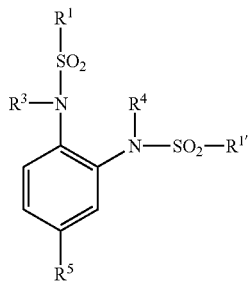

| Name | $R^1$ | $R^{1'}$ | $R^3$ | $R^4$ | $R^5$ |
|---|---|---|---|---|---|
| 1 N-[2-{ethyl[(3-fluorophenyl)sulfonyl]amino}-4-(4-methyl-1-piperazinyl)phenyl]-3-fluorobenzenesulfonamide | 3-fluorophenyl | 3-fluorophenyl | H | Et | 4-methyl-1-piperazinyl |
| 2 N-[2-[ethyl(phenylsulfonyl)amino]-4-(4-methyl-1-piperazinyl)phenyl]benzenesulfonamide | phenyl | phenyl | H | Et | 4-methyl-1-piperazinyl |
| 3 3-fluoro-N-[2-{[(3-fluorophenyl)sulfonyl]amino}-4-(4-methyl-1-piperazinyl)phenyl]benzenesulfonamide | 3-fluorophenyl | 3-fluorophenyl | H | H | 4-methyl-1-piperazinyl |
| 4 N-{4-(4-methyl-1-piperazinyl)-2-[(8-quinolinylsulfonyl)amino]phenyl}-8-quinolinesulfonamide hydrochloride | 8-quinolinyl | 8-quinolinyl | H | H | 4-methyl-1-piperazinyl |
| 5 N-[2-chloro-4-({4-(4-methyl-1-piperazinyl)-2-[(phenylsulfonyl)amino]anilino}sulfonyl)-phenyl]acetamide | 4-acetamido-3-chlorophenyl | phenyl | H | H | 4-methyl-1-piperazinyl |
| 6 3,4-dimethoxy-N-{4-(4-methyl-1-piperazinyl)-2-[(phenylsulfonyl)amino]phenyl}benzenesulfonamide | 3,4-dimethoxyphenyl | phenyl | H | H | 4-methyl-1-piperazinyl |

TABLE I-continued

Compounds of the formula I wherein R² is —SO₂—R¹'

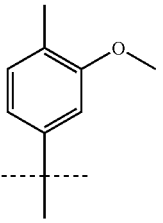

| Name | R¹ | R¹' | R³ | R⁴ | R⁵ |
|---|---|---|---|---|---|
| 7 3-methoxy-4-methyl-N-{4-(4-methyl-1-piperazinyl)-2-[(phenylsulfonyl)amino]phenyl}benzenesulfonamide | 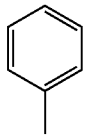 | 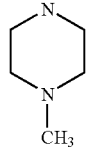 | H | H | 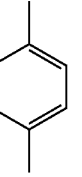 |
| 8 4-methyl-N-{4-(4-methyl-1-piperazinyl)-2-[(methylsulfonyl)amino]phenyl}benzenesulfonamide | 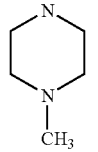 | —CH₃ | H | H | 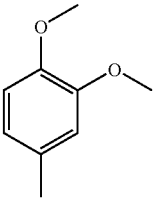 |
| 9 3,4-dimethoxy-N-{4-(4-methyl-1-piperazinyl)-2-[(methylsulfonyl)amino]phenyl}benzenesulfonamide | 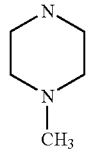 | —CH₃ | H | H | 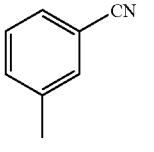 |
| 10 3-cyano-N-{4-(4-methyl-1-piperazinyl)-2-[(methylsulfonyl)amino]phenyl}benzenesulfonamide | 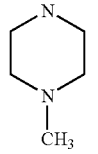 | —CH₃ | H | H | 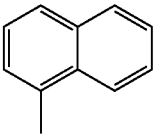 |
| 11 N-{4-(1-piperazinyl)-2-[(phenylsulfonyl)amino]phenyl}-1-naphthalenesulfonamide | 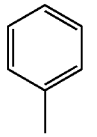 | 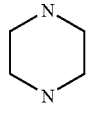 | H | H | 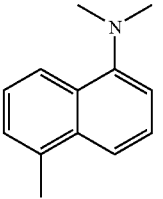 |
| 12 5-(dimethylamino)-N-{4-(1-piperazinyl)-2-[(phenylsulfonyl)amino]phenyl}-1-naphthalenesulfonamide | 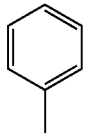 | 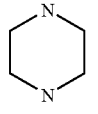 | H | H |  |

TABLE I-continued

Compounds of the formula I wherein R² is —SO₂—R¹'

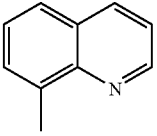

| Name | R¹ | R¹' | R³ | R⁴ | R⁵ |
|---|---|---|---|---|---|
| 13 N-[2-[(phenylsulfonyl)amino]-4-(1-piperazinyl)phenyl]-8-quinolinesulfonamide | 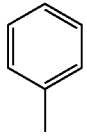 |  | H | H | 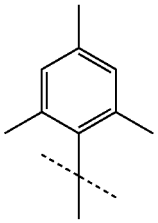 |
| 14 2,4,6-trimethyl-N-[2-[(phenylsulfonyl)amino]-4-(1-piperazinyl)phenyl]benzenesulfonamide | 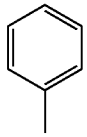 |  | H | H | 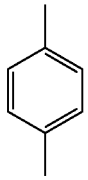 |
| 15 4-methyl-N-[2-[(phenylsulfonyl)amino]-4-(1-piperazinyl)phenyl]benzenesulfonamide | 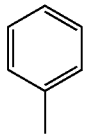 |  | H | H | 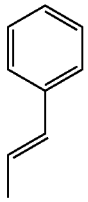 |
| 16 N-[2-({[(E)-2-phenylethenyl]sulfonyl}amino)-5-(1-piperazinyl)phenyl]benzenesulfonamide | 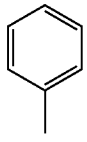 |  | H | H | 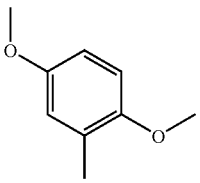 |
| 17 2,5-dimethoxy-N-[2-[(phenylsulfonyl)amino]-4-(1-piperazinyl)phenyl]benzenesulfonamide | 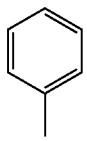 |  | H | H | 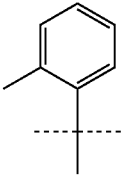 |
| 18 2-methyl-N-[2-[(phenylsulfonyl)amino]-4-(1-piperazinyl)phenyl]benzenesulfonamide | 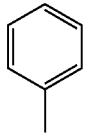 |  | H | H |  |

TABLE I-continued

Compounds of the formula I wherein R² is —SO₂—R¹'

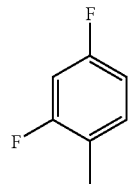

| Name | R¹ | R¹' | R³ | R⁴ | R⁵ |
|------|----|----|----|----|----|
| 19 2,4-difluoro-N-[2-[(phenylsulfonylamino]-4-(1-piperazinyl)phenyl]benzenesulfonamide | 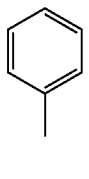 | 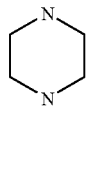 | H | H | 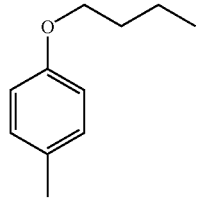 |
| 20 4-butoxy-N-[2-[(phenylsulfonyl)amino]-4-(1-piperazinyl)phenyl]benzenesulfonamide | 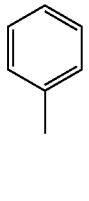 | 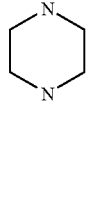 | H | H | 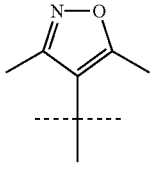 |
| 21 3,5-dimethyl-N-[2-[(phenylsulfonyl)amino]-4-(1-piperazinyl)phenyl]-4-isoxazolesulfonamide | 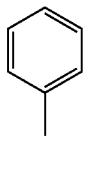 | 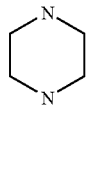 | H | H | 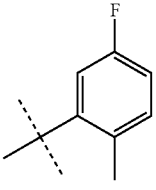 |
| 22 5-fluoro-2-methyl-N-[2-[(phenylsulfonyl)amino]-4-(1-piperazinyl)phenyl]benzenesulfonamide | 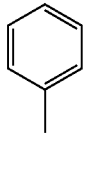 | 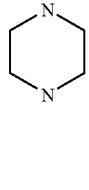 | H | H | 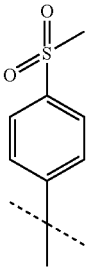 |
| 23 4-(methylsulfonyl)-N-[2-[(phenylsulfonyl)amino]-4-(1-piperazinyl)phenyl]benzenesulfonamide | 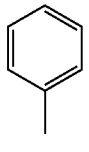 | 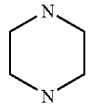 | H | H | |

TABLE I-continued

Compounds of the formula I wherein $R^2$ is $-SO_2-R^{1'}$

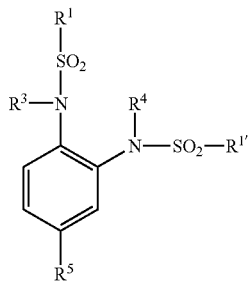

| Name | $R^1$ | $R^{1'}$ | $R^3$ | $R^4$ | $R^5$ |
|---|---|---|---|---|---|
| 24 2-(methylsulfonyl)-N-[2-[(phenylsulfonyl)amino]-4-(1-piperazinyl)phenyl]benzenesulfonamide | 2-(methylsulfonyl)phenyl | phenyl | H | H | piperazinyl |
| 25 2-methoxy-4-methyl-N-[2-[(phenylsulfonyl)amino]-4-(1-piperazinyl)phenyl]benzenesulfonamide | 2-methoxy-4-methylphenyl | phenyl | H | H | piperazinyl |
| 26 4-methoxy-2-methyl-N-[2-[(phenylsulfonyl)amino]-4-(1-piperazinyl)phenyl]benzenesulfonamide | 4-methoxy-2-methylphenyl | phenyl | H | H | piperazinyl |
| 27 N-{4-(1,4-diazepan-1-yl)-2-[(phenylsulfonyl)amino]phenyl}benzenesulfonamide | phenyl | phenyl | H | H | 1,4-diazepan-1-yl |
| 28 N-(4-(1,4-diazepan-1-yl)-2-{[(3-fluorophenyl)sulfonyl]-amino}phenyl)-3-fluorobenzenesulfonamide | 3-fluorophenyl | 3-fluorophenyl | H | H | 1,4-diazepan-1-yl |
| 29 N-{5-(1,4-diazepan-1-yl)-2-[(phenylsulfonyl)amino]phenyl}-N-ethylbenzenesulfonamide | phenyl | phenyl | H | Et | 1,4-diazepan-1-yl |

TABLE I-continued

Compounds of the formula I wherein $R^2$ is $-SO_2-R^{1'}$

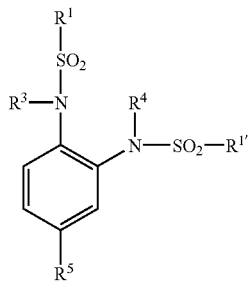

| Name | $R^1$ | $R^{1'}$ | $R^3$ | $R^4$ | $R^5$ |
|---|---|---|---|---|---|
| 30 N-{5-(1,4-diazepan-1-yl)-2-[(methylsulfonyl)amino]phenyl}benzenesulfonamide | Me | Ph-4-yl (tolyl) | H | H | 1,4-diazepan-1-yl |
| 31 N-{5-(1,4-diazepan-1-yl)-2-[(ethylsulfonyl)amino]phenyl}benzenesulfonamide | Et | tolyl | H | H | 1,4-diazepan-1-yl |
| 32 N-{4-(1,4-diazepan-1-yl)-2-[(phenylsulfonyl)amino]phenyl}[1,1'-biphenyl]-4-sulfonamide | Ph | tolyl | H | H | 1,4-diazepan-1-yl |
| 33 N-{4-(1,4-diazepan-1-yl)-2-[(phenylsulfonyl)amino]phenyl}-2,1,3-benzoxadiazole-4-sulfonamide | benzoxadiazolyl | tolyl | H | H | 1,4-diazepan-1-yl |
| 34 N-{4-(1,4-diazepan-1-yl)-2-[(phenylsulfonyl)amino]phenyl}-2-naphthalenesulfonamide | 2-naphthyl | tolyl | H | H | 1,4-diazepan-1-yl |
| 35 N-{4-(1,4-diazepan-1-yl)-2-[(methylsulfonyl)amino]phenyl}benzenesulfonamide | tolyl | Me | H | H | 1,4-diazepan-1-yl |
| 36 N-{4-(1,4-diazepan-1-yl)-2-[methyl(methylsulfonyl)amino]phenyl}benzenesulfonamide PHA-526210A | tolyl | Me | H | Me | 1,4-diazepan-1-yl |

TABLE I-continued

Compounds of the formula I wherein $R^2$ is $-SO_2-R^{1'}$

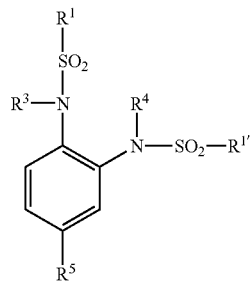

| Name | $R^1$ | $R^{1'}$ | $R^3$ | $R^4$ | $R^5$ |
|---|---|---|---|---|---|
| 37 N-{4-(1,4-diazepan-1-yl)-2-[(methylsulfonyl)amino]phenyl}-N-methylbenzenesulfonamide | phenyl | Me | Me | H | 1,4-diazepan-1-yl |
| 38 N-{4-(1,4-diazepan-1-yl)-2-[methyl(phenylsulfonyl)amino]phenyl}benzenesulfonamide | phenyl | phenyl | H | Me | 1,4-diazepan-1-yl |
| 39 N-{4-(1,4-diazepan-1-yl)-2-[(methylsulfonyl)amino]phenyl}-1-naphthalenesulfonamide | 1-naphthyl | Me | H | Me | 1,4-diazepan-1-yl |
| 40 N-{4-(1,4-diazepan-1-yl)-2-[(methylsulfonyl)amino]phenyl}-2-naphthalenesulfonamide | 2-naphthyl | Me | H | H | 1,4-diazepan-1-yl |
| 41 N-{4-(1,4-diazepan-1-yl)-2-[(methylsulfonyl)amino]phenyl}-4-fluorobenzenesulfonamide | 4-fluorophenyl | Me | H | H | 1,4-diazepan-1-yl |
| 42 N-{4-(1,4-diazepan-1-yl)-2-[(methylsulfonyl)amino]phenyl}-4-nitrobenzenesulfonamide | 4-nitrophenyl | Me | H | H | 1,4-diazepan-1-yl |
| 43 N-{4-(1,4-diazepan-1-yl)-2-[(methylsulfonyl)amino]phenyl}-3-(trifluoromethyl)benzenesulfonamide | 3-(trifluoromethyl)phenyl | Me | H | H | 1,4-diazepan-1-yl |

TABLE I-continued

Compounds of the formula I wherein R² is —SO₂—R¹'

| Name | R¹ | R¹' | R³ | R⁴ | R⁵ |
|---|---|---|---|---|---|
| 44 N-{4-(1,4-diazepan-1-yl)-2-[(methylsulfonyl)amino]phenyl}-2-methylbenzenesulfonamide | 2-methylphenyl | Me | H | H | 1,4-diazepan-1-yl |
| 45 N-{4-(1,4-diazepan-1-yl)-2-[(methylsulfonyl)amino]phenyl}-4-(trifluoromethoxy)benzenesulfonamide | 4-(trifluoromethoxy)phenyl | Me | H | H | 1,4-diazepan-1-yl |
| 46 N-{4-(1,4-diazepan-1-yl)-2-[(methylsulfonyl)amino]phenyl}-3,5-dimethyl-4-isoxazolesulfonamide | 3,5-dimethyl-4-isoxazolyl | Me | H | H | 1,4-diazepan-1-yl |
| 47 N-{4-(1,4-diazepan-1-yl)-2-[(methylsulfonyl)amino]phenyl}-3-methoxybenzenesulfonamide | 3-methoxyphenyl | Me | H | H | 1,4-diazepan-1-yl |
| 48 N-{4-(1,4-diazepan-1-yl)-2-[(methylsulfonyl)amino]phenyl}-4-methylbenzenesulfonamide | 4-methylphenyl | Me | H | H | 1,4-diazepan-1-yl |
| 49 N-{4-(1,4-diazepan-1-yl)-2-[ethyl(methylsulfonyl)amino]phenyl}-4-methylbenzenesulfonamide | 4-methylphenyl | Me | H | Et | 1,4-diazepan-1-yl |

TABLE I-continued

Compounds of the formula I wherein $R^2$ is —SO$_2$—R$^{1'}$

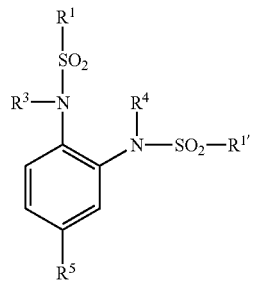

| Name | R$^1$ | R$^{1'}$ | R$^3$ | R$^4$ | R$^5$ |
|---|---|---|---|---|---|
| 50 N-{4-(1,4-diazepan-1-yl)-2-[ethyl(methylsulfonyl)amino]phenyl}-3,4-dimethoxybenzenesulfonamide | 3,4-dimethoxyphenyl | Me | H | Et | 1,4-diazepan-1-yl |
| 51 N-{4-(1,4-diazepan-1-yl)-2-[ethyl(methylsulfonyl)amino]phenyl}-7-quinolinesulfonamide | 7-quinolinyl | Me | H | Et | 1,4-diazepan-1-yl |
| 52 N-{4-(1,4-diazepan-1-yl)-2-[methyl(methylsulfonyl)amino]phenyl}-4-methylbenzenesulfonamide | 4-methylphenyl | Me | H | Me | 1,4-diazepan-1-yl |
| 53 N-{4-(1,4-diazepan-1-yl)-2-[methyl(methylsulfonyl)amino]phenyl}-1-naphthalenesulfonamide | 1-naphthyl | Me | H | Me | 1,4-diazepan-1-yl |
| 54 N-{4-(1,4-diazepan-1-yl)-2-[methyl(methylsulfonyl)amino]phenyl}-5-(2-pyridinyl)-2-thiophenesulfonamide | 5-(2-pyridinyl)-2-thienyl | Me | H | Me | 1,4-diazepan-1-yl |
| 55 N-{4-(1,4-diazepan-1-yl)-2-[(phenylsulfonyl)amino]phenyl}-1-naphthalenesulfonamide | 1-naphthyl | phenyl | H | H | 1,4-diazepan-1-yl |
| 56 N-{4-(1,4-diazepan-1-yl)-2-[(phenylsulfonyl)amino]phenyl}-5-(dimethylamino)-1-naphthalenesulfonamide | 5-(dimethylamino)-1-naphthyl | phenyl | H | H | 1,4-diazepan-1-yl |

TABLE I-continued

Compounds of the formula I wherein $R^2$ is —$SO_2$—$R^{1'}$

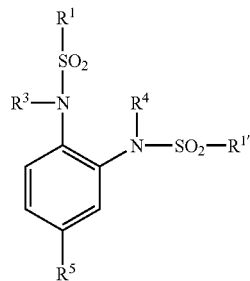

| Name | $R^1$ | $R^{1'}$ | $R^3$ | $R^4$ | $R^5$ |
|---|---|---|---|---|---|
| 57 N-{4-(1,4-diazepan-1-yl)-2-[(phenylsulfonyl)amino]phenyl}-8-quinolinesulfonamide | 8-quinolinyl | phenyl | H | H | 1,4-diazepan-1-yl |
| 58 N-{4-(1,4-diazepan-1-yl)-2-[(phenylsulfonyl)amino]phenyl}-2,4,6-trimethylbenzenesulfonamide | 2,4,6-trimethylphenyl | phenyl | H | H | 1,4-diazepan-1-yl |
| 59 N-{4-(1,4-diazepan-1-yl)-2-[(phenylsulfonyl)amino]phenyl}-4-methylbenzenesulfonamide | 4-methylphenyl | phenyl | H | H | 1,4-diazepan-1-yl |
| 60 N-[5-(1,4-diazepan-1-yl)-2-({[(E)-2-phenylethenyl]sulfonyl}amino)phenyl]benzenesulfonamide | (E)-2-phenylethenyl | phenyl | H | H | 1,4-diazepan-1-yl |
| 61 N-{4-(1,4-diazepan-1-yl)-2-[(phenylsulfonyl)amino]phenyl}-2,5-dimethoxybenzenesulfonamide | 2,5-dimethoxyphenyl | phenyl | H | H | 1,4-diazepan-1-yl |
| 62 N-{4-(1,4-diazepan-1-yl)-2-[(phenylsulfonyl)amino]phenyl}-2-methylbenzenesulfonamide | 2-methylphenyl | phenyl | H | H | 1,4-diazepan-1-yl |

TABLE I-continued

Compounds of the formula I wherein R² is —SO₂—R¹'

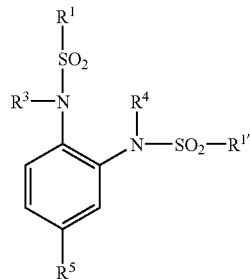

| Name | R¹ | R¹' | R³ | R⁴ | R⁵ |
|---|---|---|---|---|---|
| 63 4-butoxy-N-{4-(1,4-diazepan-1-yl)-2-[(phenylsulfonyl)amino]phenyl}benzenesulfonamide | 4-butoxyphenyl | phenyl | H | H | 1,4-diazepan-1-yl |
| 63 N-{4-(1,4-diazepan-1-yl)-2-[(phenylsulfonyl)amino]phenyl}-3,5-dimethyl-4-isoxazolesulfonamide | 3,5-dimethylisoxazol-4-yl | phenyl | H | H | 1,4-diazepan-1-yl |
| 65 N-{4-(1,4-diazepan-1-yl)-2-[(phenylsulfonyl)amino]phenyl}-5-fluoro-2-methylbenzenesulfonamide | 5-fluoro-2-methylphenyl | phenyl | H | H | 1,4-diazepan-1-yl |
| 66 N-{4-(1,4-diazepan-1-yl)-2-[(phenylsulfonyl)amino]phenyl}-4-(methylsulfonyl)benzenesulfonamide | 4-(methylsulfonyl)phenyl | phenyl | H | H | 1,4-diazepan-1-yl |

TABLE I-continued

Compounds of the formula I wherein R² is —SO₂—R¹'

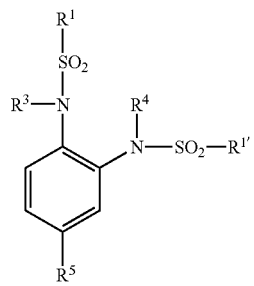

| Name | R¹ | R¹' | R³ | R⁴ | R⁵ |
|---|---|---|---|---|---|
| 67 N-{4-(1,4-diazepan-1-yl)-2-[(methylsulfonyl)amino]phenyl}-N-methylbenzenesulfonamide | 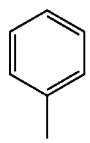 | Me | Me | H | 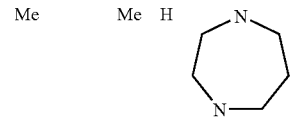 |
| 68 N-{5-(1,4-diazepan-1-yl)-2-[methyl(phenylsulfonyl)amino]phenyl}-4-methylbenzenesulfonamide | 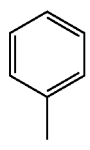 | 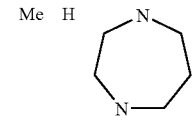 | Me | H | 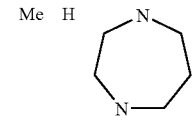 |

TABLE II

Compounds of the formula Ia

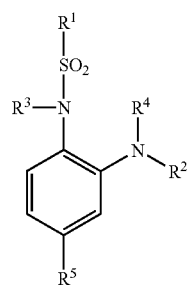

| Name | R¹ | R³ | R² | R⁴ | R⁵ |
|---|---|---|---|---|---|
| 69 N-[2-amino-4-(1-piperazinyl)phenyl]-3-fluorobenzenesulfonamide | 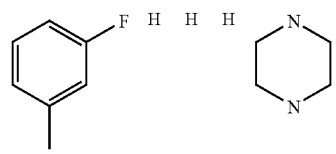 F | H | H | H | 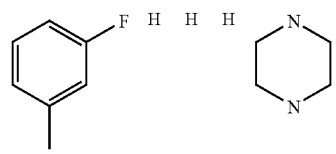 |

TABLE II-continued

Compounds of the formula Ia

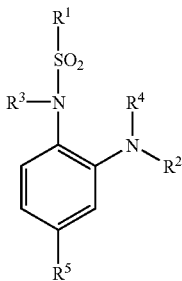

| Name | R¹ | R³ | R² | R⁴ | R⁵ |
|---|---|---|---|---|---|
| 70 N-[2-(ethylamino)-4-(1-piperazinyl)phenyl]-3-fluorobenzenesulfonamide | 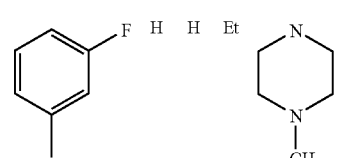 F | H | H | Et | 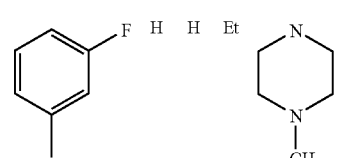 |

Compounds of the Formula II

In a further aspect, the invention provides a compound having the general formula (II)

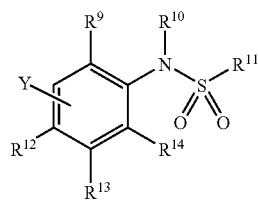

or a pharmaceutically acceptable salt thereof, wherein
$R^9$, $R^{12}$ and $R^{14}$ are H; or
two of $R^9$, $R^{12}$ and $R^{14}$ are H; and the remaining of $R^9$, $R^{12}$ and $R^{14}$ is
(a) —$NH_2$,
(b) —$NHR^6$,
(c) —$NR^6R^7$,
(d) —$N(CO)R^6$,
(e) —$N(CS)R^6$, or
(f) —$NO_2$;
$R^{10}$ and $R^{11}$ is a group $R^3$ or $R^1$ as defined for Formula I;
$R^{13}$ is
(a) homopiperazine,
(b) methylhomopiperazine or
(c) a group $R^5$ as defined for Formula I, wherein $R^8$ is as defined for Formula I;
Y is as defined for Formula I.

Preferred compounds of the general formula (II) are those wherein:
$R^{13}$ is
(a) homopiperazine,
(b) methylhomopiperazine, or
(c) a group $R^5$ selected from

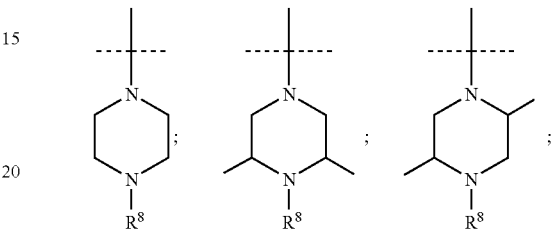

$R^8$ is
(a) H, or
(b) $C_{1-6}$ alkyl, in particular methyl;

TABLE III

Compounds of the formula II wherein $R^{10}$, $R^{14}$ and Y are H

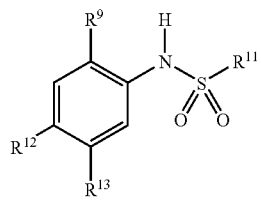

| Name | $R^9$ | $R^{11}$ | $R^{12}$ | $R^{13}$ |
|---|---|---|---|---|
| 71 4-chloro-N-[5-(4-methyl-1,4-diazepan-1-yl)-2-nitrophenyl]benzenesulfonamide | —$NO_2$ | 4-Cl-C₆H₄ | H | 4-methyl-1,4-diazepan-1-yl |
| 72 N-[2-amino-5-(1,4-diazepan-1-yl)phenyl]benzenesulfonamide | —$NH_2$ | C₆H₅ | H | 1,4-diazepan-1-yl |
| 73 N-[2-amino-5-(4-methyl-1,4-diazepan-1-yl)phenyl]benzenesulfonamide | —$NH_2$ | C₆H₅ | H | 4-methyl-1,4-diazepan-1-yl |

TABLE III-continued

Compounds of the formula II wherein $R^{10}$, $R^{14}$ and Y are H

| Name | $R^9$ | $R^{11}$ | $R^{12}$ | $R^{13}$ |
|---|---|---|---|---|
| 74 N-[4-nitro-3-(1-piperazinyl)phenyl]benzenesulfonamide | H | phenyl | —NO$_2$ | piperazin-1-yl |
| 75 N-[4-amino-3-(1-piperazinyl)phenyl]benzenesulfonamide | H | phenyl | —NH$_2$ | piperazin-1-yl |

TABLE IV

Compounds wherein Y and group —N—$R^2$ $R^4$, is assigned as group R in the following structure and $R^5$ is a group

| Name | $R^1$ | $R^3$ | —R | $R^8$ |
|---|---|---|---|---|
| 76 3-amino-4-(1,4-diazepan-1-yl)-N-(4-methoxyphenyl)benzenesulfonamide | 4-methoxyphenyl | H | —NH$_2$ | H |

TABLE IV-continued

Compounds wherein Y and group —N—R² R⁴, is assigned as group R in the following structure and R⁵ is a group

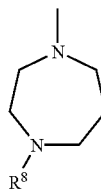

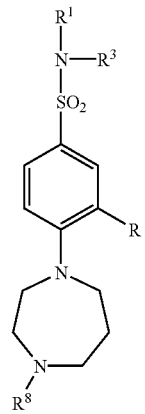

| Name | R¹ | R³ | —R | R⁸ |
|---|---|---|---|---|
| 77 3-amino-4-(1,4-diazepan-1-yl)-N-(3-methoxyphenyl)benzenesulfonamide | 3-methoxyphenyl | H | —NH₂ | H |
| 78 3-amino-4-(1,4-diazepan-1-yl)-N-(2-methoxyphenyl)benzenesulfonamide | 2-methoxyphenyl | H | —NH₂ | H |
| 79 3-amino-4-(1,4-diazepan-1-yl)-N-(3-fluorophenyl)benzenesulfonamide | 3-fluorophenyl | H | —NH₂ | H |
| 80 3-amino-4-(1,4-diazepan-1-yl)-N-methyl-N-phenylbenzenesulfonamide | phenyl | —CH₃ | —NH₂ | H |
| 81 3-amino-4-(1,4-diazepan-1-yl)-N-(4-isopropylphenyl)benzenesulfonamide | 4-isopropylphenyl | H | —NH₂ | H |

TABLE IV-continued

Compounds wherein Y and group —N—R² R⁴, is assigned as group R in the following structure and R⁵ is a group

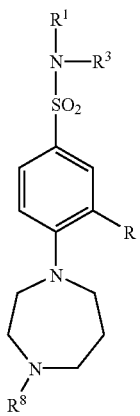

| Name | R¹ | R³ | —R | R⁸ |
|---|---|---|---|---|
| 82 3-amino-4-(1,4-diazepan-1-yl)-N-(4-methylphenyl)benzenesulfonamide | 4-methylphenyl | H | —NH₂ | H |
| 83 3-amino-4-(1,4-diazepan-1-yl)-N-(2,5-dimethylphenyl)benzenesulfonamide | 2,5-dimethylphenyl | H | —NH₂ | H |
| 84 3-amino-N-(3-chlorophenyl)-4-(1,4-diazepan-1-yl)benzenesulfonamide | 3-chlorophenyl | H | —NH₂ | H |
| 85 3-amino-N-(2-chlorophenyl)-4-(1,4-diazepan-1-yl)benzenesulfonamide | 2-chlorophenyl | H | —NH₂ | H |
| 86 3-amino-N-(2,4-dichlorophenyl)-4-(1,4-diazepan-1-yl)benzenesulfonamide | 2,4-dichlorophenyl | H | —NH₂ | H |

TABLE IV-continued

Compounds wherein Y and group —N—R² R⁴, is assigned as group R in the following structure and R⁵ is a group

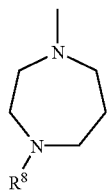

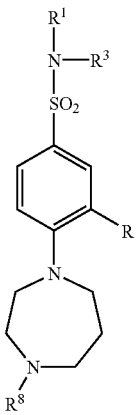

| Name | R¹ | R³ | —R | R⁸ |
|---|---|---|---|---|
| 87 3-amino-N-(2-methyl-5-chloro-phenyl)-4-(1,4-diazepan-1-yl)benzenesulfonamide | 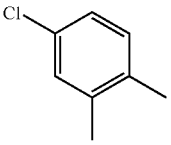 | H | —NH₂ | H |
| 88 3-amino-N-(2-methyl-3-chloro-phenyl)-4-(1,4-diazepan-1-yl)benzenesulfonamide | 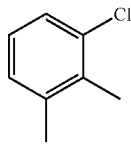 | H | —NH₂ | H |
| 89 3-amino-N-(4-trifluoro-phenyl)-4-(1,4-diazepan-1-yl)benzenesulfonamide | 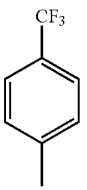 | H | —NH₂ | H |
| 90 3-amino-N-(4-fluorophenyl)-4-(1,4-diazepan-1-yl)benzenesulfonamide | 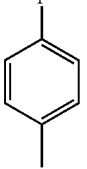 | H | —NH₂ | H |
| 91 3-amino-N-(2-fluorophenyl)-4-(1,4-diazepan-1-yl)benzenesulfonamide | 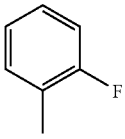 | H | —NH₂ | H |

TABLE IV-continued

Compounds wherein Y and group —N—R² R⁴, is assigned as group R in the following structure and R⁵ is a group

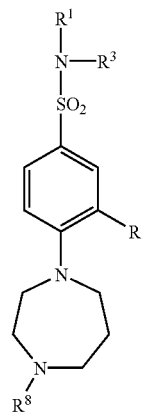

| Name | R¹ | R³ | —R | R⁸ |
|---|---|---|---|---|
| 92 3-amino-4-(4-methyl-1,4-diazepan-1-yl)-N-phenylbenzenesulfonamide | 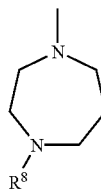 | H | —NH₂ | —CH₃ |
| 93 4-(1,4-diazepan-1-yl)-3-nitro-N-phenylbenzenesulfonamide | (phenyl) | H | —NO₂ | H |
| 94 3-amino-4-(1,4-diazepan-1-yl)-N-phenylbenzenesulfonamide | (phenyl) | H | —NH₂ | H |
| 95 2-(1,4-diazepan-1-yl)-5-(4-morpholinylsulfonyl)phenylamine | (morpholinyl) | H | —NH₂ | H |
| 96 4-(1,4-diazepan-1-yl)-N-phenyl-3-[(phenylsulfonyl)amino]benzenesulfonamide | (phenyl) | H | (phenyl-NH-SO₂-) | H |

TABLE IV-continued

Compounds wherein Y and group —N—R² R⁴, is assigned as group R in the following structure and R⁵ is a group

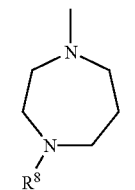

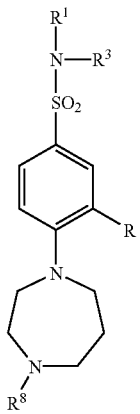

| Name | R¹ | R³ | —R | R⁸ |
|---|---|---|---|---|
| 97 4-(1,4-diazepan-1-yl)-N-phenyl-3-[(methylsulfonyl)amino]benzenesulfonamide | phenyl | H | CH₃—SO₂—HN— | H |

TABLE V

Compounds wherein Y, R³, R² and R⁴ are H

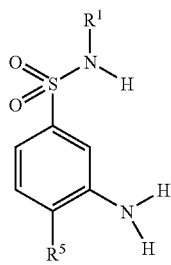

| Name | R¹ | R⁵ |
|---|---|---|
| 98 3-amino-N-(3-chlorophenyl)-4-(4-methyl-1-piperazinyl)benzenesulfonamide | 3-chlorophenyl | 4-methylpiperazin-1-yl |
| 99 3-amino-N-(2-methoxyphenyl)-4-(4-methyl-1-piperazinyl)benzenesulfonamide | 2-methoxyphenyl | 4-methylpiperazin-1-yl |

TABLE V-continued

Compounds wherein Y, R³, R² and R⁴ are H

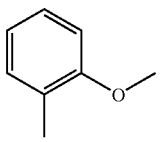

| Name | R¹ | R⁵ |
|---|---|---|
| 100 3-amino-N-(2-methoxyphenyl)-4-(1-piperazinyl)benzenesulfonamide |  | 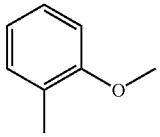 |
| 101 3-amino-N-(2-methoxyphenyl)-4-(3-methyl-1-lpiperazinyl)benzenesulfonamide | 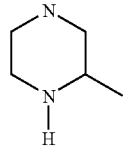 | 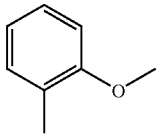 |
| 102 3-Amino-4-(hexahydro-pyrrolo[1,2-a]pyrazin-2-yl)-N-(2-methoxyphenyl)-benzenesulfonamide | 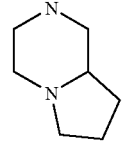 | 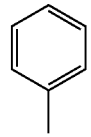 |
| 103 3-Amino-N-phenyl-4-piperazin-1-yl-benzenesulfonamide hydrochloride | 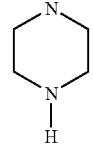 | 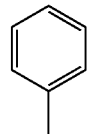 |
| 104 3-Amino-4-(3-methyl-piperazin-1-yl)-N-phenyl-benzenesulfonamide hydrochloride | 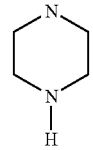 | 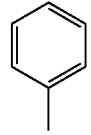 |
| 105 3-Amino-4-(4-ethyl-piperazin-1-yl)-N-phenyl-benzenesulfonamide hydrochloride | 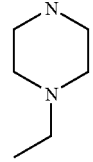 | 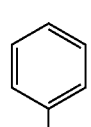 |
| 106 3-Amino-4-(hexahydro-pyrrolo[1,2-a]pyrazin-2-yl)-N-phenyl-benzenesulfonamide hydrochloride | 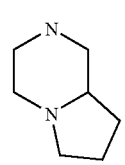 | |

TABLE V-continued

Compounds wherein Y, $R^3$, $R^2$ and $R^4$ are H

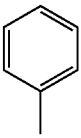

| Name | $R^1$ | $R^5$ |
|---|---|---|
| 107 3-Amino-4-(5-methyl-2,5-diaza-bicyclo[2.2.1]hept-2-yl)-N-phenyl-benzenesulfonamide hydrochloride | 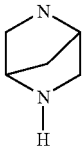 | 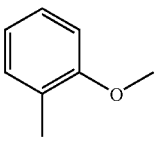 |
| 108 3-Amino-4-(trans-2,5-dimethyl-piperazin-1yl)-N-(2methoxy-phenyl)benzenesulfonamide hydrochloride | 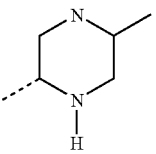 | 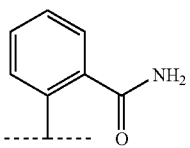 |
| 109 2-(3-Amino-4-[1,4]diazepan-1-yl-benzenesulfonyl)-benzamide diacetic acid | 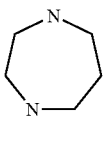 |  |
| 110 4-[4-(3-Fluoro-2-methoxy-phenylsulfamoyl)-2-amino-phenyl]-[1,4]diazepane ditrifluoroacetic acid | 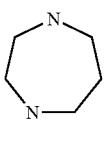 | 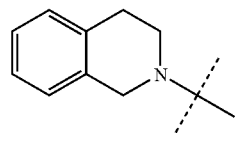 |
| 111 2-[1,4]Diazepan-1-yl-5-(3,4-dihydro-1H-isoquinoline-2-sulfonyl)-aniline dihydrochloride | 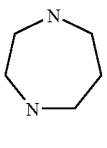 | 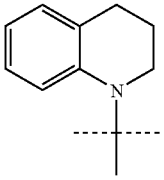 |
| 112 4-[4-(3,4-Dihydro-2H-quinoline-1-sulfonyl)-2-amino-phenyl]-[1,4]diazepane ditrifluoroacetic acid | 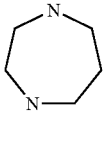 | |

TABLE VI

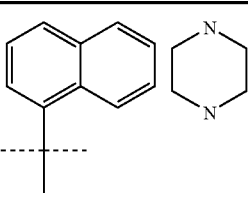

| Name | R¹ | R⁵ |
|---|---|---|
| 113 3-Amino-2-chloro-N-naphthalen-1-yl-4-piperazin-1-yl-benzenesulfonamide, hydrochloride | naphthalen-1-yl | piperazin-1-yl |

The compounds in the tables are hydrochloride salts, reported if otherwise

Processes for Preparation

The compounds according to the invention having two sulfonyl groups were prepared according to the methods outlined in Schemes 1, 2 and 3.

Scheme 1

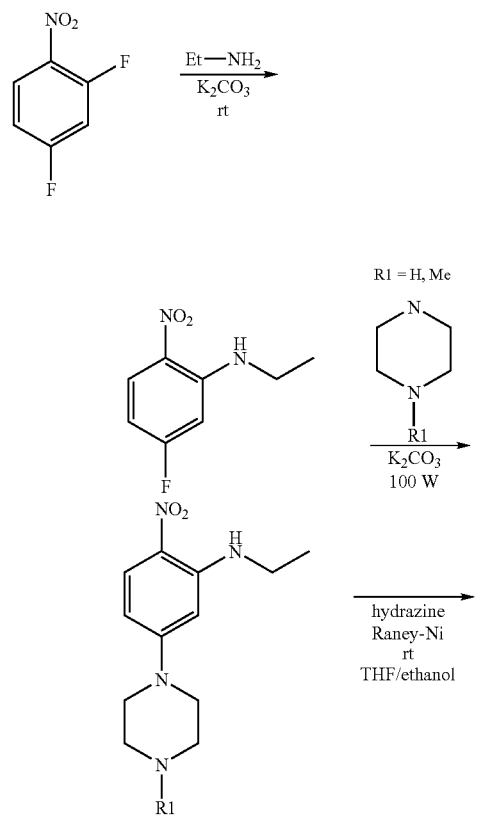

Scheme 2

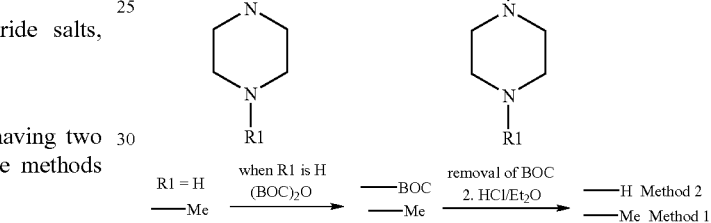

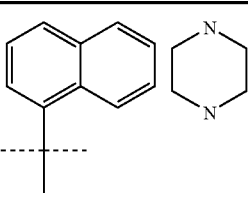

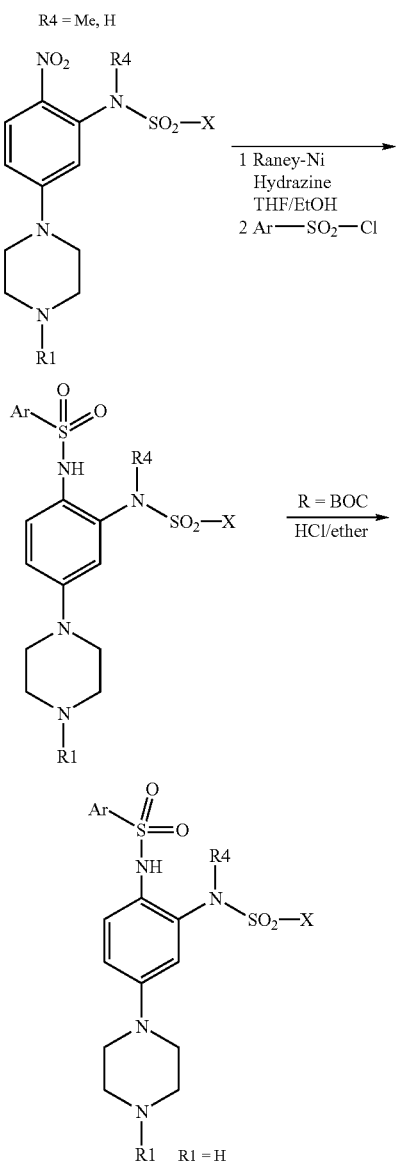
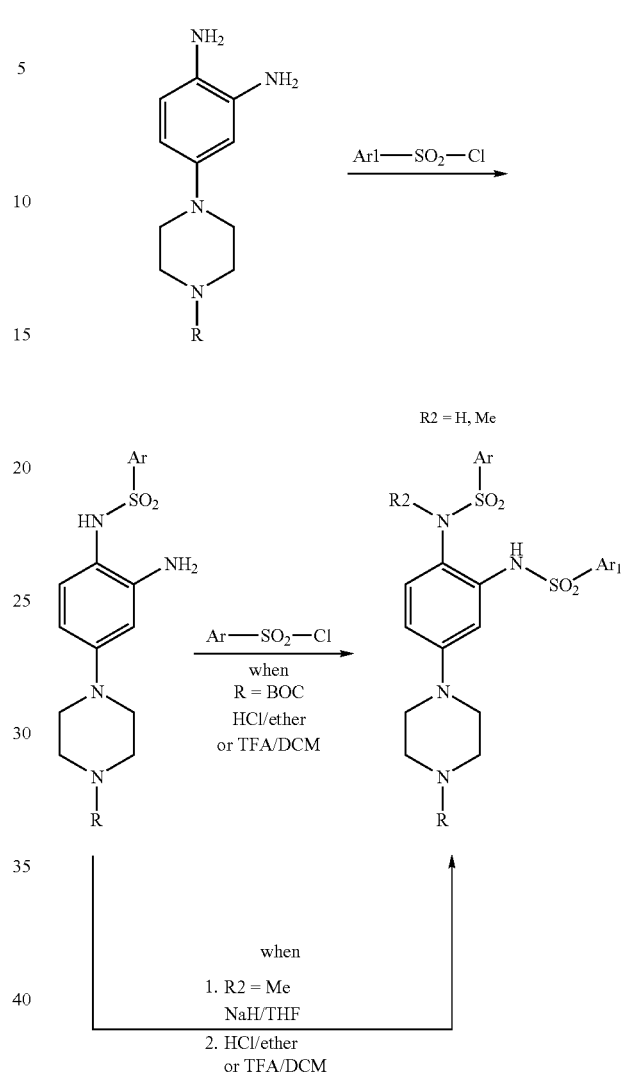

Scheme 3

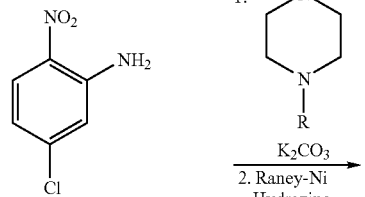
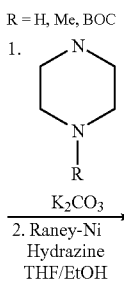

Depending on the process conditions the end products of the Formula I are obtained either in neutral or salt form. Both the free base and the salts of these end products are within the scope of the invention.

Acid addition salts of the new compounds may in a manner known per se be transformed into the free base using basic agents such as alkali or by ion exchange. The free base obtained may also form salts with organic or inorganic acids.

In the preparation of acid addition salts, preferably such acids are used which form suitably therapeutically acceptable salts. Examples of such acids are hydrohalogen acids, sulfuric acid, phosphoric acid, nitric acid, aliphatic, alicyclic, aromatic or heterocyclic carboxyl or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybensoic acid, embonic acid, methanesulfonic acid, ethanesulfonic acid, hydroxyethanesulfonic acid, halogenbensenesulfonic acid, toluenesulfonic acid, mandelic acid or naphthalenesulfonic acid.

Throughout the specification and the appended claims, a given chemical formula or name shall encompass all stereo and optical isomers and racemates thereof where such isomers exist. All diastereomeric forms possible (pure enantiomers, tautomers, racemic mixtures and unequal mixtures of two enantiomers) are within the scope of the invention. Such compounds can also occur as cis- or trans-, E- or Z-double bond isomer forms. All isomeric forms are contemplated.

Pharmaceutical Formulations

Pharmaceutical formulations are usually prepared by mixing the active substance, or a pharmaceutically acceptable salt thereof, with conventional pharmaceutical excipients. The formulations can be further prepared by known methods such as granulation, compression, microencapsulation, spray coating, etc.

This invention relates to a method of treating obesity or type II diabetes. The method includes administering to a mammal subject (e.g., human) in need thereof an effective amount of one or more compounds of the formula (I) or the formula (II) above. Also witnhin the scope of this invention is a method for modulating (e.g., inhibiting) 5-HT$_6$ receptor activity. The method includes administering to a mammal in need thereof an effective amount of a compound of the formula (I) or the formula (II) above.

"An effective amount" refers to an amount of a compound which confers a therapeutic effect on the treated subject. The therapeutic effect may be objective (i.e., measurable by some test or marker) or subjective (i.e., subject gives an indication of or feels an effect). For clinical use, the compounds of the invention are formulated into pharmaceutical formulations for oral, rectal, parenteral or other mode of administration. Usually the amount of active compounds is between 0.1–95% by weight of the preparation, preferably between 0.2–20% by weight in preparations for parenteral use and preferably between 1 and 50% by weight in preparations for oral administration.

The typical daily dose of the active substance varies within a wide range and will depend on various factors such as for example the individual requirement of each patient and the route of administration. In general, oral and parenteral dosages will be in the range of 5 to 1000 mg per day of active substance, preferably 50 to 150 mg per day.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLES

In the following examples, the structure of the prepared compounds were confirmed by standard spectroscopic methods and elemental analysis and/or high resolution MS. The NMR data were obtained on a JEOL JNM-EX 270, a Bruker 400 DPX or a Bruker DRX 500 spectrometer. IR spectra were obtained on a Perkin Elmer SPECTRUM 1000 FT-IR spectrometer. High resolution MS were obtained on a Micromass LCT spectrometer. Elemental analysis was performed by Mikro Kemi AB Uppsala Sweden. Melting points, when given, were obtained on a Büchi or a Gallenkamp melting point apparatus and are uncorrected.

Synthesis According to Scheme 1, Method 2 (R=Boc)

Intermediate 1

Synthesis of N-Ethyl-5-fluoro-2-nitroaniline

A suspension of 2,4-difluoro-1-nitrobenzene (0.50 g, 0.003 mmol), ethylamine hydrochloride (0.49 g, 0.006 mmol), K$_2$CO$_3$ (1.66 g, 0.012 mmol) in acetonitrile (30 mL) was stirred at room temperature for 16 hours and then filtered. The filtrate was concentrated and dissolved in small amount of CHCl$_3$. Purification by column chromatography on silica using pentane/diethyl ether 95:5 as eluent gave 0.45 g of a yellow solid. $^1$H NMR (CDCl$_3$) δ 8.23–8.18 (m, 1H), 8.08 (br s, 1H), 6.49–6.45 (m, 1H), 6.38–6.32 (m, 1H), 3.34–3.27 (m,2H), 1.38 (tr, J=7.22 Hz, 3H); $^{13}$C NMR (CDCl$_3$) δ 167.55 (d, J$_{CF}$=255.6 Hz), 147.4 (d, J$_{CF}$=12.9 Hz), 129.91 (d, J$_{CF}$=12.9 Hz), 128.71 (br s), 103.73 (d, J$_{CF}$=24.8 Hz), 99.14 (d, J$_{CF}$=27.6 Hz), 37.88, 14.05; MS (posESI) m/z=found 184.0653, calc 184.0648. Anal. (C$_2$H$_{18}$N$_4$O$_2$) C, H, N.

Intermediate 2

Synthesis of N-Ethyl-2-nitro-5-(1-piperazinyl)aniline

A suspension of N-ethyl-5-fluoro-2-nitroaniline (1.5 g, 8.12 mmol), piperazine (0.979 g, 11.37 mmol), K$_2$CO$_3$ (3.36 g, 24.3 mmol) in DMF (40 mL) was heated in a microwave oven for 1 min at 100 W. The reaction mixture was allowed to cool and then heated for another minute at 100 w. This procedure was repeated 5 times. The suspension was filtered and then concentrated. The crude oil was purified via flash chromatography on silica using CHCl$_3$/MeOH/NH$_3$ 9:1: 0.4% as eluent to give 1.53 g (75%) of a yellow solid. $^1$H NMR (CDCl$_3$) δ 8.30 (br s, 1H), 8.08–8.04 (m, 1H), 6.25–6.20 (m, 1H), 5.88–5.86 (m, 1H), 3.39–3.28 (m, 6H), 3.03–2.97 (m, 4H), 1.37 (tr, J=7.2 Hz, 3H); $^{13}$C NMR (CDCl$_3$) δ 156.27, 147.74, 128.96, 124.13, 104.28, 93.34, 48.22, 45.99, 37.73, 14.15; MS (posEI) m/z=250 (M$^+$); MS (posESI) m/z=found 250.1429, calc 250.1430. Anal (C$_{12}$H$_{18}$N$_4$O$_2$) C, H, O.

Intermediate 3

Synthesis of tert-Butyl 4-[3-(ethylamino)-4-nitrophenyl]-1-piperazinecarboxylate To a solution of N-ethyl-2-nitro-5-(1-piperazinyl)aniline (1.020 g, 4.075 mmol), and NaOH (0.39 g, 2.45 mmol) in THF:H$_2$O (64 mL, 1:1) was added a solution of di-tertbutyl-dicarbonate (2.67 g, 12.2 mmol) in 5 mL THF. The solution was stirred at room temperature for 16 hours. The mixture was neutralized with 1 N HCl. The volatiles were removed under vacuum to yield 1.4 g of crude material (98%). $^1$H NMR (CDCl$_3$) δ 8.28 (br s, 1H), 8.13–8.09 (m, 1H), 6.27–6.22 (m, 1H), 6.05–6.02 (m, 1H), 3.67–3.61 (m, 4H), 3.45–3.38 (m, 4H), 3.35–3.27 (m, 2H), 1.50 (s, 9H); MS (posESI) m/z=found 350.1951, calc 350.1954.

Intermediate 4

Synthesis of tert-Butyl 4-[4-amino-3-(ethylamino) phenyl]-1-piperazinecarboxylate To a solution of tert-butyl 4-[3-(ethylamino)-4-nitrophenyl]-1-piperazinecarboxylate (1.028 g, 2.93 mmol) in 40 mL EtOH:THF (4:1) solvent system was added Raney-Ni (1 mL of a EtOH suspension) followed by addition hydrazine hydrate (0.734 g, 14.67 mmol). The mixture was stirred vigorously for 3 hours and then filtered through a Celite pad pretreated with water. The filtrate was concentrated and then purified by column chromatography on silica using CHCl$_3$/MeOH/NH$_3$ 9:1:0.4% as eluent to give 0.877 g (93%) of a red oil. The oil was used immediately in the next reaction. HPLC purity>90 %; MS (posEI) m/z=320 (M$^+$);

Method 1, Scheme 1: General for Sulfonylation (R1=Me)

Intermediate 5

Synthesis of N-ethyl-5-(4-methyl-1-piperazinyl)-2-nitroaniline (Method 1, Scheme 1)

N-ethyl-5-(4-methyl-1-piperazinyl)-2-nitroaniline was prepared from 2,4-difluoro-1-nitrobenzene and methylpiperazine using the same method described for N-ethyl-2-nitro-5-(1-piperazinyl)aniline and was obtained as yellow solid (99%). $^1$H NMR (CDCl$_3$) δ 8.30 (br s, 1H), 8.08–8.04 (m, 1H), 6.25–6.20 (m, 1H), 5.89–5.86 (m, 1H), 3.45–3.39 (m, 4H), 3.35–3.25 (m, 2H), 2.56–2.50 (m, 4H), 2.35 (s, 3H), 1.37 (tr, J=7.2 Hz, 3)); $^{13}$C NMR δ(CDCl$_3$) 155.92, 147.72, 128.99, 124.19, 104.30, 94.37, 54.78, 47.05, 46.25, 37.73, 14.43; MS (posESI) m/z=found 264.1575, calc 264.1586. Anal. (C$_{13}$H$_{20}$N$_4$O$_2$,0.5 H$_2$O) C, H, O.

Intermediate 6

Synthesis of N-2-Ethyl-4-(4-methyl-1-piperazinyl)-1,2-benzenediamine (Method 1, Scheme 1)

N-Ethyl-5-(4-methyl-1-piperazinyl)-2-nitroaniline was reduced with Raney-Ni as described previously for the synthesis of tert-butyl 4-[4-amino-3-(ethylamino)phenyl]-1-piperazinecarboxylate to give N-2-ethyl-4-(4-methyl-1-piperazinyl)-1,2-benzenediamine (yield>90%) as a red oil. The product is very sensitive to oxidation and was therefore used immediately in the next reaction step. HPLC purity>90%; MS (posEI) m/z=234 (M$^+$);

Example 1

N-[2-{Ethyl[(3-fluorophenyl)sulfonyl]amino}-4-(4-methyl-1-piperazinyl)phenyl]-3-fluorobenzanesulfonamide hydrochloride (Method 1, Scheme 1)

To a solution of amine N-2-ethyl-4-(4-methyl-1-piperazinyl)-1,2-benzenediamine (0.200 g, 0.853 mmol) and pyridine (0.48 mL, 5.97 mmol) in CH$_2$Cl$_2$ (8 mL) was added a solution of 3-fluorobenzenesulfonyl chloride (249 mg, 1.28 mmol) in CH$_2$Cl$_2$ (2 mL). The mixture was stirred at room temperature for 16 hours. CH$_2$Cl$_2$ (10 mL) was added and the mixture was washed with saturated aqueous NaHCO$_3$. The organic layer was dried over Na$_2$SO$_4$, filtered and concentrated. Purification by column chromatography (Al$_2$O$_3$, EtOAc/MeOH 9.5:0.5) gave two products. The first fraction contained 110 mg of N-[2-{ethyl[(3-fluorophenyl)sulfonyl]amino}-4-(4-methyl-1-piperazinyl)phenyl]-3-fluorobenzanesulfonamide hydrochloride. The second fraction contained 100 mg of N-[2-(ethylamino)-4-(4-methyl-1-piperazinyl)phenyl]-3-fluorobenzanesulfonamide hydrochloride. Both products were converted to the HCl-salts.

N-[2-{ethyl[(3-fluorophenyl)sulfonyl]amino}-4-(4-methyl-1-piperazinyl)phenyl]-3-fluorobenzanesulfonamide hydrochloride: $^1$H NMR (DMSO-d6) δ 11.14 (br s, 1H), 9.27 (s, 1H), 7.75–7.35 (m, 8H), 7.18–7.15 8m, 1H), 6.95–6.90 (m, 1H), 6.07–6.04 (m, 1H), 3.47–3.30 (m, 4H), 3.05–2.85 (m, 4H), 2.73 8d, J=4.7 Hz), 0.72 (tr, J=7.2Hz); $^{13}$C NMR (CD$_3$OD) δ 162.65 (d, J$_{CF}$=5.5 Hz), 160.68 (d, J$_{CF}$=4.6 Hz), 146.61, 142.52 (d, J$_{CF}$=7.4 Hz), 139.04 (d, J$_{CF}$=6.4 Hz), 131.58 (131.63, 131.28, 128.67, 124.25, 123.14, 122.89, 120.56 (d, J$_{CF}$=21 Hz), 120.05 (d, J$_{CF}$=21 Hz), 116.52, 115.64, 114.80 (d, J$_{CF}$=25 Hz), 113.97 (d, J$_{CF}$=25 Hz), 51.88, 45.82, 44.84, 41.79, 12.31; Ms (posES-FIA) m/z=551 (M+H)

Example 2

N-[2-[ethyl(phenylsulfonyl)amino]-4-(4-methyl-1-piperazinyl)phenyl]-benzenesulfonamide hydrochloride (Scheme 1, Method 1)

N-[2-[ethyl(phenylsulfonyl)amino]-4-(4-methyl-1-piperazinyl)phenyl] benzenesulfonamide hydrochloride was prepared as described in Scheme 1. Sulfonylation from N-2-ethyl-4-(4-methyl-1-piperazinyl)-1,2-benzenediamine and phenylsulfonyl chloride was performed as described in Method 1. Purification by chromatography (SiO$_2$, chloroform:methanol:NH$_3$ 9:1:0.4%) followed by trituration with MeOH gave 68 mg (15% yield) of the free base which was converted to its HCl-salt. MS (posES-FIA) m/z=found: 514.1700, calc: 514.1708; Anal. (C$_{25}$H$_{30}$N$_4$O$_4$S$_2$.2HCl) C, H, N.

Example 3

3-Fluoro-N-[2-{[(3-fluorophenyl)sulfonyl]amino}-4-(4-methyl-1-piperazinyl)phenyl]benzenesulfonamide hydrochloride (Scheme 3)

Synthesis of 2-Amino-5-(4-methyl-1-piperazinyl)aniline. A mixture of 2-nitro-3-chloroaniline (4.47 g, 25.9 mmol), methylpiperazine (3.1 g, 31 mmol) and K$_2$CO$_3$ (5.41 g, 39 mmol) in acetonitrile was stirred at 70° C. for 48 h. The mixture was filtered and purified by column chromatography (SiO$_2$, CH$_2$Cl$_2$/MeOH/Heptane/NH$_3$ 4:1:5×0.2%) to give 1.6 g of product (unreacted starting material was isolated): $^1$H-NMR δ 7.66–7.45 (m, 5H), 6.78 (d, 1H), 6.62 (d, 1H), 6.50 (dd, 1H), 3.39–3.35 (m, 4H), 3.02-2.99 (m, 4H); MS (posES-FIA) m/z 333.0 (M$^+$+H). The product (1.06 g, 4.49 mmol) was dissolved in EtOH:THF (4:1). Raney-Ni and hydrazine (1.12 mL, 22 mmol) were added. The reaction was stirred at room temperature for 3 h until the yellow color disappeared. Filtration through wet Celite pad, followed by removal of the solvent afforded 0.802 g of 2-amino-5-(4-methyl-1-piperazinyl)aniline which was used without further purification in the next step. 3-Fluorobenzenesulfonyl chloride (0.133 g, 0.68 mmol) was added to a solution of 2-amino-5-(4-methyl-1-piperazinyl)aniline (0.141 g, 0.68 mmol) and pyridine (514 mL, 6.39 mmol) in CH$_2$Cl$_2$. After 1 h the mixture was washed with aq NaHCO$_3$ (10%), dried (MgSO$_4$) and the solvent was removed. Purification by chromatography (SiO$_2$, CH$_2$Cl$_2$/methanol/heptane, 4:1:5) gave 3-fluoro-N-[2-amino-4-(4-methyl-1-piperazinyl)-phenyl]benzenesulfonamide (0.140 g, 57%). MS (posES-FIA) m/z=found: 365.2, calcd: 364.14; Anal. (C$_{17}$H$_{22}$ClFN$_4$O$_2$S.3H$_2$O) C, H, N, S. The reaction produced a small amount of bis-sulfonylated compound 3-fluoro-N-[2-{[(3-fluorophenyl)sulfonyl]amino}-4-(4-methyl-1-piperazinyl)-phenyl]be (0.010 g, 3%). The products were transformed into their HCl-salt before analysis; MS (posES-FIA) m/z=found. 523.5, calcd: 522.12. Anal. (C$_{23}$H$_{25}$ClF$_2$N$_4$O$_4$S$_2$) C, H, N, S.

Example 4

N-{4-(4-methyl-1-piperazinyl)-2-[(8-quinolinylsulfonyl)amino]phenyl}-8-quinolinesulfonamide hydrochloride (Scheme 3)

8-Quinolinesulfonyl chloride (0.185 g, 0.81 mmol) was added to a solution of 2-amino-5-(4-methyl-1(0.168 g, 0.81 mmol) and pyridine (514 mL, 6.39 mmol) in $CH_2Cl_2$. After 1 h at room temperature the mixture was washed with aq $NaHCO_3$ (10%), dried ($MgSO_4$) and the solvent was removed. Purification by chromatography ($SiO_2$, $CH_2Cl_2$/MeOH/heptane, 4:1:5) gave N-2-amino-4-(4-methyl-1-piperazinyl)-]-phenyl-8-quinolinesulfonamide (0.110 g, 35%). MS (posES-FIA) m/z=found: 384.2, calcd 383.48; %); Anal. ($C_{19}H_{22}ClN_5O_2S$ $3H_2O$) C, H, N, S and a small amount of the bis-sulfonylated N-{4-(4-methyl-1-piperazinyl)-2-](8-quinolinylsulfonyl)amino]phenyl}-8-quinolinesulfonamide (0.070 g, 15%). The product was converted to HCl salt before analysis; MS (posES-FIA) m/z=found: 589.6, calcd: 588.16; Anal. ($C_{29}H_{29}ClN_6O_4S_2 2H_2$C, H, N.

Synthesis According to Scheme 2

Scheme 2, Method 3: General R1=Me

Intermediate 7

Synthesis of N-(5-fluoro-2-nitrophenyl)benzenesulfonamide (Scheme 2, Method 3)

Benzenesulfonamide (3.14 g, 20 mmol) was dissolved in DMF (100 mL) and NaH (60% in oil, 40 mmol, 1.60 g) was added. The reaction was stirred until the gas evolution ceased. 2,4-Difluoronitrobenzene (18 mmol, 2.9 g, 2 mL) was added and the reaction mixture was stirred over night at 35° C. The reaction mixture was poured into HCl (1M aq, 100 mL) and extracted with toluene (25 mL×5). The organic phase was dried ($MgSO_4$) and concentrated and re-crystallized from EtOH to give a first crop of 3.75 g of a yellow solid. A second crop of 0.20 g was collected from the EtOH remains. Yield 3.95 g, 13.3 mmol (74%). MS (posES-FIA) m/z=found: 296; Calc: 296.0.

Intermediate 8

Synthesis of N-[5-(4-methyl-1-piperazinyl)-2-nitrophenyl]benzenesulfonamide (Scheme 2, Method 3)

N-(5-fluoro-2-nitrophenyl)benzenesulfonamide (2×0.50 g, 1.688 mmol) was treated with N-methyl-piperazine (2×4.65 g, 45.6 mmol) and put in two pyrex tubes and sealed. Each tube was put in a LabWell MW-10 microwave oven for 2 min at 50W. The reaction mixtures were combined and poured into 0.5 M NaOH (aq) and extracted with $CH_2Cl_2$, dried ($MgSO_4$) and concentrated to give 0.99 g, (2.63 mmol) in 78% yield as a yellow solid. Anal ($C_{17}H_{20}N_4O_4S$) C, H, N, S; MS (posES-FIA) m/z=found: 377.4; Calcd: 376.12.

Example 5

N-[2-Chloro-4-({4-(4-methyl-1-piperazinyl)-2-[(phenylsulfonyl)amino]-anilino}sulfonyl) phenyl]acetamide hydrochloride (Scheme 2, Method 3)

N-[5-(4-Methyl-1-piperazinyl)-2-nitrophenyl]benzenesulfonamide (0.600 g, 1.59 mmol) was dissolved in THF (20 mL) followed by the addition of Raney-Ni (0.322 g, in ethanol) and hydrazine hydrate (0.100 g, 2.0 mmol). The reaction mixture was stirred for 1 h, filtered through Celite and concentrated. The residue was dissolved in pyridine (12 mL) and divided in 12 equal parts. To one part was added 3-cloro-4-N-acetamido-benzenesulfonylchloride (52 mg, 0.20 mmol). The reaction mixture was stirred over night, poured into petroleum ether to form a precipitate that was collected by centrifugation. The precipitate purified by column chromatography ($SiO_2$, $CH_2Cl_2$/MeOH 95:5 to 9:1). The pure product was dissolved in MeOH and treated with HCl/diethyl ether to give 9.6 mg, (12% yield). MS (posES-FIA) m/z=found: 578.4; Calcd: 577.12.

Example 6

3,4-Dimethoxy-N-{4-(4-methyl-1-piperazinyl)-2-[(phenylsulfonyl)-amino]phenyl}benzenesulfonamide hydrochloride (Scheme 2, Method 3)

N-[5-(4-Methyl-1-piperazinyl)-2-nitrophenyl]benzenesulfonamide (0.600 g, 1.59 mmol) was dissolved in THF (20 mL) followed by the addition of Raney-Ni (0.322 g, in ethanol) and hydrazine hydrate (0.100 g, 2.0 mmol). The reaction mixture was stirred for 1 h, filtered through Celite and concentrated. The residue was dissolved in pyridine (12 mL) and divided in 12 equal parts. To one part was added 3,4-dimethoxy-bensenesulfonylchloride (47 mg, 0.20 mmol). The reaction mixture was stirred overnight, poured into petroleum ether to form a precipitate that was collected by centrifugation. The precipitate was purified by column chromatography ($SiO_2$, $CH_2Cl_2$/MeOH 95:5 to 9:1). The pure product was dissolved in MeOH and treated with HCl/diethyl ether to give 34.5 mg, (45% yield). MS (posES-FIA) m/z=found: 547.4; Calcd: 546.16.

Example 7

3-Methoxy-4-methyl-N-{4-(4-methyl-1-piperazinyl)-2-[(phenylsulfonyl)-amino]phenyl}benzenesulfonamide hydrochloride (Scheme 2, Method 3)

N-[5-(4-Methyl-1-piperazinyl)-2-nitrophenyl]benzenesulfonamide (0.600 g, 1.59 mmol) was dissolved in THF (20 mL) followed by the addition of Raney-Ni (0.322 g, in ethanol) and hydrazine hydrate (0.100 g, 2.0 mmol). The reaction mixture was stirred for 1 h, filtered through Celite and concentrated. The residue was dissolved in pyridine (12 mL) and divided in 12 equal parts. To one part was added 2-methoxy-4-methyl-benzenesulfonylchloride (44 mg, 0.20 mmol). The reaction mixture was stirred overnight, poured into petroleum ether to form a precipitate that was collected by centrifugation. The precipitate was purified by purified by column chromatography ($SiO_2$, $CH_2Cl_2$/MeOH 95:5 to 9:1). The pure product was dissolved in MeOH and treated with HCl/diethyl ether to give 21 mg, (28% yield). MS (posES-FIA) m/z=found: 530.1635; Calcd: 530.1658.

Intermediate 9

Synthesis of N-(5-fluoro-2-nitrophenyl)methanesulfonamide (Scheme 2, Method 3)

Methylsulfonamide (2.421 g, 25.4 mmol) was dissolved in DMF (100 mL) and NaH (60% in oil, 1.00 g, 25 mmol)

was added. The reaction stirred for 1 h and added to a stirred solution of 2,4-difluoronitrobenzene (4.372 g, 27.5 mmol) in DMF (20 mL). The reaction mixture was stirred for 2 h, poured into a mixture (1:1) of brine and 1M HCl, and extracted with toluene. The organic phase was dried (MgSO$_4$), and concentrated to give a solid that was crystallized from toluene/petroleum ether. The flask tipped over and some material was lost, to give 1.32 g, 5.64 mmol in 22% yield. MS (posES-FIA) m/z=found: 234; Calcd: 234.01; Anal (C$_7$ H$_7$ F N$_2$ O$_4$ S), C, H, N, S.

Intermediate 10

Synthesis of N-[5-(4-methyl-1-piperazinyl)-2-nitrophenyl]-methanesulfonamide (Scheme 2, Method 3).

N-(5-fluoro-2-nitrophenyl)methanesulfonamide (1.33 g, 5.68 mmol) was dissolved in DMF (10 mL) and N-methylpiperazine (2.00 g, 20 mmol) was added. The reaction mixture was stirred at 20° C. for 1 h, and then heated with a heat gun for 5 min to reach boiling of DMF (150° C.), then left stirring for another hour. The reaction mixture was then poured into brine and extracted with toluene (10 mL×2), EtOAc (20 mL×2) and CH$_2$Cl$_2$ (20 mL×2), NaHCO$_3$ was then added to the water phase and then the water phase was extracted with CH$_2$Cl$_2$ (20 mL×2). The organic phases were combined and dried (MgSO$_4$) and concentrated to give a semi solid. EtOH was added and left over night and then filtered off to give 1.503 g (4.78 mmol) in 84% yield. MS (posES-FIA) m/z=found: 315; Calc M=314.10; Anal (C$_{12}$ H$_{18}$ N$_4$ O$_4$ S), C, H, N, S.

Example 8

4-Methyl-N-{4-(4-methyl-1-piperazinyl)-2-[(methylsulfonyl)amino]-phenyl}benzenesulfonamide hydrochloride (Scheme 2, Method 3)

N-[5-(4-methyl-1-piperazinyl)-2-nitrophenyl]-methanesulfonamide (0.45 g, 1.43 mmol) was dissolved in THF (10 mL) followed by the addition of Raney-Ni (0.15 g in ethanol) and hydrazine hydrate (78 mg, 1.56 mmol). The reaction was stirred for 1 h. Another aliquot of hydrazine hydrate (20 μL) was added and the reaction stirred for another hour, filtered through Celite and concentrated to give 0.42 g that was used to the next step without further purification. The material was dissolved in DMF (10 mL) and divided into 3 equal parts. To one part was added p-toluene sulfonyl chloride (0.095 g, 0.5 mmol) and the reaction was stirred for 1 h and poured into a mixture of petroleum ether/acetone (30 mL/10 mL) to give a precipitate. Additional product was found in the solution and added to the precipitate. The product was isolated by chromatography (SiO$_2$, CH$_2$Cl$_2$/MeOH 9:1) to give 0.063 g, (28% yield). MS (posES-FIA) m/z=found: 38.1393; Calcd: 438.1395.

Example 9

3,4-Dimethoxy-N-{4-(4-methyl-1-piperazinyl)-2-[(methylsulfonyl)amino]-phenyl}benzenesulfonamide hydrochloride (Scheme 2, Method 3)

N-[5-(4-methyl-1-piperazinyl)-2-nitrophenyl]-methanesulfonamide (0.45 g, 1.43 mmol) was dissolved in THF (10 mL) and Raney-Ni (0.15 g in ethanol) was added followed by hydrazine hydrate (78 mg, 1.56 mmol) and the reaction was stirred for 1 h. Additional hydrazine hydrate (20 μL) was added and the reaction stirred for another hour, filtered through Celite and concentrated to give 0.42 g of product that was used without further purification. The material was dissolved in DMF (10 mL) and divided into 3 equal parts. To one part was added 3,4 dimethoxybenzenesulfonylchloride (0.118 g, 0.5 mmol) and the reaction was stirred for 1 h, poured into a mixture of petroleum ether/acetone (30 mL/10 mL) to form a precipitate. Additional product was found in the solution and was added to the precipitate. The product was isolated by chromatography (SiO$_2$, CH$_2$Cl$_2$/MeOH 9:1) to give 0.064 g, (26% yield). MS (posES-FIA) m/z=found: 484.1436; Calcd: 484.1450.

Example 10

3-Cyano-N-{4-(4-methyl-1-piperazinyl)-2-[(methylsulfonyl)amino]-phenyl}benzenesulfonamide hydrochloride (Scheme 2, Method 3)

N-[5-(4-methyl-1-piperazinyl)-2-nitrophenyl]-methanesulfonamide (0.45 g, 1.43 mmol) was dissolved in THF (10 mL) and Rayney-Ni (0.15 g in ethanol) was added followed by hydrazine hydrate (78 mg, 1.56 mmol) and the reaction was stirred for 1 h. Additional hydrazine hydrate (20 μL) was added and the reaction stirred for another hour, filtered through Celite and concentrated to give 0.42 g of product that was used without further purifications. The material was dissolved in DMF (10 mL) and divided into 3 equal parts. To one part was added 3-cyanobenzenesulfonylchloride (0.101 g, 0.5 mmol) and the reaction was stirred for 1 h. poured into a mixture of petroleum ether/acetone (30 mL/10 mL) to form a precipitate. Additional product was found in the solution and was combined to the precipitate. The product was isolated by chromatography (SiO$_2$, CH$_2$Cl$_2$/MeOH 9:1) to give 0.0301 g, (13% yield). MS (posES-FIA) m/z=found: 449.1177; Calcd: 449.1191.

Scheme 2, Method 4: General R1=H

N-(2-amino-5-(4-boc-1-piperazinyl)-phenyl)-benzenesulfonamide

A mixture of N-(2-nitro-3-fluorophenyl)-benzenesulfonamide (4.68 g, 15.7 mmol), Boc-piperazine (3.5 g, 18.9 mmol) and K$_2$CO$_3$ (3.8 g, 27.8 mmol) in DMF was stirred at 70° C. for 24 h. The mixture was filtered and purified by column chromatography (SiO$_2$, CH$_2$Cl$_2$/MeOH/heptane/ NH$_3$ 4:1:5:0.2%) to give 2.0 g of desired product. $^1$H-NMR δ 7.98 (d, 1H), 7.89–7.84 (m, 2H), 7.63–7.50 (m, 3H), 7.00 (d, 1H), 6.68 (dd, 1H), 3.59–3.45 (m, 8H), 1.49 (s, 9H); MS (posES-FIA) m/z=found: 485.0 (M$^+$+Na$^+$). The product (1.85 g, 4.00 mmol) was dissolved in EtOH:THF (4:1) followed by addition of Raney-Ni and hydrazine (1.0 mL, 20 mmol). The reaction was stirred at room temperature for 3 h until the yellow color disappeared. Filtration through wet Celite, followed by removal of the solvent afforded 1.26 g of N-(2-amino-5-(4-tert-butoxycarbonyl-1-piperazinyl)-phenyl)-benzenesulfonamide which was used without further purification.

To a solution of N-{2-amino-5-(4-t-butyloxycarbonyl-piperazinyl)-phenyl}benzenesulfonamide (79 mg, 0.184 mmol) and pyridine (131 μL, 1.6 mmol) in CH$_2$Cl$_2$ (7 mL) and different sulfonylchlorides (0.239 mmol) was added. After 2 h at room temperature the solvent was removed.

Purification by chromatography (SiO$_2$, CH$_2$Cl$_2$/MeOH/heptane, 4:1:15) followed by Boc-deprotection which was achieved by dissolving the residue in small amount of MeOH and adding HCl/ether. The mixture was left at room temperature for 0.5 h after which the solvent was removed. Re-crystallization (MeOH/ether) afforded the final products respectively.

Example 11

N-{4-(1-Piperazinyl)-2-[(phenylsulfonyl)amino]phenyl}-1-naphthalenesulfonamide hydrochloride (Scheme 2, Method 4)

N-{4-(1-Piperazinyl)-2-[(phenylsulfonyl)amino]phenyl}-1-naphthalenesulfonamide was synthesized from N-{2-amino-5-(4-t-butyloxycarbonyl-piperazinyl)-phenyl}benzenesulfonamide and 1-naphthalenesulfonylchloride (54 mg, 0.239 mmol) according to general method 3 to give 40 mg of a purple solid. MS (posES-FIA) m/z=Found: 523.2; Calcd 523.14; $^1$H NMR δ 8.83–8.59 (m, 1H), 8.10 (d, 1H), 8.02–7.97 (m, 1H), 7.90 (d, 1H), 7.74–7.38 (m, 8H), 6.69–6.65 (m, 1H), 6.39-6.34 (m, 2H), 3.3

Example 12

5-(Dimethylamino)-N-{4-(1-piperazinyl)-2-[(phenylsulfonyl)amino]phenyl}-1-naphthalenesulfonamide hydrochloride (Scheme 2, Method 4)

5-(Dimethylamino)-N-{4-(1-piperazinyl)-2-[(phenylsulfonyl)amino]phenyl}-1-naphthalenesulfonamide was synthesized from N-{2-amino-5-(4-t-butyloxycarbonyl-piperazinyl)-phenyl}benzenesulfonamide and dansylchloride (64 mg, 0.239 mmol) according to general method 3 to give 60 mg of a purple solid. MS (posES-FIA) m/z=Found: 566.3; Calcd: 566.18; $^1$H NMR δ 8.84 (d, 1H), 8.60 (d, 1H), 8.08 (d, 2H), 7.84–7.47 (m, 7H), 6.70 (d, 1H), 6.56–6.53 (m, 1H), 6.41–6.37 (m, 1H), 3.46 (s, 6H), 3.25–3.12 (m, 8H),

Example 13

N-[2-[(Phenylsulfonyl)amino]-4-(1-piperazinyl)phenyl]-8-quinolinesulfonamide hydrochloride (Scheme 2, Method 4)

N-[2-[(Phenylsulfonyl)amino]-4-(1-piperazinyl)phenyl]-8-quinolinesulfonamide was synthesized from N-{2-amino-5-(4-t-butyloxycarbonyl-piperazinyl)-phenyl}benzenesulfonamide and 8-quinolinesulfonylchloride (54 mg, 0.239 mmol) according to general method 3 to give 50 mg of a purple solid. MS (posES-FIA) m/z=Found: 524.2; Calcd: 524.13; $^1$H NMR δ 9.34 (dd, 1H), 8.79 (dd, 1H), 8.37 (dd, 1H), 8.25 (dd, 1H), 7.92 (dd, 1H), 7.73 (t, 1H), 7.57–7.40 (m, 5H), 7.17 (d, 1H), 6.71 (dd, 1H), 6.14 (d, 1H), 3.23–3.08 (m, 8H).

Example 14

2,4,6-Trimethyl-N-[2-[(phenylsulfonyl)amino]-4-(1-piperazinyl)phenyl] benzenesulfonamide hydrochloride (Scheme 2, Method 4)

2,4,6-Trimethyl-N-[2-[(phenylsulfonyl)amino]-4-(1-piperazinyl)phenyl] benzenesulfonamide was synthesized from N-{2-amino-5-(4-t-butyloxycarbonyl-piperazinyl)-phenyl}benzenesulfonamide and 2-mesitylenesulfonylchloride (52 mg, 0.239 mmol) according to general method 3 to give 50 mg of a purple solid. MS (posES-FIA) m/z=Found: 515.3; Calcd 515.17; $^1$H-NMR δ 7.74 (d, 2H); 7.63–7.46 (m, 3H), 6.92 (s, 2H), 6.74–6.55 (m, 3H), 3.27–3.20 (m, 8H), 2.35 (s, 6H), 2.25 (s, 3H).

Example 15

4-Methyl-N-[2-[(phenylsulfonyl)amino]-4-(1-piperazinyl)phenyl] benzenesulfonamide hydrochloride (Scheme 2, Method 4)

4-Methyl-N-[2-[(phenylsulfonyl)amino]-4-(1-piperazinyl)phenyl]benzenesulfonamide was synthesized from N-{2-amino-5-(4-t-butyloxycarbonyl-piperazinyl)-phenyl}benzenesulfonamide and p-toluenesulfonylchloride (46 mg, 0.239 mmol) according to general method 3 to give 70 mg of a purple solid. MS (posES-FIA) m/z=Found: 487.2; Calcd: 487.14; $^1$H-NMR δ 7.73–7.45 (m, 7H), 7.26 (d, 2H), 6.74 (s, 1H), 6.62–6.60 (m, 2H), 3.69 (app t, 2H), 3.39 (app t, 2H), 3.29–3.74 (m, 4H), 2.38 (s, 3H).

Example 16

N-[2-({[(E)-2-Phenylethenyl]sulfonyl}amino)-5-(1-piperazinyl)phenyl] benzenesulfonamide hydrochloride (Scheme 2, Method 4)

N-[2-({[(E)-2-Phenylethenyl]sulfonyl}amino)-5-(1-piperazinyl)phenyl]benzenesulfonamide was synthesized from N-{2-amino-5-(4-t-butyloxycarbonyl-piperazinyl)-phenyl}benzenesulfonamide and β-styrenesulfonylchloride (48 mg, 0.239 mmol according to general method 3 to give before Boc-deprotection 160 mg of a purple solid. MS (posES-FIA) m/z=Found: 499.2; Calcd 499.14; $^1$H-NMR δ 8.26 (d, 1H), 8.04 (d, 1H), 7.75–7.38 (m, 8H), 7.22 (d, 1H, J=15.4 Hz), 7.16 (d, 1H), 6.97 (d, 1H), J=15.4 Hz), 6.78 (dd, 1H), 6.68 (d, 1H), 3.68 (app t, 2H), 3.39 (app t, 2H), 3.28–3.21 (m, 4H).

Example 17

2,5-Dimethoxy-N-[2-[(phenylsulfonyl)amino]-4-(1-piperazinyl)phenyl] benzenesulfonamide hydrochloride (Scheme 2, Method 4)

2,5-Dimethoxy-N-[2-[(phenylsulfonyl)amino]-4-(1-piperazinyl)phenyl] benzenesulfonamide was synthesized from of N-{2-amino-5-(4-t-butyloxycarbonyl-piperazinyl)-phenyl}benzenesulfonamide and 2,5-dimethoxybenzenesulfonylchloride (57 mg, 0.239 mmol) according to general method 3 to give 60 mg of a purple solid. MS (posES-FIA) m/z=Found: 533.1; Calcd: 533.14; $^1$H-NMR δ 7.68–7.48 (m, 5H), 7.16–7.05 (m, 4H), 6.69 (dd, 1H), 6.42 (d, 1H), 4.03 (s, 3H), 3.69 (s, 3H), 3.26–3.10 (m, 8H).

Example 18

2-Methyl-N-[2-[(phenylsulfonyl)amino]-4-(1-piperazinyl)phenyl] benzenesulfonamide hydrochloride (Scheme 2, Method 4)

2-Methyl-N-[2-[(phenylsulfonyl)amino]-4-(1-piperazinyl)phenyl]benzenesulfonamide was synthesized from N-{2-amino-5-(4-t-butyloxycarbonyl-piperazinyl)-phenyl}benzenesulfonamide and o-toluenesulfonylchloride (46 mg, 0.239 mmol) according to general method 3 to give before Boc-deprotection 160 mg of a purple solid. MS (posES-FIA) m/z=Found: 487.1; Calcd 487.14; $^1$H-NMR δ 7.74–7.16 (m, 8H), 6.78–6.52 (m, 4H), 3.27–3.16 (m, 8H), 2.58 (s, 3H).

Example 19

2,4-Difluoro-N-[2-[(phenylsulfonyl)amino]-4-(1-piperazinyl)phenyl] benzenesulfonamide hydrochloride (Scheme 2, Method 4)

2,4-Difluoro-N-[2-[(phenylsulfonyl)amino]-4-(1-piperazinyl)phenyl] benzenesulfonamide was synthesized from N-{2-amino-5-(4-t-butyloxycarbonyl-piperazinyl)-phenyl}benzenesulfonamide and 2,4-difluorobenzenesulfonylchloride (94 mg, 0.455 mmol) according to general method 3 to give before Boc-deprotection 160 mg of a purple solid. MS (posES-FIA) m/z=Found: 509.1; Calcd 509.11; $^1$H-NMR δ 77.71–7.46 (m, 6H), 7.25–7.17 (m, 1H), 7.03–6.96 (m, 2H), 6.72 (dd, 1H), 6.44 (d, 1H), 3.20–3.16 (m, 8H).

Example 20

4-Butoxy-N-[2-[(phenylsulfonyl)amino]-4-(1-piperazinyl)phenyl] benzenesulfonamide hydrochloride (Scheme 2, Method 4)

4-Butoxy-N-[2-[(phenylsulfonyl)amino]-4-(1-piperazinyl)phenyl]benzenesulfonamide was synthesized from N-{2-amino-5-(4-t-butyloxycarbonyl-piperazinyl)-phenyl}benzenesulfonamide and 4-n-butoxybenzenesulfonylchloride (59 mg, 0.239 mmol) according to general method 3 to give 70 mg of a purple solid. MS (posES-FIA) m/z=Found: 545.2; Calcd 545.18; $^1$H-NMR δ 7.73–7.45 (m, 7H), 6.95–6.91 (m, 2H), 6.72–6.70 (m, 1H), 4.00 (t, 2H), 3.29–3.24 (m, 8H), 1.79–1.70 (m, 2H), 1.55–1.43 (m, 2H), 0.97 (t, 3H).

Example 21

3,5-Dimethyl-N-[2-[(phenylsulfonyl)amino]-4-(1-piperazinyl)phenyl]-4-isoxazolesulfonamide hydrochloride (Scheme 2, Method 4)

3,5-Dimethyl-N-[2-[(phenylsulfonyl)amino]-4-(1-piperazinyl)phenyl]-4-isoxazolesulfonamide was synthesized from N-{2-amino-5-(4-t-butyloxycarbonyl-piperazinyl)-phenyl}benzenesulfonamide and 3,5-dimethylisoxazolesulfonylchloride (47 mg, 0.239 mmol) according to general method 3 to give 70 mg of a purple solid. MS (posES-FIA) m/z=Found: 492.1; Calcd 492.13; $^1$H-NMR δ 7.72–7.47 (m, 5H), 6.98 (d, 1H), 6.80 (dd, 1H), 6.50 (d, 1H), 3.28–3.22 (m, 8H), 2.22 (s, 3H), 2.11 (s, 3H).

Example 22

5-Fluoro-2-methyl-N-[2-[(phenylsulfonyl)amino]-4-(1-piperazinyl)phenyl]benzenesulfonamide (Scheme 2, Method 4)

5-Fluoro-2-methyl-N-[2-[(phenylsulfonyl)amino]-4-(1-piperazinyl)-phenyl]benzenesulfonamide was synthesized from N-{2-amino-5-(4-t-butyloxycarbonyl-piperazinyl)-phenyl}benzenesulfonamide and 5-fluoro-2-methylbenzenesulfonylchloride (50 mg, 0.239 mmol) according to general method 3 to give 60 mg of a purple solid. MS (posES-FIA) m/z=Found: 505.2; Calcd 505.13; $^1$H-NMR δ 7.73–7.17 (m, 8H), 6.83 (d, 1H), 6.68 (dd, 1H), 6.50 (dd, 1H), 3.27–3.17 (m, 8H), 2.55 (s, 3H).

Example 23

4-(Methylsulfonyl)-N-[2-[(phenylsulfonyl)amino]-4-(1-piperazinyl)phenyl]-benzenesulfonamide hydrochloride (Scheme 2, Method 4)

4-(Methylsulfonyl)-N-[2-[(phenylsulfonyl)amino]-4-(1-piperazinyl)-phenyl]benzenesulfonamide was synthesized from N-{2-amino-5-(4-t-butyloxycarbonyl-piperazinyl)-phenyl}benzenesulfonamide and 4-methylsulfonylbenzenesulfonylchloride (61 mg, 0.455 mmol) according to general method 3 to give 70 mg of a purple solid. MS (posES-FIA) m/z=Found: 551.2; Calcd: 551.10.

Example 24

2-(Methylsulfonyl)-N-[2-[(phenylsulfonyl)amino]-4-(1-piperazinyl)phenyl] benzenesulfonamide hydrochloride (Scheme 2, Method 4)

2-(Methylsulfonyl)-N-[2-[(phenylsulfonyl)amino]-4-(1-piperazinyl)phenyl]benzenesulfonamide was synthesized from N-{2-amino-5-(4-t-butyloxycarbonyl-piperazinyl)-phenyl}benzenesulfonamide and 2-methylsulfonylbenzenesulfonylchloride (61 mg, 0.239 mmol) according to general method 3 to give 70 mg of a purple solid. MS (posES-FIA) m/z=Found: 551.2; Calcd: 551.10; $^1$H-NMR δ 8.36–7.46 (m, 9H), 6.95 (d, 1H), 6.68 (dd, 1H), 6.46 (d, 1H), 3.47 (s, 3H), 3.28–3.17 (m, 8H).

Example 25

2-Methoxy-4-methyl-N-[2-[(phenylsulfonyl)amino]-4-(1-piperazinyl)phenyl] benzenesulfonamide hydrochloride (Scheme 2, Method 4)

2-Methoxy-4-methyl-N-[2-[(phenylsulfonyl)amino]-4-(1-piperazinyl)phenyl] benzenesulfonamide was synthesized from N-{2-amino-5-(4-t-butyloxycarbonyl-piperazinyl)-phenyl}benzenesulfonamide and 2-methoxy-4-methylbenzenesulfonylchloride (53 mg, 0.239 mmol) according to general method 3 to give 80 mg of a purple solid. MS (posES-FIA) m/z=Found: 517.2; Calcd 517.15; $^1$H NMR δ 7.67–7.37 (m, 6H), 7.10–7.04 (m, 2H), 6.97–6.74 (m, 2H), 6.30 (d, 1H), 4.06 (s, 3H), 3.26–3.09 (m, 8H), 2.37 (s, 3H).

Example 26

4-Methoxy-2-methyl-N-[2-[(phenylsulfonyl)amino]-4-(1-piperazinyl)phenyl] benzenesulfonamide hydrochloride (Scheme 2, Method 4)

4-Methoxy-2-methyl-N-[2-[(phenylsulfonyl)amino]-4-(1-piperazinyl)phenyl] benzenesulfonamide was synthesized from N-{2-amino-5-(4-t-butyloxycarbonyl-piperazinyl)-phenyl}benzenesulfonamide and 2-methyl-4-trifluoromethoxybenzenesulfonylchloride (53 mg, 0.455 mmol) according to general method 3 to give before Boc-deprotection 70 mg of a purple solid. MS (posES-FIA) m/z=Found: 571.2; Calcd 571.12; $^1$H NMR δ 773–7.09 (m, 8H), 6.86 (d, 1H), 6.69 (dd, 1H), 6.48 (d, 1H), 3.29–3.17 (m, 8H), 2.62 (s, 3H).

Example 27

N-{4-(homopiperazinyl)-2-[(phenylsulfonyl)amino]phenyl}benzenesulfonamide hydrochloride (Scheme 1, Method 2)

Benzenesulfonyl chloride (0.088 g, 0.50 mmol) was added to a solution of 2-amino-5-(4 -t-butyloxycarbonyl-homopiperazin-1-yl)aniline(0.153 g, 0.50 mmol) and pyridine (514 mL, 6.39 mmol) in DCM. After 1 h at r.t. the mixture was washed with NaHCO$_3$ (10%) dried (MgSO$_4$) and the solvent was removed. Purification by column chromatography (CH$_2$Cl$_2$/MeOH/heptane, 4:1:15) gave a mixture of N-{2-amino-4-[4-t-butyloxycarbonyl-homopiperazin-1-yl-]phenyl}benzenesulfonamide and of the bis-sulphonylated N-{4-[4-t-butyloxycarbonyl]homopiperazinyl)-2-[(phenylsulfonyl)amino]phenyl}benzenesulfonamide (0.150 g, 86%). Boc-deprotection was achieved by dissolving the mixture in MeOH and adding HCl/ether. The mixture was let at r.t. for 0.5 h. Purification by preparative HPLC gave N-{4-(homopiperazinyl)-2-[(phenylsulfonyl)amino]phenyl}benzenesulfonamide hydrochloride; Anal. (C$_{23}$H$_{27}$ClN$_4$O$_4$S$_2$) C, H, N, S; M+487.4 Calcd 486.14. And N-{4-(homopiperazinyl)-2-[(phenylsulfonyl)amino]phenyl}benzenesulfonamide hydrochloride; Anal. (C$_{17}$H$_{23}$ClN$_4$O$_2$S) C, H, N, S; M+347.5 Calcd 346.15.

Example 28

N-(4-(1,4-diazepan-1-yl)-2-{[(3-fluorophenyl)sulfonyl]amino} phenyl)-3-fluorobenzenesulfonamide hydrochloride (Scheme 1, Method 2)

The compound was prepared from 2-amino-5-(4-t-butyloxycarbonyl-1-homopiperazinyl)aniline and 3-flouroben-zenesulfonyl chloride. Purification by column chromatography (CH$_2$Cl$_2$/MeOH/heptane, 4:1:15) gave a mixture of N-{2-amino-4-[4-t-butyloxycarbonyl-homopiperazin-1-yl-]phenyl}3fluorobenzenesulfonamide and N-{4-[4-t-butyloxycarbonyl] homopiperazinyl)-2-[(3-flourophenylsulfonyl)amino]phenyl}-3-fluorobenzenesulfonamide (0.180 g, 73%). Boc-deprotection was achieved by dissolving the mixture in small amount of MeOH and adding HCl/ether. The mixture was let at r.t. for 0.5 h. Purification by preparative HPLC gave N-(4-(1,4-diazepan-1-yl)-2-{[(3-fluorophenyl)sulfonyl]amino}phenyl)-3-fluorobenzenesulfonamide hydrochloride Anal. (C$_{23}$H$_{27}$ClN$_4$O$_4$S$_2$) C, H, N, S.; M+524.4 Calcd 522.12.

Example 29

N-{4-(1,4-diazepan-1-yl)-2-[ethyl(phenylsulfonyl)amino]phenyl}benzenesulfonamide hydrochloride (Scheme 1, Method 2)

A solution of benzenesulfonyl chloride (0.579 mL, 4.53 mmol) in DCM (2.0 mL) was added to tert-butyl 4-[4-amino-3-(ethylamino)phenyl]-1,4-diazepane-1-carboxylate (0.605 g, 1.81 mmol), and pyridine (1.02 mL, 12.67 mmol) in DCM (8.0 mL). The mixture was stirred at room temperature for 16 hours and then concentrated. The crude intermediate was purified by column chromatography on silica using CHCl$_3$/10% MeOH+0.4% NH$_3$. Deprotection using HCl-ether/EtOAc gave 0.365 g of the crude product as a HCl-salt. Purification on a reversed phase preperative HPLC gave 94 mg of the product as an acetic acid salt which was converted to the HCl salt and recrystallized from MeOH/Ether: yield 64 mg. $^1$H NMR (DMSO-d6) δ 9.05 (br s, 2H), 8.66 (s, 1H), 7.89–7.85 (m, 2H), 7.75–7.55 (m, 8H), 7.07 (app d, J=9.1 Hz, 1H), 6.71–6.66 (m, 1H), 5.70 (app d, J=3.2 Hz, 1H), 3.50–3.32 (m, partly obscured by HDO signal, 4H), 3.18–3.14 (m, 2H), 3.05–2.90 (m, 2H), 1.90–1.81 (m, 2H), 0.67 (tr, J=7.2 Hz, 3H); Ms (posES-FIA) m/z 515 (M+H)

Method 4 (Scheme 2)

Diverse sulfonylchlorides were added to a solution of N-{2-amino-5-(4-t-butyloxycarbonyl-1,4-diazepan-1-yl) and pyridine (135 μL, 1.7 mmol) in DCM (7 mL),. After 1 h at r.t. the solvent was removed. Purification by column chromatography (CH2Cl$_2$/MeOH/Heptane, 4:1:15) followed by Boc-deprotection which was achieved by dissolving the residue in small amount of MeOH and adding HCl/ether. The mixture was left at r.t. for 0.5 h after which the solvent was removed. Recrystallization (MeOH/ether) afforded the final product.

Example 30

N-{5-(1,4-diazepan-1-yl)-2-[(methylsulfonyl)amino]phenyl}benzenesulfonamide (Scheme 2, Method 4)

N-{5-(1,4-diazepan-1-yl)-2-[(methylsulfonyl)amino]phenyl}benzenesulfonamide was synthesized from N-{2-amino-5-(4-t-butyloxycarbonyl-1,4-diazepan-1-yl)-phenyl}benzenesulfonamide (0.075 g, 0.16 mmol) and, methanesulfonyl chloride (0.017 mL, 0.22 mmole) to give 41.6 mg of a light purple solid; Anal. (C$_{24}$H$_{27}$ClN$_4$O$_3$S× 1.3H$_2$O) C, H, N, S.; M+425.4 Calcd 425.12.

Example 31

N-{5-(1,4-diazepan-1-yl)-2-[(ethylsulfonyl)amino]phenyl}benzenesulfonamide hydrochloride (Scheme 2, Method 4)

N-{5-(1,4-diazepan-1-yl)-2-[(ethylsulfonyl)amino]phenyl}benzenesulfonamide hydrochloride was synthesized from N-{2-amino-5-(4-t-butyloxycarbonyl-1,4-diazepan-1-yl)-phenyl}benzenesulfonamide (0.085 g, 0.19 mmol) and ethanesulfonyl chloride (0.032 μL, 0.25 mmol) to give 29.1 mg of a light purple solid; Anal. (C$_{24}$H$_{27}$ClN$_4$O$_3$S×0.75H$_2$O H, N, S.; M+439.4 Calcd 439.14.

Example 32

N-{4-(1,4-diazepan-1-yl)-2-[(phenylsulfonyl)amino]phenyl}[1,1'-biphenyl]-4-sulfonamide hydrochloride (Scheme 2, Method 4)

N-{4-(1,4-diazepan-1-yl)-2-[(phenylsulfonyl)amino]phenyl}[1,1'-biphenyl]-4-sulfonamide hydrochloride was synthesized from N-{2-amino-5-(4-t-butyloxycarbonyl-1,4-diazepan-1-yl)-phenyl}benzenesulfonamide (0.081 g, 0.18 mmol) and, 1,1'-biphenyl-4-sulfonyl chloride (0.059 g, 0.24 mmol) to give 42.9 mg of a light purple solid; Anal. (C$_{24}$H$_{27}$ClN$_4$O$_3$S) C, H, N, S.; M+563.5 Calcd 563.17.

Example 33

N-(2,1,3-benzoxadiazol-4-yl)-4-(1,4-diazepan-1-yl)-2-[(phenylsulfonyl)amino]benzenesulfonamide hydrochloride (Scheme 2, Method 4)

N-(2,1,3-benzoxadiazol-4-yl)-4-(1,4-diazepan-1-yl)-2-[(phenylsulfonyl)amino]benzenesulfonamide hydrochloride was synthesized from N-{2-amino-5-(4-t-butyloxycarbonyl-1,4-diazepan-1-yl)-phenyl}benzenesulfonamide (0.072 g, 0.16 mmol) and 2,1,3-benzoxadiazol-4-yl sulfonyl chloride (0.072 g, 0.21 mmol) to give 38.0 mg of a light purple solid; M+1 537.2 Calcd 537.15; $^1$HNMR δ 8.21 (d, 1H), 7.80 (d, 1H), 7.68–7.46 (m, 6H), 6.92 (d, 1H), 6.49 (dd, 1H), 6.12 (d, 1H), 3.57 (app t, 2H), 3.34 (app t, 2H), 3.17 (app t, 2H), 3.11 (app t, 2H), 2.03–1.95 (m, 2H).

Example 34

N-{4-(1,4-diazepan-1-yl)-2-[(phenylsulfonyl)amino]phenyl}-2-naphthalenesulfonamide hydrochloride (Scheme 2, Method 4)

N-{4-(1,4-diazepan-1-yl)-2-[(phenylsulfonyl)amino]phenyl}-2-naphthalenesulfonamide hydrochloride was synthesized from N-{2-amino-5-(4-t-butyloxycarbonyl-1,4-diazepan-1-yl)-phenyl}benzenesulfonamide (0.084 g, 0.19 mmol) and, 2-naphtylsulfonyl chloride (0.055 mL, 0.24 mmol) to give 67.8 mg of a light purple solid; Anal. ($C_{24}H_{27}ClN_4O_3S$) C, H, N, S; M+529.2 Calcd 529.12.

Example 35

N-{4-(1,4-diazepan-1-yl)-2-[(methylsulfonyl)amino]phenyl}benzenesulfonamide hydrochloride (Scheme 2, Method 4)

Benzenesulfonylchloride (0.233 g, 1.8 mmol) was added to a solution of N-{5-(4-t-butyloxycarbonyl-1,4-diazepan-1-yl)-2-amino]phenyl}methanesulfonamide (0.540 g, 1.4 mmol) and pyridine (0.995 mL, 12.6 mmol) in DCM (40 mL) After 2 h at rt the solvent was removed. Purification by column chromatography (DCM/MeOH/heptane 4:1:5) gave 580 mg (79%) of a light purple solid. Boc-deprotection was carried out by dissolving the compound in small amount of MeOH and adding HCl/ether. The solvent was removed and the product was recrystrallized from MeOH/ether. M+1 425.2 Calcd 425.12

Example 36

N-{4-(1,4-diazepan-1-yl)-2-[methyl(methylsulfonyl)amino]phenyl}benzenesulfonamide hydrochloride (Scheme 2, Method 4)

MeI (45 μL, 0.72 mmol) was added to a mixture of N-{4-(4-t-butyloxycarbonyl-1,4-diazepan-1-yl)-2-[(methylsulfonyl)amino]phenyl}benzenesulfonamide (0.189 g, 0.36 mmol) and $K_2CO_3$ (0.124, 0.90 mmol) in acetone (25 mL). The mixture was stirred at r.t. for 2 h, filtered and the solvent was removed. Columnchromatography (DCM/MeOH/Heptane 4:1:15) gave 110 mg of N-{4-(4-t-butyloxycarbonyl1,4-diazepan-1-yl)-2-[methyl(methylsulfonyl) amino]-phenyl}benzenesulfonamide and 20 mg of N-{4-(4-t-butyloxycarbonyl 1,4-diazepan-1-yl)-2-[(methylsulfonyl)amino]phenyl}-N-methyl-benzenesulfonamide. Boc-deprotection was carried out by dissolving the compounds in small amount of MeOH and adding HCl/ether. The solvent was removed and the products were recrystallized from MeOH/ether. N-{4-(1,4-diazepan-1-yl)-2-[methyl(methylsulfonyl)amino]phenyl}benzenesulfonamide hydrochloride M+1 439.2 Calcd 439.14.

Example 37

N-{4-(1,4-diazepan-1-yl)-2-[(methylsulfonyl)amino]phenyl}-N-methylbenzenesulfonamide hydrochloride (Scheme 2, Method 4)

MeI (45 μL, 0.72 mmol) was added to a mixture of N-{4-(4-t-butyloxycarbonyl-1,4-diazepan-1-yl)-2-[(methylsulfonyl)amino]phenyl}benzenesulfonamide (0.189 g, 0.36 mmol) and $K_2CO_3$ (0.124, 0.90 mmol) in acetone (25 mL). The mixture was stirred at r.t. for 2 h, filtered and the solvent was removed. Purification by column chromatography (DCM/MeOH/Heptane 4:1:15) gave 110 mg of N-{4-(4-t-butyloxycarbonyl1,4-diazepan-1-yl)-2-[methyl (methylsulfonyl)amino]phenyl}benzenesulfonamide and 20 mg of N-{4-(4-t-butyloxycarbonyl 1,4-diazepan-1-yl)-2-[(methylsulfonyl)amino]phenyl}-N-methyl benzenesulfonamide. Boc-deprotection was carried out by dissolving the compounds in small amount of MeOH and adding HCl/ether. The solvent was removed and the products were recrystrallized from MeOH/ether. N-{4-(1,4-diazepan-1-yl)-2-[(methylsulfonyl)amino]-phenyl}-N-methylbenzenesulfonamide hydrochloride M+1 439.2 Calcd 439.14.

Example 38

N-{4-(1,4-diazepan-1-yl)-2-[methyl(phenylsulfonyl)amino]phenyl}benzenesulfonamide hydrochloride (Scheme 2, Method 4)

MeI (45 μL, 0.72 mmol) was added to a mixture of N-{4-(4-t-butyloxycarbonyl-1,4-diazepan-1-yl)-2-[(phenylsulfonyl)amino]phenyl}benzenesulfonamide (0.189 g, 0.36 mmol) and $K_2CO_3$ (0.124, 0.90 mmol) in acetone (25 mL). The mixture was stirred at r.t. for 2 h, filtered and the solvent was removed. Purification by column chromatography (DCM/MeOH/heptane 4:1:15) gave N-{4-(4-t-butyloxycarbonyl-1,4-diazepan-1-yl)-2-[methyl(phenylsulfonyl)-amino]phenyl}benzenesulfonamide as a colourless oil. Boc-deprotection was carried out by dissolving the compound in small amount of MeOH and adding HCl/ether. The solvent was removed and the residue was recrystrallized from MeOH/ether to give 62.7 mg of product M+1 501.3 Calcd 501.16.

Scheme 3

To a solution of N-{2-amino-5-(4-t-butyloxycarbonyl-1,4-diazepan-1-yl)-phenyl}methanesulfonamide (134 mg, 0.35 mmol) and pyridine (250 μL, 3.14 mmole) in DCM (7 mL), the sulfonylchloride (0.455 mmol) was added. After 2 h at r.t. the solvent was removed. Purification by column chromatography ($CH_2Cl_2$/MeOH/Heptane, 4:1:15) followed by Boc-deprotection which was achieved by dissolving the residue in small amount of MeOH and adding HCl/ether. The mixture was left at r.t. for 0.5 h after which the solvent was removed. Recrystallization (MeOH/ether) afforded the final product.

Example 39

N-{4-(1,4-diazepan-1-yl)-2-[(methylsulfonyl)amino]phenyl}-1-naphthalenesulfonamide hydrochloride (Scheme 3)

The compound was synthesized from N-{2-amino-5-(4-t-butyloxycarbonyl-1,4-diazepan-1-yl)-phenyl}methanesulfonamide and 1-napthalenesufonylchloride (103 mg, 0.455 mmol) to give before Boc-deprotection 150 mg of a purple solid. M+1 475.1 Calcd 474.14.

Example 40

N-{4-(1,4-diazepan-1-yl)-2-[(methylsulfonyl)amino]phenyl}-2-naphthalenesulfonamide hydrochloride (Scheme 3)

The compound was synthesized from N-{2-amino-5-(4-t-butyloxycarbonyl-1,4-diazepan-1-yl)-phenyl}methanesulfonamide and 2-napthalenesufonylchloride (103 mg, 0.455 mmol) to give before Boc-deprotection 120 mg of a purple solid. M+1 475.1 Calcd 474.14.

Example 41

N-{4-(1,4-diazepan-1-yl)-2-[(methylsulfonyl)amino]phenyl}-4-fluorobenzenesulfonamide hydrochloride (Scheme 3)

The compound was synthesized from N-{2-amino-5-(4-t-butyloxycarbonyl-1,4-diazepan-1-yl)-phenyl}methanesulfonamide and 4-fluorobenzenesulfonylchloride (89 mg, 0.455 mmol) to give before Boc-deprotection 170 mg of a purple solid. M+1 443.1 Calcd 443.11.

Example 42

N-{4-(1,4-diazepan-1-yl)-2-[(methylsulfonyl)amino]phenyl}-4-nitrobenzenesulfonamide hydrochloride (Scheme 3)

The compound was synthesized from N-{2-amino-5-(4-t-butyloxycarbonyl-1,4-diazepan-1-yl)-phenyl}methanesulfonamide and 4-nitrobenzenesulfonylchloride (101 mg, 0.455 mmol) according to general method 3 to give before Boc-deprotection 118 mg of a purple solid. M+1 470.1 Calcd 470.11.

Example 43

N-{4-(1,4-diazepan-1-yl)-2-[(methylsulfonyl)amino]phenyl}-3-(trifluoromethyl)-benzenesulfonamide hydrochloride (Scheme 3)

The compound was synthesized from N-{2-amino-5-(4-t-butyloxycarbonyl-1,4-diazepan-1-yl)-phenyl}methanesulfonamide and 3-trifluoromethylbenzenesulfonylchloride (111 mg, 0.455 mmol) to give before Boc-deprotection 145 mg of a purple solid. M+1 493.1 Calcd 493.11.

Example 44

N-{4-(1,4-diazepan-1-yl)-2-[(methylsulfonyl)amino]phenyl}-2-methylbenzenesulfonamide hydrochloride (Scheme 3)

The compound was synthesized from N-{2-amino-5-(4-t-butyloxycarbonyl-1,4-diazepan-1-yl)-phenyl}methanesulfonamide and o-toluenesulfonylchloride (87 mg, 0.455 mmol) to give before Boc-deprotection 175 mg of a purple solid. M+1 439.2 Calcd 438.14.

Example 45

N-{4-(1,4-diazepan-1-yl)-2-[(methylsulfonyl)amino]phenyl}-4-(trifluoromethoxy)-benzenesulfonamide hydrochloride (Scheme 3)

The compound was synthesized from N-{2-amino-5-(4-t-butyloxycarbonyl-1,4-diazepan-1-yl)-phenyl}methanesulfonamide and 4-trifluoromethoxybenzenesulfonylchloride (119 mg, 0.455 mmol) give 140 mg as a purple solid. M+1 509.1 Calcd 509.11.

Example 46

N-{4-(1,4-diazepan-1-yl)-2-[(methylsulfonyl)amino]phenyl}-3,5-dimethyl-4-isoxazolesulfonamide hydrochloride (Scheme 3)

The compound was synthesized from N-{2-amino-5-(4-t-butyloxycarbonyl-1,4-diazepan-1-yl)-phenyl}methanesulfonamide and 3,5-dimethylisoxazole-4-sulfonylchloride (89 mg, 0.455 mmol) 3 to give 120 mg of as purple solid. M+1 444.2 Calcd 444.13.

Example 47

N-{4-(1,4-diazepan-1-yl)-2-[(methylsulfonyl)amino]phenyl}-3-methoxybenzene-sulfonamide hydrochloride (Scheme 3)

The compound was synthesized from N-{2-amino-5-(4-t-butyloxycarbonyl-1,4-diazepan-1-yl)-phenyl}methanesulfonamide and 3-methoxybenzenesulfonylchloride (94 mg, 0.455 mmol) to give 160 mg as a purple solid. M+1 455.2 Calcd 455.13.

Intermediate 11 tert-Butyl 4-{4-{[(4-methylphenyl)sulfonyl]amino}-3-[(methylsulfonyl)amino]phenyl}-1,4-diazepane-1-carboxylate (Scheme 2, Method 4)

tert-Butyl 4-{4-nitro-3-[(methylsulfonyl)amino]phenyl}-1,4-diazepane-1-carboxylate (1 g, 2.4 mmol) was dissolved in THF (20 mL) and methanol (2 mL). Raney nickel (0.2 g) was added followed by hydrazine hydrate (0.2 mL). Nitrogen was evolved and the mixture stirred for 1 hour. The reaction was shown to be incomplete by tlc ($CH_2Cl_2$. MeOH 9:1) so a further 0.1 mL of hydrazine hydrate was added. After a further hour, the reaction mixture was absorbed onto a bed of silica gel and eluted with $CH_2Cl_2$:MeOH:$NH_4$OH (9:1:0.01 150 mL). The solvent was removed by evaporation, toluene (100 mL) was added and evaporated to remove any water and hydrazine. The crude amine (0.9 g) was dissolved in acetonitrile (20 mL). To this solution under nitrogen was added dimethylaminopyridine (0.32 g) and toluenesulfonyl chloride (0.51 g) and the mixture stirred for 3 hours. The solution was poured into water (100 mL) and extracted with ethyl acetate (30 mL). The organic extract was washed with water, dried over $MgSO_4$ and evaporated to give 0.83 g of crude product which was purified by flash chromatography (EtOAc:Petrol 1:1). Yield 0.53 g (41%) $^1$H NMR (400 MHz, $CDCl_3$) δ 1.38, 1.40 (2s, 9 H), 1.91 (m, J=6.11 Hz, 2 H), 2.44 (s, 3 H), 3 H), 3.16–3.33 (m, 2 H), 3.46–3.57 (m, 6 H), 6.02 (s, 1 H), 6.21 (ab, J=9.03 Hz, 1H), 6.30 (ab, J=9.03 Hz, 1 H), 6.97 (d, J=2.69 Hz, 1 H), 7.27 (ab, J=8.55 Hz, 2 H), 7.33, 7.36 (2s, 1 H), 7.57 (ab, J=8.06 Hz, 2 H); MS (ESI+) for $C_{24}H_{34}N_4O_6S_2$ m/z 561.1800 (M+)$^+$ (Calculated 561.1817).

Example 48

N-{4-(1,4-diazepan-1-yl)-2-[(methylsulfonyl)amino] phenyl}-4-methylbenzenesulfonamide hydrochloride (PHA 516123A)

tert-Butyl 4-{4-{[(4-methylphenyl)sulfonyl]amino}-3-[(methylsulfonyl)amino]phenyl}-1,4-diazepane-1-carboxylate (0.5 g) was dissolved in methanol (15 mL). A solution of HCl in ethyl acetate (1N, 25 mL) was added and the mixture stirred for 2 hours. Ether (200 mL) was added and the mixture stirred for 3 hours to allow full precipitation. The product was collected by filtration, washed with ether and dried. Yield 0.43 g (98%) $^1$H NMR (400 MHz, DMSO-$d_6$) δ 2.03 (m, 2 H), 2.36 (s, 3 H), 2.9 (s, 3H), 3.02–3.09 (br m, 2 H), 3.11–3.19 (br m, 2 H), 3.41 (br t, J=7.08 Hz, 2 H), 3.63 (br m, 2 H), 6.46 (d ab, J=2.8 Hz, 8.8 Hz, 1 H), 6.62 (ab, J=8.8 Hz, 1 H), 6.71 (d, J=2.8 Hz, 1 H), 7.36 (ab, J=8.3 Hz, 2 H), 7.58 (ab, J=8.3 Hz, 2 H), 8.39 (s, 1 H), 9.2 (br, 2 H). 9.8 (s, 1 H), MS (ESI+) for $C_{19}H_{27}N_4O_4S_2$ m/z 439.148 (M+H)$^+$ (Calculated 439.1474).

Intermediate 12

N-ethyl-N-(5-fluoro-2-nitrophenyl)methanesulfonamide (Scheme 2, Method 4)

N-ethyl-methanesulfonamide (Mijs et al. J. Chem. Soc. Chem. Com. 1972 p412) (5 g 40.6 mmol) was added to a suspension of sodium hydride (1.9 g, 55% in mineral oil) in anhydrous DMF (100 mL) under nitrogen. The mixture was warmed to 55° C. for one hour and 2,4-difluoronitrobenzene (4.4 mL) was added dropwise. The reaction was stirred at 60° C. overnight, poured into water (500 mL) and the product extracted into $CH_2Cl_2$ (5×100 mL). The organic extracts were washed with water, dried over $MgSO_4$ and evaporated to give an oily product. The remaining DMF was removed by trituration with petrol. The crude product was purified by flash chromatography (ethyl acetate:petrol 1:1) to yield the desired product which was recrystallised from ethanol. Yield 3.5 g (33%). Calculated N % 10.68 C % 41.22 S % 12.23 H % 4.23; Found N % 10.68 C % 41.39 S % 12.22 H % 4.17.

Intermediate 13 tert-Butyl 4-{3-[ethyl(methylsulfonyl)amino]-4-nitrophenyl}-1,4-diazepane-1-carboxylate (Scheme 2, Method 4)

N-Ethyl-N-(5-fluoro-2-nitrophenyl)methanesulfonamide (3.2 g, 12.2 mmol), tert-butyl 1-homopiperazinecarboxylate (2.5 g) and potassium carbonate (2 g) were heated together in DMSO at 50° C. for 5 hours. The solution was allowed to cool and poured into 500 mL of water. The solid product was collected by filtration, washed with water and dried. The product was purified by flash chromatography (ethyl acetate: petrol 1:1). Yield 2.6 g (48%) $^1$H NMR (400 MHz, $CDCl_3$) δ 1.16 (t, J=7.33 Hz, 3 H), 1.39 (s, 9 H), 2.0 (br, 2 H), 2.99 (s, 3 H), 3.2 (br, 2 H), 3.54–3.75 (br, 8 H), 6.65 (br d, J=9.3 Hz, 1 H), 6.67 (d,j=2.93 Hz, 1 H), 8.1 (d, J=9.3 Hz, 1 H); MS (ESI+) for $C_{19}H_{30}N_4O_6S$ m/z 442 (M$^+$).

Preparation of N-{4-(1,4-diazepan-1-yl)-2-[ethyl (methylsulfonyl)amino]phenyl}-sulfonamides tert-Butyl 4-{3-[ethyl(methylsulfonyl)amino]-4-nitrophenyl}-1,4-diazepane-1-carboxylate (2.5 g, 5.7 mmol) was dissolved in THF (50 mL) and methanol (5 mL). Raney nickel (0.5 g) was added followed by hydrazine hydrate (0.5 mL). Nitrogen was evolved and the mixture stirred for 1 hour. The reaction mixture was absorbed onto a bed of silica gel and eluted with $CH_2Cl_2$:MeOH:$NH_4OH$ (9:1:0.01 200 mL). The solvent was removed by evaporation, toluene (200 mL) was added and evaporated to remove any water and hydrazine. The crude amine (2.15 g) was dissolved in acetonitrile (50 mL) with dimethylaminopyridine (0.8 g). This solution was divided into three portions. To each portion was added a sulfonyl chloride (2.2 mmol) and the mixtures were stirred overnight at 40° C. The reactions were worked up by adding to water (150 mL), extracting the product into ethyl acetate, washing with water, drying over $MgSO_4$ and evaporating. Each of the crude boc protected products was purified by flash chromatography (ethyl acetate:petrol 1:1). They were then deprotected directly by dissolving in methanol (10 mL), adding a solution of HCl in ethyl acetate (1N, 50 mL) and stirring for 2 hours. The products were precipitated with ether (500 mL), collected by filtration and dried under vacuum. The products obtained were:

Example 49

N-{4-(1,4-diazepan-1-yl)-2-[ethyl(methylsulfonyl)-amino]phenyl}-4-methylbenzenesulfonamide hydrochloride (Scheme 2, Method 4)

Was obtained from toluene sulfonyl chloride: Yield 0.36 g $^1$H NMR (400 MHz, DMSO-$d_6$) δ 0.79 (t, J=7.08 Hz, 3 H), 2.04 (m, 2 H), 2.37 (s, 3 H), 3.07 (s, 3 H), 3.02–3.12 (br, 2 H), 3.12–3.20 (br, 2 H), 3.45 (t, J=5.85 Hz, 2 H), 3.50 (q,J=7.08 Hz, 2 H), 3.67 (br, 2 H), 6.65–6.73 (m, 2 H), 6.94 (d, J=9.03 Hz, 1 H), 7.38 (ab Hz, 2 H), 7.70 (ab, J=8.06 Hz, 2 H), 8.52 (s, 1 H), 9.2 (br s, 2 H) MS (ESI+) for $C_{21}H_{30}N_4O_4S_2$ m/z 466.1722 M$^+$ (Calc 466.1708).

Example 50

N-{4-(1,4-diazepan-1-yl)-2-[ethyl-(methylsulfonyl)-amino]phenyl}-3,4-dimethoxybenzenesulfonamide hydrochloride (Scheme 2, Method 4)

Was obtained from 3,4-dimethoxybenzenesulfonyl chloride: Yield 0.43 g $^1$H NMR (400 MHz, DMSO-$d_6$) δ 0.81 (t, J=7.08 Hz, 3 H), 2.05 (m, 2 H), 3.08 (s, 3 H), 3.03–3.11 (br, 2 H), 3.11–3.19 (br, 2 H), 3.45 (t, J=6.10 Hz, 2 H), 3.52 (q, J=7.08 Hz, 2 H), 3.68 (br t, J=5.13 Hz, 2 H), 3.77 (s, 3 H), 3.81 (s, 3 H), 6.66–6.74 (m, 2 H), 6.97 (d, J=8.79 Hz, 1 H), 7.09 (d, J=8.55 Hz, 1 H), 7.33–7.4 (m, 2 H), 8.49 (s, 1 H), 9.3 (br s, 2 H) MS (ESI+) for $C_{22}H_{32}N_4O_6S_2$ m/z 512.1759 M$^+$ (Calc 512.1763).

Example 51

N-{4-(1,4-diazepan-1-yl)-2-[ethyl(methyl-sulfonyl)amino]phenyl}-8-quinolinesulfonamide hydrochloride (Scheme 2, Method 4)

Was obtained from 8-quinoline sulfonyl chloride: Yield 0.46 g $^1$H NMR (400 MHz, DMSO-d$_6$) δ 0.17 (t, J=7.08 Hz, 3 H), 2.06 (m, 2 H), 2.93 (s, 3 H), 3.0–3.2 (m, 6 H), 3.47 (t, J=5.86 Hz, 2 H), 3.70 (t, J=5.12 Hz, 2 H), 6.59 (m, 1 H), 6.77 (d m, J=9 Hz, 1 H), 7.31 (d, J=9 Hz, 1 H), 7.65–7.75 (m, 2 H), 8.24 (d, J=7.32 Hz, 1 H), 8.29 (d, J=9.5 Hz, 1 H), 8.55 (dd, J=8.55, 1.71 Hz, 1 H), 9 (br, 1 H), 9.09 (dd, J=4.16, 1.71 Hz, 1 H), 9.3 (br, 2 H); MS (ESI+) for C$_{23}$H$_{29}$N$_5$O$_4$S$_2$ m/z 503.1667 M$^+$ (Calc 503. 1661).

Intermediate 14

N-(5-fluoro-2-nitrophenyl)methanesulfonamide (Scheme 2, Method 4)

2,4-di-Nitrobenzene (5.5 mL, 50 mmol), methanesulfonamide (4.75 g, 50 mmol) and potassium carbonate (10 g) were stirred together in DMSO (100 mL) at 80° C. overnight. Water (300 mL) was added followed by hydrochloric acid (1N, 300 mL). The solid product was collected by filtration, washed with water and dried. Yield 9.57 g (82%) $^1$H NMR (400 MHz, CDCl$_3$) δ 3.2 (s, 3 H), 6.92 (m, 1 H), 7.64 (dd, J=10.5, 2.7 Hz, 1 H), 8.34 (dd, J=9.5, 5.6 Hz, 1 H), 10.0 (brs, 1 H); MS (ESI+) for C$_7$H$_7$FN$_2$O$_4$S m/z 234 M$^+$.

Intermediate 15

N-(5-Fluoro-2-nitrophenyl)-N-methylmethanesulfonamide (Scheme 2, Method 4)

N-(5-fluoro-2-nitrophenyl)methanesulfonamide compound (5 g, 21 mmol), methyl iodide (3 mL) and potassium carbonate (10 g) were stirred together in DMSO (100 mL) at 80° C. overnight. The reaction was not complete and a further 1 mL of methyl iodide was added. After a further 24 hours at 80° C., water (1000 mL) was added. The solution was decanted from a small amount of sticky residue. The product crystallized out from the aqueous solution (48 hours) and was collected by filtration, washed with water and dried. Yield 3.3 g (63%); $^1$H NMR (400 MHz, CDCl$_3$) δ 3.04 (s, 3H), 3.30 (s, 3H), 7.20 (m, 1H), 7.31 (dd, J=8.54, 2.68 Hz, 1H), 8.0 (dd, J=9.3, 5.6 Hz, 1H); MS (ESI+) for C$_8$H$_9$FN$_2$O$_4$S m/z 248 M$^+$.

Intermediate 16 tert-Butyl-4-{3-[methyl(methylsulfonyl)amino]-4-nitrophenyl}-1,4-diazepane-1-carboxylate (Scheme 2, Method 4)

N-(5-Fluoro-2-nitrophenyl)-N-methylmethanesulfonamide (3.1 g, 12.5 mmol), tert-butyl 1-homopiperazinecarboxylate (2.5 g) and potassium carbonate (2 g) were heated together in DMSO (50 mL) at 80° C. overnight. The solution was allowed to cool and poured into 500 mL of water. The solid product was collected by filtration, washed with water and dried. Yield 4.6 g (86%); $^1$H NMR (400 MHz, CDCl$_3$) δ 1.41 (s, 9H), 2.0 (br s, 2H), 3.01 (s, 3H), 3.28 (s, 3H), 3.3–3.8 (br, 8H), 6.64 (d, J=8.1 Hz, 1H), 6.74 (d, J=4.8 Hz, 1H), 8.09 (d, J=8.1 Hz, 1H); MS (ESI+) for C$_{18}$H$_{28}$N$_4$O$_6$S m/z 428.1709 (M$^+$) (calc. 428.173).

Preparation of N-{4-(1,4-diazepan-1-yl)-2-[methyl(methylsulfonyl)amino]phenyl}-sulfonamides tert-Butyl-4-{3-[methyl(methylsulfonyl)amino]-4-nitrophenyl}-1,4-diazepane-1-carboxylate (2.5 g, 5.7 mmol) was dissolved in THF (50 mL) and methanol (5 mL). Raney nickel (0.5 g) was added followed by hydrazine hydrate (0.5 mL). Nitrogen was evolved and the mixture stirred for 1 hour. The reaction mixture was absorbed onto a bed of silica gel and eluted with CH$_2$Cl$_2$:MeOH:NH$_4$OH (9:1:0.01 200 mL). The solvent was removed by evaporation, toluene (200 mL) was added and evaporated to remove any water and hydrazine. The crude amine (2.36 g) was dissolved in acetonitrile (50 mL) with dimethylaminopyridine (0.8 g). This solution was divided into six portions. To three of these portions was added a sulfonyl chloride (1.1 mmol) and the mixtures were stirred overnight at 40° C. The reactions were worked up by adding ethyl acetate (50 mL), washing with brine and water, drying over MgSO$_4$ and evaporating. Each of the crude boc protected products was purified by flash chromatography (ethyl acetate:petrol 2:1). They were then deprotected directly by dissolving in methanol (10 mL), adding a solution of HCl in ethyl acetate (1N, 50 mL) and stirring for 2 hours. The products were precipitated with ether (500 mL), collected by filtration and dried under vacuum.

The products obtained were:

Example 52

N-{4-(1,4-diazepan-1-yl)-2-[methyl(methylsulfonyl)-amino]phenyl}-4-methylbenzenesulfonamide hydrochloride (Scheme 2, Method 4)

Was obtained from toluene sulfonyl chloride: Yield 0.18 g $^1$H NMR (400 MHz, DMSO-d$_6$) δ 2.04 (br m, 2H), 2.36 (s, 3H), 2.72 (s, 3H), 3.05 (s, 3H), 3.1–3.4 (m, 4H), 3.46 (t, J=6.34 Hz, 2H), 3.70 (t, J=4.88 Hz, 2H), 6.69 (d, J=2.7 Hz, 1H), 6.72 (s, 1H), 6.95 (d, J=8.78 Hz, 1H), 7.36 (ab, J=8.54 Hz, 2H), 7.57 (ab, J=8.54 Hz, 2H), 8.39 (s, 1H), 9.24 (brs, 2H); MS (ESI+) for C$_{20}$H$_{28}$N$_4$O$_4$S$_2$ m/z 452.1545 M$^+$ (Calc. 452.1552).

Example 53

N-{4-(1,4-diazepan-1-yl)-2-[methyl-(methyl-sulfonyl)amino]phenyl}-naphthalene-2-sulfonamide hydrochloride (Scheme 2, Method 4)

Was obtained from 2-naphthalenesulfonyl chloride: Yield 0.09 g $^1$H NMR (400 MHz, DMSO-d$_6$) δ 2.0 (br m, 2H), 2.66 (s, 3H), 3.05 (s, 3H), 3.0–3.4 (m, 4H), 3.43 (t, J=7.08 Hz, 2H), 3.66 (br t, J=5.1 Hz, 2H), 6.65 (dd, J=9.0, 2.9 Hz, 1H), 6.68 (s, 1H), 6.90 (d, J=9.0 Hz, 1H), 7.65 (q, J=8.0 Hz, 1H), 7.68 (q, J=8.3 Hz, 1H), 7.8 (d, J=6.8 Hz, 1H), 8.04 (d, J=7.8 Hz, 1H), 8.12 (t, J=8.8 Hz, 2H), 8.32 (s, 1H), 8.68 (s, 1H), 9.2 (br, 2H); MS (ESI+) for C$_{23}$H$_{28}$N$_4$O$_4$S$_2$ m/z 488.1529 M$^+$ (Calc. 488.1552).

Example 54

N-{4-(1,4-diazepan-1-yl)-2-[methyl(methylsulfonyl)amino]phenyl}-5-(2-pyridinyl)-2-thiophenesulfonamide hydrochloride (Scheme 2, Method 4)

Was obtained from 5-(2-pyridinyl)thiophene-2-sulfonyl chloride: Yield 0.12 g $^1$H NMR (400 MHz, DMSO-d$_6$) δ

2.05 (br m, 2H), 2.90 (s, 3H), 3.07 (s, 3H), 3.1–3.4 (m, 4H), 3.48 (t, J=6.1 Hz, 2H), 3.71 (m, 2H), 6.75 (dd, J=9.0, 2.7 Hz, 1H), 6.78 (s, 1H), 7.03 (d, J=8.8 Hz, 1H), 7.39 (dd, J=7.6, 4.2 Hz, 1H), 7.50 (d, J=4.2 Hz, 1H), 7.84 (d, J=3.9 Hz, 1H), 7.91 (td, J=7.6, 1.7 Hz, 1H), 8.03 (d, J=7.8 Hz, 1H), 8.56 (d, J=4.9 Hz, 1H), 8.81 (s, 1H), 9.3 (br, 2H); MS (ESI+) for $C_{22}H_{27}N_5O_4S_3$ m/z 521.1200 M+ (Calc. 521.1225).

Scheme 3

To a solution of N-{2-amino-5-(4-t-butyloxycarbonyl-1,4-diazepan-1-yl)-phenyl}benzenesulfonamide (92.5 mg, 0.207 mmol) and pyridine (131 μL, 1.6 mmol) in DCM (7 mL), the sulfonylchloride (0.27 mmol) was added. After 2 h at r.t. the solvent was removed. Purification by columnchromatography ($CH_2Cl_2$/MeOH/Heptane, 4:1:15) followed by Boc-deprotection which was achieved by dissolving the residue in small amount of MeOH and adding HCl/ether. The mixture was left at r.t. for 0.5 h after which the solvent was removed. Recrystallization (MeOH/ether) afforded the final product.

Example 55

N-{4-(1,4-diazepan-1-yl)-2-[(phenylsulfonyl)amino]phenyl}-1-naphthalenesulfonamide hydrochloride (Scheme 3)

The compound was synthesized from of N-{2-amino-5-(4-t-butyloxycarbonyl-1,4-diazepan-1-yl)-phenyl}benzenesulfonamide and 1-naphthalenesulfonylchloride (61 mg, 0.27 mmol) to give 56 mg as purple solid. M+1 537.2 Calcd 537.15; $^1$HNMR δ 8.67–8.64 (m, 1H), 8.10 (d, 1H), 8.02–7.98 (m, 1H), 7.89 (dd, 1H), 7.77–7.38 (m, 8H), 6.46 (d, 1H), 6.26 (d, 1H), 6.14 (dd, 1H), 3.54 (app t, 2H), 3.36–3.31 (m, 2H), 3.17 (app t, 2H), 2.05–1.96 (m, 2H).

Example 56

N-{4-(1,4-diazepan-1-yl)-2-[(phenylsulfonyl)amino]phenyl}-5-(dimethylamino)-1-naphthalenesulfonamide hydrochloride (Scheme 3)

The compound was synthesized from of N-{2-amino-5-(4-t-butyloxycarbonyl-1,4-diazepan-1-yl)-henyl}benzenesulfonamide and dansylchloride (73 mg, 0.27 mmol) to give 51 mg AS purple solid. M+1 580.3 Calcd 580.20; $^1$HNMR δ 8.86 (d, 1H), 8.62 (d, 1H), 8.08–7.46 (m, 9H), 6.64 (d, 1H), 6.32 (dd, 1H), 6.14 (d, 1H), 3.53 (app t, 2H), 3.45 (s, 6H), 3.16–3.06 (m, 4H), 2.03–1.95 (m, 2H).

Example 57

N-{4-(1,4-diazepan-1-yl)-2-[(phenylsulfonyl)amino]phenyl}-8-quinolinesulfonamide hydrochloride (Scheme 3)

The compound was synthesized from of N-{2-amino-5-(4-t-butyloxycarbonyl-1,4-diazepan-1-yl)-phenyl}benzenesulfonamide and 8-quinolinesulfonylchloride (61 mg, 0.27 mmol) to give 34 mg of a purple solid. M+1 538.2 Calcd 538.15.

Example 58

N-{4-(1,4-diazepan-1-yl)-2-[(phenylsulfonyl)amino]phenyl}-2,4,6-trimethylbenzenesulfonamide hydrochloride (Scheme 3)

The compound was synthesized from of N-{2-amino-5-(4-t-butyloxycarbonyl-1,4-diazepan-1-yl)-phenyl}benzenesulfonamide and 2-mesitylenesulfonylchloride (59 mg, 0.27 mmol) to give 56 mg as purple solid. M+1 529.3 Calcd 529.70; $^1$HNMR δ 7.80–7.47 (m, 5H), 6.93 (s br, 2H), 6.64 (d, 1H), 6.46–6.39 (m, 2H), 3.60 (app t, 2H), 3.39 (app t, 2H), 3.21 (app t, 2H), 3.12 (app t, 2H), 2.36 (s, 6H), 2.26 (s, 3H), 2.08–2.00 (m, 2H).

Example 59

N-{4-(1,4-diazepan-1-yl)-2-[(phenylsulfonyl)amino]phenyl}-4-methylbenzenesulfonamide hydrochloride (Scheme 3)

The compound was synthesized from of N-{2-amino-5-(4-t-butyloxycarbonyl-1,4-diazepan-1-yl)-phenyl}benzenesulfonamide and p-toluenesulfonylchloride (51 mg, 0.27 mmol) to give 22 mg as purple solid. M+1 501.3 Calcd 501.15; $^1$HNMR δ 7.77–7.26 (m, 9H), 6.54 (d, 1H), 6.50 (d, 1H), 6.40 (dd, 1H), 3.63 (app t, 2H), 3.42 (app t, 2H), 3.25 (app t, 2H), 3.16 (app t, 2H), 2.38 (s, 3H), 2.11–2.03 (m, 2H).

Example 60

N-[5-(1,4-diazepan-1-yl)-2-({[(E)-2-phenylethenyl]sulfonyl}amino)phenyl]benzenesulfonamide hydrochloride (Scheme 3)

The compound was synthesized from of N-{2-amino-5-(4-t-butyloxycarbonyl-1,4-diazepan-1-yl)-phenyl}benzenesulfonamide and beta-styrenesulfonylchloride (55 mg, 0.27 mmol) to give before Boc-deprotection 12 mg as purple solid. M+1 513.6 Calcd 512.15; $^1$HNMR δ 7.78–7.38 (m, 10H), 7.20 (d, 1H), J=15.4 Hz), 7.10 (d, 1H), 6.98 (d, 1H), J=15.4 Hz), 6.56 (dd, 1H), 6.44 (d, 1H), 3.62 (app t, 2H), 3.41 (app t, 2H), 3.23 (app t, 2H), 3.15 (app t, 2H), 2.09–2.01 (m, 2H).

Example 61

N-{4-(1,4-diazepan-1-yl)-2-[(phenylsulfonyl)amino]phenyl}-2,5-dimethoxybenzenesulfonamide hydrochloride (Scheme 3)

The compound was synthesized from of N-{2-amino-5-(4-t-butyloxycarbonyl-1,4-diazepan-1-yl)-phenyl}benzenesulfonamide and 2,5-dimethoxybenzenesulfonylchloride (64 mg, 0.27 mmol) to give 14 mg as purple solid. M+1 547.3 Calcd 547.16; $^1$HNMR δ 7.71–7.00 (m, 9H), 6.48 (dd, 1H), 6.16 (d, 1H), 4.04 (s, 3H), 3.68 (s, 3H), 3.56 (app t, 2H), 3.33 (app t, 2H), 3.17 (app t, 2H), 3.11 (app t, 2H), 2.03–1.95 (m, 2H).

Example 62

N-{4-(1,4-diazepan-1-yl)-2-[(phenylsulfonyl)amino]phenyl}-2-methylbenzenesulfonamide hydrochloride (Scheme 3)

The compound was synthesized from of N-{2-amino-5-(4-t-butyloxycarbonyl-1,4-diazepan-1-yl)-phenyl}benzenesulfonamide and o-toluenesulfonylchloride (51 mg, 0.269 mmol) to give 18 mg as purple solid. M+1

501.3 Calcd 501.15; $^1$HNMR δ 7.78–7.17 (m, 9H), 6.68–6.35 (m, 3H), 3.63–3.10 (m, 8H), 2.59 (s, 3H), 2.09–2.01 (m, 2H).

Example 63

4-Butoxy-N-{4-(1,4-diazepan-1-yl)-2-[(phenylsulfonyl)amino]phenyl}-benzenesulfonamide hydrochloride (Scheme 3)

The compound was synthesized from of N-{2-amino-5-(4-t-butyloxycarbonyl-1,4-diazepan-1-yl)-phenyl}benzenesulfonamide and 4-n-butoxybenzenesulfonylchloride (67 mg, 0.269 mmol) to give 27 mg as purple solid. M+1 559.4 Calcd 559.20; $^1$HNMR δ 7.77–7.47 (m, 7H), 6.96–6.93 (m, 2H), 6.55 (d, 1H), 6.52 (d, 1H), 6.41 (d, 1H), 4.01 (t, 2H), 3.63 (app t, 2H), 3.43 (app t, 2H), 3.25 (app t, 2H), 3.17 (app t, 2H), 2.11–2.03 (m, 2H), 1.80–1.71 (m, 2H), 1.53–1.45 (m, 2H), 0.98 (t, 3H).

Example 64

N-{4-(1,4-diazepan-1-yl)-2-[(phenylsulfonyl)amino]phenyl}-3,5-dimethyl-4-isoxazolesulfonamide hydrochloride (Scheme 3)

The compound was synthesized from of N-{2-amino-5-(4-t-butyloxycarbonyl-1,4-diazepan-1-yl)-phenyl}benzenesulfonamide and 3,5-dimethylisoxazolesulfonylchloride (53 mg, 0.269 mmol) to give 32 mg as purple solid. M+1 506.3 Calcd 506.15; $^1$HNMR δ 7.75–7.48 (m, 5H), 6.92 (d, 1H), 6.59 (dd, 1H), 6.28 (d, 1H), 3.62 (app t, 2H), 3.41 (app t, 2H), 3.21 (app t, 2H), 3.12 (app t, 2H), 2.23 (s, 3H), 2.13 (s, 3H), 2.09–2.01 (m, 2H).

Example 65

N-{4-(1,4-diazepan-1-yl)-2-[(phenylsulfonyl)amino]phenyl}-5-fluoro-2-methylbenzenesulfonamide hydrochloride (Scheme 3)

The compound was synthesized from of N-{2-amino-5-(4-t-butyloxycarbonyl-1,4-diazepan-1-yl)-phenyl}benzenesulfonamide and 5-fluoro-2-methylbenzenesulfonylchloride (56 mg, 0.269 mmole) to give 7 mg as purple solid. M+1 519.3 Calcd 519.15; $^1$HNMR δ 7.78–7.18 (m, 8H), 6.72 (d, 1H), 6.45 (dd, 1H), 6.34 (d, 1H), 3.59 (app t, 2H), 3.38 (app t, 2H), 3.21 (app t, 2H), 3.13 (app t, 2H), 2.57 (s, 3H), 2.06–1.98 (m, 2H).

Example 66

N-{4-(1,4-diazepan-1-yl)-2-[(phenylsulfonyl)amino]phenyl}-4-(methylsulfonyl)benzenesulfonamide hydrochloride (Scheme 3)

The compound was synthesized from of N-{2-amino-5-(4-t-butyloxycarbonyl-1,4-diazepan-1-yl)-phenyl}benzenesulfonamide and 4-methylsulfonylbenzenesulfonylchloride (69 mg, 0.269 mmole) to give 38 mg as purple solid. M+1 565.3 Calcd 565.12; $^1$HNMR δ 8.08–7.48 (m, 9H), 6.76 (d, 1H), 6.48 (dd, 1H), 6.32 (d, 1H), 3.61 (app t, 2H), 3.21 (app t, 2H), 3.17 (app t, 2H), 3.14 (app t, 2H), 2.08–2.00 (m, 2H).

Example 67

N-{4-(1,4-diazepan-1-yl)-2-[(methylsulfonyl)amino]phenyl}-N-methylbenzenesulfonamide (Scheme 3)

N-methyl-{2-amino-5-(4-t-butyloxycarbonyl-1,4-diazepan-1-yl)-phenyl}-benzenesulfonamide (0.196 g, 0.426 mmol) was dissolved in pyridine (1.67 ml) followed by the addition of methyl sulphonylchloride (57 mg, 0.50 mmol) The ractiom was stirred at rt for 3 h. The mixture was concentrated and treated with trifluoroacetic acid (50%) in DCM for 30 min then concentrated and left for our HPLC Separation specialists. Further purification by column cheomatography DCM/MeOH (9:1) afforded 32 mg, 0.058 mmol in 13% yield of the title compound. $^1$H NMR (CD$_3$OD) δ 2.17 (m, 2H), 3.05 (s, 3H), 3.14 (s, 3H), 3.27 (m, 2H), 3.38 (m, 2H), 3.57 (m, 2H), 3.77 (m, 2H), 6.28 (d, 1H), 6.41 (dd, 1H), 7.06 (d, 1H), 7.65 (m, 5H); $^{13}$C NMR (CD$_3$OD) δ 25.0, 38.7, 39.0, 45.1, 45.5, 45.8, 47.0, 100, 103.9, 108.1, 121.4, 125, 126, 128, 133.4, 136, 137.5, 148.5; M/Z Calc for (C$_{19}$H$_{26}$N$_4$O$_4$S$_2$) 438.14 Found M$^+$+1=439.2.

Example 68

N-{5-(1,4-diazepan-1-yl)-2-[methyl(phenylsulfonyl)amino]phenyl}-4-methylbenzenesulfonamide (Scheme 3)

N-methyl-{2-amino-5-(4-t-butyloxycarbonyl-1,4-diazepan-1-yl)-phenyl}-benzenesulfonamide (0.196 g, 0.426 mmol) was dissolved in pyridine (1.67 ml) followed by the addition of p-methylphenyl-sulphonylchlride (88 mg, 0.50 mmol) the reaction was stirred at rt for 3 h. The mixture was concentrated and treated with trifluoroacetic acid (50%) in DCM for 30 min then concentrated and left for our HPLC Separation specialists. Further purificaction by flash column chromatography DCM/MeOH (9:1) afforded 0.110 g, 0.175 mmol in 40% yield of title compound. $^1$H NMR (CD$_3$OD) δ 2.17 (m, 2H), 2.52, (s, 3H), 3.0–3.4 (m, 7H), 3.52 (m, 2H), 3.74 (m, 2H), 6.15 (d, 1H), 6.41 (d, 1H), 6.92 (s, 1H), 7.5–7.80 (m, 6H); M/Z Calc for (C$_{25}$H$_{30}$N$_4$O$_4$S$_2$) 514.1708. Found M$^+$ 514.1708.

General Method for the Preparation of Monosulfonamides

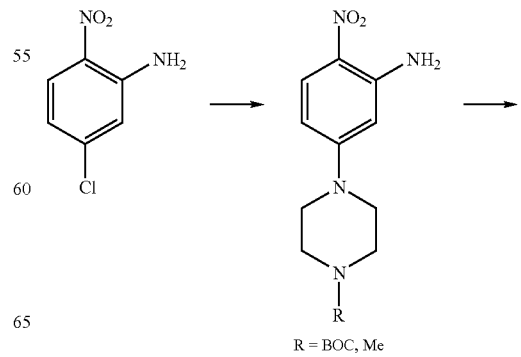

Scheme 4

R = BOC, Me

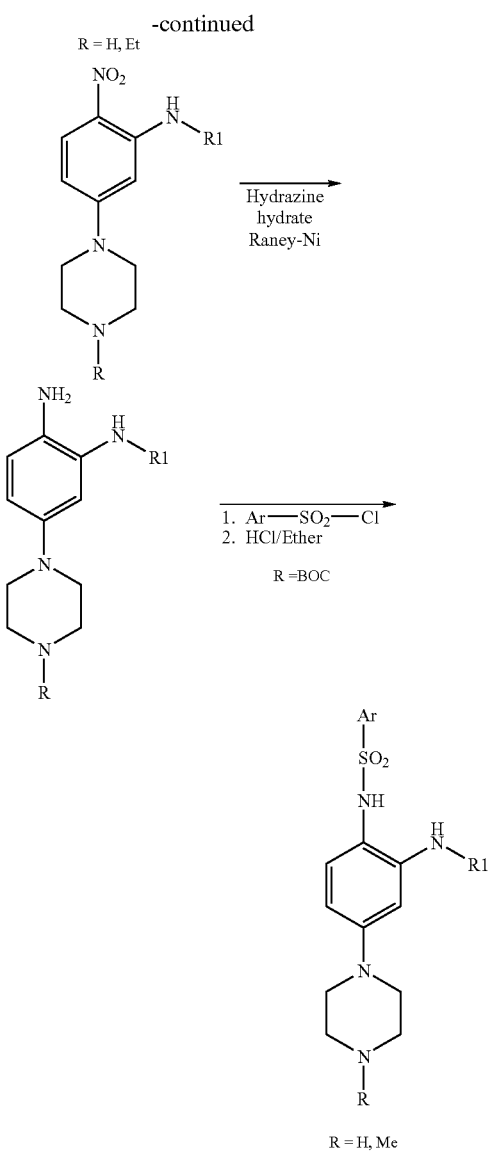

Example 69

N-[2-Amino-4-(1-piperazinyl)phenyl]-3-fluorobenzenesulfonamide (Scheme 4)

tert-Butyl 4-(3-amino-4-nitrophenyl)-1-piperazinecarboxylate (1.5 g, 3.5 mmol) was dissolved in methanol:THF (4:1). Raney-Ni (900 mg) was added followed by addition of hydrazine monohydrate (900 mg). The reaction was stirred at r. t. under $N_2$ atmosphere overnight. Starting material was present. Raney-Ni (400 mg) was added and the reaction was stirred overnight. The reaction was filtered through celite pad followed by washings with ethanol. The volatiles were evaporated to afford 93% of 2-amino-5-(4-t-buthylcaboxyl-1-piperazinyl) aniline.

2-amino-5-(4-t-buthylcaboxyl-1-piperazinyl) aniline (150 mg, 0.382 mmol) was dissolved in $CH_2Cl_2$ (2 mL). 3-fluorophenylsulfonylchloride (74 mg, 0.382 mmol), pyridine (215 µL, 2.67 mmol) were added and the reaction was stirred at room temperature for 2 hr. The reaction was quenched with $NaHCO_3$ (saturated aqueous solution), extracted with $CH_2Cl_2$. The organic phase was dried ($MgSO_4$), filtered and concentrated to give an oil residue that was purified by flash colunm chromatography ($SiO_2$, $CH_3Cl$:MeOH:$NH_3$ 9:1:0.4%) to afford of N-[2-amino-4-(4-tert-butylcarboxyl-1-piperazinyl)-3 fluorobenzenesulfonamide (80%).

N-[2-amino-4-(4-tert-butylcarboxyl-1-piperazinyl)-3-fluorobenzenesulfonamide (110 mg) were dissolved in methanol (0.5 mL) followed by the addition of diethylether (2 mL). Ether/HCl gas was added till pH=1. The reaction was stirred at room temperature for 5 h to afford the title product as a white solid $^1$H NMR (methanol-d3) δ 3.25–3.50 (m, 8H); 6.5 (d, 1H); 6.75 (dd, 1H); 7.0 (bs, 1H); 7.3–7.6 (m, 4H); MS (posEI-DIP) m/z=351.2 (M+H).

Example 70

N-[2-(ethylamino)-4-(4-methyl-1-piperazinyl)phenyl]-3-fluorobenzenesulfonamide hydrochloride (Scheme 4)

To a solution of N-2-ethyl-4-(4-methyl-1-piperazinyl)-1,2-benzenediamine (0.200 g, 0.853 mmol) and pyridine (0.48 mL, 5.97 mmol) in DCM (8 mL) was added a solution of 3-fluorobenzenesulfonyl chloride (249 mg, 1.28 mmol) in DCM (2 mL). The mixture was stirred at room temperature for 16 hours. DCM (10 mL) was added and the mixture was washed with saturated aqueous $NaHCO_3$. The organic layer was dried over $Na_2SO_4$, filtered and concentrated. Column chromatography on $Al_2O_3$ using EtOAc/5% MeOH as eluent gave two products. First fraction contains 110 mg of N-[2-{ethyl[(3-fluorophenyl)sulfonyl]amino}-4-(4-methyl-1-piperazinyl)phenyl]-3-fluorobenzenesulfonamide hydrochloride. Second fraction contains 100 mg of N-[2-(ethylamino)-4-(4-methyl-1-piperazinyl)phenyl]-3fluorobenzenesulfonamide hydrochloride. Both products were converted to the HCl-salts. N-[2-(ethylamino)-4-(4-methyl-1-piperazinyl)phenyl]-3-fluorobenzenesulfonamide hydrochloride: $^1$H NMR (DMSO-d6) δ 11.24 (br s, 1H), 9.76 (br s, 1H), 7.66–7.59 (m, 1H), 7.56–7.50 (m, 3H), 6.62 (app d, J=8.8 Hz, 1H), 6.55–6.35 (m, 2H), 3.80–3.70 (m, 2H), 3.46–3.40 (m, 2H), 3.15≧2.96 (m, 6H), 2.76 (app d, J=4.4 Hz, 3H), 1.08 (tr, J=7.2 Hz, 3H); 13C NMR (CD$_3$OD) δ 161.03 (d, $J_{CF}$=248 Hz), 149.32, 142.13 (d, $J_{CF}$=6.4 Hz), 140.72, 131.43 (d, $J_{CF}$=7.4 Hz), 128.56, 123.22, 119.93 (d, $J_{CF}$=20 Hz), 115.91, 113.86 (d, $J_{CF}$=24 Hz), 107.78, 103.12, 51.83, 45.04, 41.80, 40.62, 12.88; AccMs (posES-FIA) found: 392.1672, calc: 392.1782; Ms (posES-FIA) m/z 393 (M+H).

Example 71

4-Chloro-N-[5-(4-methyl-1,4-diazepan-1-yl)-2-nitrophenyl]benzenesulfonamide (Scheme 4)

4-chlorobenzene sulfonamide (3.5 g, 18.3 mmol) was added slowly to a suspension of sodium hydride (1.6 g, 55% suspension in mineral oil, 36.6 mmol) in anhydrous DMF (50 mL) under an atmosphere of nitrogen. The mixture was warmed to 40° C. for 1 hour and 2,4-difluoronitrobenzene (2 mL) was added dropwise. This mixture was stirred at 60° C.

overnight. The cooled reaction mixture was poured into hydrochloric acid (1 N, 250 mL) and extracted with ethyl acetate (2×50 mL). The organic extracts were washed with water, dried over MgSO$_4$ and evaporated to give a yellow solid. The product was re-crystallized from ethanol. Yield 2.4 g (40%). $^1$H NMR (400 MHz, CDCl$_3$) δ 6.85 (m, 1H), 7.48 (AB, J=8.3 Hz, 2H), 7.56 (dd, J=10.01, 2.68 Hz, 1H), 7.84 (AB, J=8.3 Hz, 2H), 8.21 (dd, J=9.28, 5.61 Hz, 1H), 10 (bs, 1H). Calculated N, 8.47%; C, 43.58%; S 9.70%; H 2.44%. Found N, 8.54%; C43.89%; S10.10%; H 2.76%. 4-Chloro-N-[5-fluoro-2-nitrophenyl]benzenesulfonamide (1 g, 3 mmol) and N-methylhomopiperazine (0.4 mL) were heated together at 130° C. for 3 hours. The product was allowed to cool, dissolved in CH$_2$Cl$_2$ (50 mL) and washed with aqueous sodium bicarbonate. The organic phase was dried over MgSO$_4$ and evaporated to give 1.05 g of a yellow solid which was re-crystallized from toluene. Yield 0.65 g (51%). $^1$H NMR (400 MHz, CDCl$_3$) δ 1.98 (q, J=5.62 Hz, 1H), 2.37 (s, 3H), 2.52 (t, J=5.62 Hz, 2H), 2.67 (t, J=5.12 Hz, 2H), 3.55 (t, J=6.35 Hz, 2H), 3.60 (t, J=5.12 Hz, 2H), 6.34 (dd, J=9.77, 2.68 Hz, 1H), 6.86 (d, J=2.68 Hz, 1H), 7.43 (ab, J=8.79 Hz, 2H), 7.79 (ab, J=8.79 Hz, 2H), 8.01 (d, J=9.77 Hz, 1H), 11.6 (br s, 1H). Calculated N, 13.19%; C, 50.88%; H, 4.98%. Found N, 13.27%, C, 50.99%, H, 4.83%.

Example 72

N-[2-amino-5-(1,4-diazepan-1-yl)phenyl]benzene-sulfonamide (Scheme 4)

N-{5-(4-t-butyloxycarbonyl-1,4-diazepan-1-yl)-2-nitro-phenyl}benzenesulfonamide (1.85 g, 3.88 mmol) was dissolved in EtOH/THF (1:4). Hydrazine (0.970 mL, 19.4 mmol) and Raney-Ni (0.180 g) was added. After 1 h at room temperature, the reaction was filtered through wet celite and the solvent was removed to afford 1.71 g of colorless oil. Boc-deprotection was achieved by dissolving N-{5-(4-t-butyloxycarbonyl-1,4-diazepan-1-yl)-2-amino-phenyl}benzenesulfonamide (0.039 g) in small amount of MeOH and adding HCl/ether. The mixture was left at room temperature for 0.5 h after which the solvent was removed. Re-crystallization from MeOH/ether gave PHA-509592A (23 mg) as a white solid. M+1 347.4 Calcd 347.15; $^1$H-NMR δ 7.73–7.54 (m, 5H), 7.30 (d, 1H), 6.84 (dd, 1H), 5.78 (d, 1H), 3.55 (app t, 2H), 3.32–3.26 (m, 2H), 3.13–3.08 (m, 4H), 2.03–1.92 (m, 2H).

Example 73

N-[2-amino-5-(4-methyl-1,4-diazepan-1-yl)phenyl]benzenesulfonamide hydrochloride (Scheme 4)

The above sulfonamide (0.6 g, 1.8 mmol) in methanol (50 mL) with Palladium (10% on C, 0.3 g) was hydrogenated at atmospheric pressure for one hour during which time 140 mL of hydrogen was consumed. The solution was filtered and evaporated to give colorless oil. The oil was dissolved in toluene (20 mL) and treated with a solution of hydrogen chloride in ethyl acetate. The product was triturated with cyclohexane, collected by filtration and dried. Yield 0.44 g (73%). A portion was recrystallized from toluene:ethanol 1:1. $^1$H NMR (400 MHz, CDCl$_3$) δ 1.95 (br, 1H), 2.17 (br, 1H), 2.72 (s, 3H), 2.80–3.65 (br m, 8H), 5.92 (br, 1H), 6.66 (dd, J=2.69, 9.03 Hz, 1H), 7.20 (d, J=9.03 Hz, 1H), 7.63 (t, J=7.81 Hz, 2H), 7.71 (t, J=7.32 Hz, 1H), 7.81 (d, J=7.32 Hz, 2H), 9.8 (br, 3H), 11 (br s, 1H). MS (ESI+) for C$_{18}$H$_{24}$N$_4$O$_2$S m/z 360.1634 (M+)$^+$ (Calculated 360.1620)

Example 74

N-[4-Nitro-3-(1-piperazinyl)phenyl]benzenesulfonamide hydrochloride (Scheme 4)

A mixture of difluoronitrobenzene (1.31 g, 8.21 mmol), Boc-piperazine (1.84 g, 9.8 mmol) and K$_2$CO$_3$ in DMF was stirred at room temperature overnight. The mixture was filtered and the DMF was removed. The residue was dissolved in CH$_2$Cl$_2$ and extracted with HCl (1M) three times. The organic layers were dried (MgSO$_4$), filtered and the solvent was removed. Purification by column chromatography (SiO$_2$, CH$_2$Cl$_2$/heptane, 1:4) gave 1.14 g of yellow solid. $^1$H-NMR δ 7.90 (dd, 1H), 6.77–6.69 (m, 2H), 3.60–3.57 (m, 4H), 3.03–3.00 (m, 4H), 1.46 (s, 9H); MS (posEI-DIP) m/z=Found: 348.2 (M$^+$+Na$^+$). NaH (17.2 mg, 0.43 mmol) was added to a solution of 4-(2-nitro-5-fluorophenyl)-1-(t-butyloxycarbonyl)piperazine (0.079 g, 0.215 mmol) and benzensulfonamide (0.044 g, 0.280 mmol) in DMF. The mixture was heated at 80° C. over night and filtered. Purification by column chromatography (SiO$_2$, CH$_2$Cl$_2$/heptane, 1:4) gave 0.075 g of N-[2-nitro-4-(t-butyloxycarbonylpiperazinyl)]phenyl]benzenesulfonamide of which 0.025 mg was Boc-deprotected by dissolving the compound in MeOH and adding HCl/ether. The mixture was stirred for 0.5 h after which the solvent was removed. Re-crystallization MeOH/ether gave 24.6 mg of a yellow solid. $^1$H-NMR δ 7.88 (app d, 3H), 7.63–7.52 (m, 3H), 7.07 (d, 1H), 6.89 (dd, 1H), 3.38–3.34 (m, 4H), 3.25–3.21 (m, 4H); MS (posEI-DIP) m/z=Found: 363.3 (M$^+$+H$^+$).

Example 75

N-[4-amino-3-(1-piperazinyl)phenyl]benzenesulfonamide hydrochloride (Scheme 4)

To a solution of N-[2-nitro-4-(t-butyloxycarbonylpiperazinyl)]phenyl] benzensulfonamide (50 mg, 0.108 mmol) in THF/EtOH 4:1 was added Raney-Ni (5 mg) and hydrazine hydrate (27 μL, 0.54 mmol). The mixture was stirred at room temperature for 6 h followed by filtration of the reaction mixture through wet Celite. Removal of the solvent and purification by column chromatography (SiO$_2$, CH$_2$Cl$_2$/heptane/MeOH, 4:5:1) gave N-[2-amino-4-(t-butyloxycarbonyl-piperazinyl)]phenyl]-benzenesulfonamide. Boc-deprotection was achieved by dissolving the compound in MeOH and adding HCl/ether. The mixture was stirred for 0.5 h after which the solvent was removed. Re-crystallization (MeOH/ether) gave a white solid that had to be purified by preparative HPLC to obtain 10 mg of the final product. $^1$H-NMR δ 7.66–7.45 (m, 5H), 6.78 (d, 1H), 6.62 (d, 1H), 6.50 (dd, 1H), 3.39–3.35 (m, 4H), 3.02–2.99 (m, 4H); MS (posEI-DIP) m/z=Found: 333.0 (M$^+$+H$^+$).

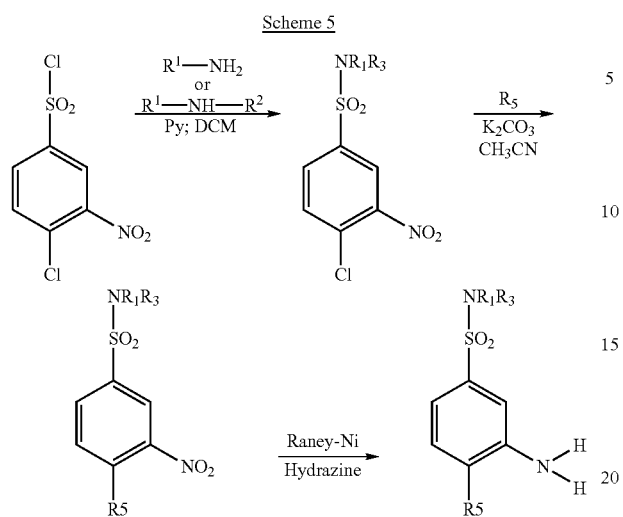

Scheme 5

Method 5

4-Chloro-3-nitrobenzenesulfonyl chloride, taken from a prepared stock solution, (1.78 mmol, 1.0 eq) in $CH_2Cl_2$ (2 mL) was added to a solution of the appropriate R''—substituted anilines ($R^1$—$NH_2$ or $R^1$—NH—$R^3$) (1.62 mmol, 1.0 equiv.) in the presence of pyridine (11.34 mmol, 7.0 equiv.).

The reactions were stirred overnight at room temperature. Each mixture was washed with 1N HCl followed by $NaHCO_3$ (sat. aqueous). Each organic phase was separated, dried ($Na_2SO_4$), and filtered. $CH_2Cl_2$ (2 mL) were added to each reaction mixture followed by the addition of $K_2CO_3$ (3.24 mmol, 2.0 equiv.) and homopiperazine or other amines of choice (i.e. $R^5$) (2.11 mmol, 1.3 equiv.). Each reaction mixture was stirred at room temperature for 2 days. The volatiles were eliminated using a speed vac. Each reaction mixture was dissolved in a 4:1 EtOH:THF (25 mL) followed by addition of Raney-Ni (0.5 mL suspension in EtOH) and hydrazine monohydrate (8.10 mmol, 5.0 equiv.). Each mixture was stirred at room temperature for 2 days and then filtered (Celite pad pretreated with water). The filtrates were concentrated to give the crude products (LC-MS). An aliquot of each reaction mixture was purified by reversed phase preparative HPLC to give analytical samples which were converted to their HCl-salts and sent for pharmacological testing.

Example 76

3-Amino-4-(1,4-diazepan-1-yl)-N-(4-methoxyphenyl)benzenesulfonamide hydrochloride (Scheme 5, Method 5)

The compound was prepared from p-anisidine; (crude yield 0.238 g, yield analytical pure sample 0.137 g); $^1$H NMR ($CDCl_3$) δ 7.43–7.39 (m, 2H), 7.37–7.33 (m, 1H), 7.00–6.96 (m, 2H), 6.78–6.74 (m, 2H), 3.71 (s, 3H), 3.47–3.38 (m, 6H), 3.17–3.13 (m, 2H), 2.19–2.12 (m, 2H); MS (posESI) m/z=377 (M+H$^+$).

Example 77

3-Amino-4-(1,4-diazepan-1-yl)-N-(3-methoxyphenyl)benzenesulfonamide hydrochloride (Scheme 5, Method 5)

The compound was prepared from m-anisidine; (crude yield 0.546 g, yield analytical pure sample 0.020 g); $^1$H NMR ($CDCl_3$) δ 7.71–7.67 (m, 2H), 7.51–7.47 (m, 1H), 7.12–7.07 (m, 1H), 6.72–6.69 (m, 1H), 6.68–6.65 (m, 1H), 6.63–6.59 (m, 1H), 3.71 (s, 3H), 3.48–3.40 (m, 6H), 3.18–3.14 (m, 2H), 2.21–2.15 (m, 2H); MS (posES-FIA) m/z=377 (M+H$^+$).

Example 78

3-Amino-4-(1,4-diazepan-1-yl)-N-(2-methoxyphenyl)benzenesulfonamide hydrochloride (Scheme 5, Method 5)

The compound was prepared from o-anisidine; (crude yield 0.469 g, yield analytical pure sample 0.010 g); $^1$H NMR ($CDCl_3$) δ 7.51–7.47 (m, 2H), 7.42–7.35 (m, 2H), 7.11–7.06 (m, 1H), 6.89–6.82 (m, 2H), 3.57 (s, 3H), 3.47–3.38 (m, 6H), 3.17–3.12 (m, 2H), 2.20.2.13 (m, 2H); MS (posES-FIA) m/z=377 (M+H$^+$).

Example 79

3-Amino-4-(1,4-diazepan-1-yl)-N-(3-fluorophenyl)benzenesulfonamide hydrochloride (Scheme 5, Method 5)

The compound was prepared from 3-fluoroaniline; (crude yield 0.580 g, yield analytical pure sample 0.043 g); $^1$H NMR ($CD_3OD$) δ 7.58–7.49 (m, 2H), 7.41–7.35 (m, 1H), 7.23–7.17 (m, 1H), 6.93–6.87 (m, 2H), 6.79–6.73 (m, 1H), 3.46–3.37 (m, 6H), 3.17–3.13 (m, 2H), 2.20–2.12 (m, 2H); MS (posES-FIA) m/z=365 (M+H$^+$).

Example 80

3-Amino-4-(1,4-diazepan-1-yl)-N-methyl-N-phenylbenzenesulfonamide hydrochloride (Scheme 5, Method 5)

The compound was prepared from N-methylaniline; (crude yield 0.590 g, yield analytical pure sample 0.010 g); $^1$H NMR ($CD_3OD$) δ 7.41–7.36 (m, 1H), 7.35–7.22 (m, 5H), 7.15–7.11 (m, 2H), 3.50–3.44 (m, 6H), 3.23–3.17 (m, 5H), 2.33–2.16 (m, 2H), MS (posEI) m/z=360 (M+H$^+$).

Example 81

3-Amino-4-(1,4-diazepan-1-yl)-N-(4-isopropylphenyl)benzenesulfonamide hydrochloride (Scheme 5, Method 5)

The compound was prepared from 4-isopropylaniline; (crude yield 0.600 g, yield analytical pure sample 0.015 g); $^1$H NMR ($CD_3OD$) δ 7.48–7.41 (m, 2H), 7.35–7.31 (m, 1H), 7.10–7.05 (m, 2H), 7.03–6.98 (m, 2H), 3.47–3.35 (m, 6H), 3.17–3.12 (m, 2H), 2.80 (sept, J=6.8 Hz, 1H), 2.20–2.10 (m, 2H), 1.17 (d, J=6.8 Hz, 6H); MS (posEI) m/z=388 (M+H$^+$).

Example 82

3-Amino-4-(1,4-diazepan-1-yl)-N-(4-methylphenyl)benzenesulfonamide hydrochloride (Scheme 5, Method 5)

The compound was prepared from p-toluidine; (crude yield 0.590 g, yield analytical pure sample 0.020 g); $^1$H NMR ($CD_3OD$) δ 7.35–7.33 (m, 1H), 7.31–7.27 (m, 1H), 7.25–7.22 (m, 1H), 7.03–6.94 (m, 4H), 3.47–3.30 (m, partly obscured by solvent signal, 6H), 3.16–3.11 (m, 2H), 2.23 (s, 3H), 2.17–2.10 (m, 2H) ; MS (posESI) m/z=360 (M+H⁺).

Example 83

3-Amino-4-(1,4-diazepan-1-yl)-N-(2,5-dimethylphenyl)benzenesulfonamide hydrochloride (Scheme 5, Method 5)

The compound was prepared from 2,4-dimethylaniline; (crude yield 0.306 g, yield analytical pure sample 0.015 g); $^1$H NMR (CD$_3$OD) δ 7.33–7.28 (m, 3H), 6.99–6.95 (m, 1H), 6.93–6.88 (m, 2H), 3.50–3.37 (m, 6H), 3.19–3.14 (m, 2H), 2.22–2.13 (m, 5H), 1.96 (s, 3H); MS (posES-FIA) m/z=375 (M+H⁺).

Example 84

3-Amino-N-(3-chlorophenyl)-4-(1,4-diazepan-1-yl) benzenesulfonamide hydrochloride (Scheme 5, Method 5)

The compound was prepared from 3-chloroaniline; (crude yield 0.610 g, yield analytical pure sample 0.015 g); $^1$H NMR (CD$_3$OD) δ 7.25–7.24 (m, 1H), 7.19–7.14 (m, 3H), 7.12–7.10 (m, 1H), 7.04–6.99 (m, 2H), 3.45–3.30 (m, partly obscured by solvent signal, 6H), 3.15–3.11 (m, 2H), 2.14–2.08 (m, 2H); MS (posES-FIA) m/z=381 (M+H⁺).

Example 85

3-Amino-4-(1,4-diazepan-1-yl)-N-(2-chlorophenyl) benzenesulfonamide hydrochloride (Scheme 5, Method 5)

The compound was prepared from 2-chloroaniline; (crude yield 0.506 g, yield analytical pure sample 0.020 g); $^1$H NMR (CD$_3$OD) δ 7.55–7.50 (m, 1H), 7.40–7.20 (m, 5H), 7.15–7.10 (m, 1H), 3.48–3.34 (m, 6H), 3.18–3.12 (m, 2H), 2.20–2.10 (m, 2H); MS (posEI) m/z=381 (M+H⁺).

Example 86

3-Amino-N-(2,4-dichlorophenyl)-4-(1,4-diazepan-1-yl)benzenesulfonamide hydrochloride (Scheme 5, Method 5)

The compound was prepared from 2,4-dichloroaniline; (crude yield 0.446 g, yield analytical pure sample 0.080 g); $^1$H NMR (CD$_3$OD) δ 7.53–7.50 (m, 1H), 7.37–7.35 (m, 1H), 7.32–7.27 (m, 2H), 7.25–7.23 (m, 2H), 3.48–3.37 (m, 6H), 3.18–3.12 (m, 2H), 2.20–2.10 (m, 2H); MS (posEI) m/z=415 (M+H⁺).

Example 87

3-Amino-N-(2-methyl-5-chloro-phenyl)-4-(1,4diazepan-1-yl)benzenesulfonamide hydrochloride (Scheme 5, Method 5)

The compound was prepared from 2-methyl-5-chloroaniline; (crude yield 0.516 g, yield analytical pure sample 0.015 g); $^1$H NMR (CD$_3$OD) δ 7.47–7.34 (m, 3H), 7.16–7.13 (m, 1H), 7.10 (–7.04 (m, 2H), 3.48–3.39 (m, 6H), 3.20–3.15 (m, 2H), 2.21–2.14 (m, 2H); MS (posESI) m/z=395 (M+H⁺).

Example 88

3-Amino-N-(2-methyl-3-chloro-phenyl)-4-(1,4-diazepan-1-yl)benzenesulfonamide hydrochloride (Scheme 5, Method 5)

The compound was prepared from 2-methyl-3-chloroaniline; (crude yield 0.537 g, yield analytical pure sample 0.22 g); $^1$H NMR (CD$_3$OD) δ 7.40–7.34 (m, 3H), 7.26–7.23 (m, 1H), 7.08–6.99 (m, 2H), 3.50–3.38 (m, 6H), 3.20–3.16 (m, 2H), 2.21–2.14 (m, 2H) 2.11 (s, 3H); MS (posESI) m/z=395 (M+H⁺).

Example 89

3-Amino-N-(4-trifluoro-phenyl)-4-(1,4-diazepan-1-yl)benzenesulfonamide hydrochloride (Scheme 5, Method 5)

The compound was prepared from 4-trifluoroaniline; (crude yield 0.319 g, yield analytical pure sample 0.013 g); $^1$H NMR (CD$_3$OD) δ 7.53–7.45 (m, 2H), 7.27–7.22 (m, 3H), 7.13–7.08 (m, 2H), 3.43–3.30 (m, partly obscured by solvent signal, 6H), 3.14–3.09 (m, 2H), 2.12–2.06 (m, 2H); MS (posESI) m/z=415 (M+H⁺).

Example 90

3-Amino-N-(4-fluorophenyl)-4-(1,4diazepan-1-yl) benzenesulfonamide hydrochloride (Scheme 5, Method 5)

The compound was prepared from 4-fluoroaniline; (crude yield 0.700 g, yield analytical pure sample 0.021 g); $^1$H NMR (CD$_3$OD) δ 7.13–7.04 (m, 4H), 7.03–6.98 (m, 1H), 6.97–6.91 (m, 2H), 3.45–3.30 (m, partly obscured by solvent signal, 6H), 3.15–3.09 (m, 2H); MS (posEI) m/z=365 (M+H⁺).

Example 91

3-Amino-N-(2-fluorophenyl)-4-(1,4diazepan-1-yl) benzenesulfonamide hydrochloride (Scheme 5, Method 5)

The compound was prepared from 2-fluoroaniline; (crude yield 0.646 g, yield analytical pure sample 0.080 g); $^1$H NMR (CD$_3$OD) δ 7.48–7.43 (m, 1H), 7.36–7.34 (m, 1H), 7.36–7.27 (m, 1H), 7.25–7.21 (m, 1H), 7.15–7.05 (m, 2H), 7.02–6.95 (m, 1H), 3.46–3.34 (m, 6H), 3.17–3.12 (m, 2H), 2.16–2.10 (m, 2H); MS (posESI) m/z=365 (M+H⁺).

Example 93

4-(1,4-Diazepan-1-yl)-3-nitro-N-benzenesulfonamide hydrochloride (Scheme 5, Method 5)

4-Chloro-3-nitro-N-benzenesulfonamide (1.52 g, 4.87 mmol), K$_2$CO$_3$ (1.01 g, 7.3 mmol) and homopiperazine (0.585 g, 5.8 mmol) in CH$_3$CN (100 mL) was heated to 70° C. for 2 h. The mixture was filtered and the solvent was removed. Column chromatography (CH$_2$CL$_2$/MeOH/heptane 4:1:5×0.2% NH$_3$) gave 1.34 g of 4-(1,4-diazepan-1- yl)-3-nitro-N-benzenesulfonamide together with 0.152 g of the dialkylated product. The product (0.040 g) was transferred to its HCl-salt to give 0.038 g of the final product. Anal. ($C_{17}H_{21}ClN_4O_4S \times 0.5H_2O$) C, H, N.; MS (posESI) m/z=377.4 (M+H$^+$).

Example 94

3-Amino-4-(1,4-diazepan-1-yl)-N-phenylbenzenesulfonamide hydrochloride (Scheme 5, Method 5)

4-(1,4-Diazepan-1-yl)-3-nitro-N-phenylbenzenesulfonamide (0.599 g, 1.6 mmol) was dissolved in EtOH/THF (1:4). Hydrazine (0.398 mL, 8.0 mmol) and Raney-Ni (0.060 g) were added. After 1 h at room temperature the reaction was filtered through wet celite and the solvent was removed. The product was transferred to its HCl-salt by dissolving it in MeOH and adding HCl/ether. The solvent was removed and re-crystallized from (MeOH/ether) to give 0.537 g of a white solid. Anal. ($C_{17}H_{21}ClN_4O_4S \times 1.5H2O$) C, H, N.; MS (posESI) m/z=347.4 (M+H$^+$).

Example 92

3-Amino-4-(4-methyl-1,4-diazepan-1-yl)-N-phenylbenzenesulfonamide (Scheme 5, Method 5)

4-Chloro-3-nitrobenzenesulfonyl chloride (460 mg, 1.8 mmol) was added to a colorless solution of aniline (250 mg, 2.7 mmol) in $CH_2Cl_2$ (10 mL) followed by pyridine (0.80 mL, 10.0 mmol). The resulting orange solution was stirred at room temperature for 30 minutes, after which time the mixture was concentrated under vacuum. Acidification with 2M aq. HCl followed by extraction using EtOAc and drying with $Na_2SO_4$ followed by filtration through a plug of silica, gave 500 mg (62%) of 4-chloro-3-nitro-N-phenylbenzenesulfonamide. $^1$H NMR (CDCl$_3$) δ 8.30 (d, 1H), 7.80 (dd, 2H), 7.55 (d, 1H), 7.20 (m, 5H). MS(negESI) m/z=311(M−H$^+$). 1-Methylhomopiperazine (258 mg, 2.3 mmol) was added to a solution of 4-chloro-3-nitro-N-phenylbenzenesulfonamide obtained as above (500 mg, 1.6 mmol) in $CH_2Cl_2$ (20 mL) followed by addition of $K_2CO_3$ (310 mg, 2.3 mmol). The reaction mixture was heated to reflux. After 2.5 h, the solution was concentrated under vacuum. After adjusting to pH=6, the product was extracted using EtOAc to give, after drying with $Na_2SO_4$ and concentration, 450 mg (72%) of 4-(4-methyl-1,4-diazepan-1-yl)-3-nitro-N-phenylbenzenesulfonamide as an orange oil. $^1$H NMR (CDCl$_3$) δ 8.15 (d, 1H), 7.60 (dd, 1H), 7.15 (m), 6.95 (d, 1H), 3.45 (m, 2H), 3.30 (m, 2H), 2.75 (m, 2H), 2.60 (m, 2H), 2.35 (s, 3H), 1.95 (m, 2H). MS (posESI) m/z=391(M+H$^+$). To a solution of 4-(4-methyl-1,4-diazepan-1-yl)-3-nitro-N-phenylbenzenesulfonamide (225 mg, 0.58 mmol) in EtOH/THF (4/1, 25 mL) activated Raney-Ni (slurry in EtOH) and hydrazine monohydrate (142 μL, 2.9 mmol) were added. After stirring for 30 minutes at room temperature, the mixture was filtered and the yellow solution concentrated to give yellow oil. The oil was dissolved in a mixture diethyl ether/EtOAc followed by addition of excess of HCl/ether. The resulting precipitate was filtered and washed with ether to give, after drying under vacuum at 40° C., 88 mg (38%) of 3-amino-4-(4-methyl-1,4-diazepan-1-yl)-N-phenylbenzenesulfonamide as a beige solid. Mp 84–85° C. MS (posESI) m/z=361 (M+H$^+$). $^1$H NMR (MeOH-d3) δ 7.85 (d, 2H), 7.60 (d, 1H), 7.15 (m, 5H), 3.50 (m, 7H), 3.15 (m, 2H), 3.00 (s, 3H), 2.30 (m, 1H), 2.20 (m, 1H). Anal. ($C_{18}H_{24}N_4SO_2 \cdot 2HCl$) C, H, N, S.

Example 98

3-Amino-N-(3-chlorophenyl)-4-(4-methyl-1-1-piperazinyl)benzenesulfonamide hydrochloride (Scheme 5, Method 5)

A mixture of 4-chloro-3-nitrobenzenesulfonylchloride (1 g, 3.9 mmol), 3-chloroaniline (0.5 mL, 4.7 mmol) and pyridine (1.6 mL) in $CH_2Cl_2$ (2 mL) was stirred at room temperature. The reaction was quenched with NaHCO$_3$ (sat aq solution, 30 mL×3). The organic phase was separated, dried (MgSO$_4$), and filtered. The volatiles were evaporated and the residue was purified by column chromatography (SiO$_2$, pentane:EtOAc, 4:1) to give 4-chloro-N-(3-chlorophenyl)-3-nitrobenzenesulfonamide; MS (posESI) m/z=349.2 (M+H$^+$). $^1$H NMR (CDCl$_3$) δ 7.00–7.40 (m, 3H), 7.60–7.90 (m, 3H), 8.70 (bs, 1H). 4-Chloro-N-(3-chlorophenyl)-3-nitrobenzenesulfonamide (0.45 g, 1.3 mmol), N-methylpiperazine (0.191 mL, 1.73 mmol) and K$_2$CO$_3$ (359 mg, 2.6 mmol) in CH$_3$CN (2.5 mL) as the filtrated was concentrated to give a residue which was purified by column (SiO$_2$, CHCl$_3$:MeOH:NH$_3$ 9:1:0.4%) to give 420 mg of N-(3-chlorophenyl)-4-(4-methyl-1-piperazinyl)-3-nitrobenzenesulfonamide (85%). Purity>95% according to HPLC analysis. The compound was dissolved in THF (1 mL) and ethanol (5 mL) was added. The solution was treated with Raney-Ni (50 mg) and hydrazine monohydrate (0.05 mL) overnight. The Raney-Ni was filtered (celite pad), the volatiles were evaporated and the residue was purified by column chromatography (SiO$_2$, CHCl$_3$:MeOH:NH$_3$ 9:1:0.4%). The product was isolated as hydrochloride salt by treatment with HCl gas in diethyl ether to yield 170 mg of final product (32%).

$^1$H NMR (DMSO-d6) δ 7.25 (appt, 1H), 7.15–7.17 (m, 1H), 7.10–6.12 (m, 1H), 7.00–7.10 (m, 4H); 3.43–3.45 (m, 2H), 3.22–3.24 (m, 4H), 2.96–3.01 (m, 2H), 2.77–2.78 (s, 3H); MS (posESI) m/z=380.1 (M+H$^+$).

Example 99

3-Amino-N-(2-methoxyphenyl)-4-(4-methyl-1-piperazinyl)benzenesulfonamide hydrochloride (Scheme 5, Method 5)

The compound was prepared from 4-chloro-3-nitrobenzenesulfonylchloride (1 g, 3.9 mmol), 2-methoxyaniline (0.53 mL, 4.7 mmol) and pyridine (1.6 mL) in $CH_2Cl_2$ (2 mL). 4-Chloro-N-(2-methoxyphenyl)-3nitrobenzenesulfonamide (0.345 mg) was reacted with N-methylpiperazine (0.144 mL) to afford N-(2-methoxyphenyl)-4-(4-methyl-1-piperazinyl)-3-nitrobenzenesulfonamide which was treated with Raney-Ni and hydrazine monohydrate. The final product was isolated as its HCl salt $^1$H NMR (DMSO-d6) δ 7.185 (dd, 1H), 7.08 (dt, 1H), 6.975 (d, 1H), 6.91–6.94 (m, 2H); 6.84 (dt, 1H), 3.56 (s, 3H), 3.42–3.47 (m, 2H), 3.22–3.24 (m, 2H), 2.95 (bt, 2H), 2.79 (bs, 3H); MS (posESI) m/z=376.2 (M+H$^+$).

Example 100

3-Amino-N-(2-methoxyphenyl)-4-(1-piperazinyl)benzenesulfonamide hydrochloride (Scheme 5, Method 5)

The compound was prepared from 4-chloro-3-nitrobenzenesulfonyl chloride (1 g, 3.9 mmol), 2-methoxyaniline (0.53 mL, 4.7 mmol) and pyridine (1.6 mL) in $CH_2CL_2$ (2 mL). 4-Chloro-N-(2-methoxyphenyl)-3-nitrobenzenesulfonamide (0.345 g) was reacted with piperazine (0.111 g) to afford N-(2-methoxyphenyl)-4-(piperazinyl)-3-nitrobenzenesulfonamide. This was then treated with Raney-Ni and hydrazine monohydrate. The final product was isolated as its HCl salt. $^1$H NMR (DMSO-d6) δ 7.18–7.20 (m, 1H), 7.08–7.10 (m, 2H), 6.93–6.96 (m, 1H), 6.91–6.93 (m, 2H); 6.84 (dt, 1H), 3.56 (s, 3H), 3.22–3.27 (m, 4H), 3.00–3.02 (m, 4H); MS (posESI) m/z=362.1 (M+H$^+$).

Example 95

2-(1,4-diazepan-1-yl)-5-(4-morpholinylsulfonyl) aniline hydrochloride (Scheme 5, Method 5)

A suspension of homopiperazine (0.196 g, 1.95 mmol), 4-[(4-chloro-3-nitrophenyl)sulfonyl]morpholine (0.461 g, 1.50 mmol) and K$_2$CO$_3$ (0.415 g, 3.00 mmol) in CH$_3$CN (10 mL) was stirred at 65° C. for 16 h. CH$_2$CL$_2$ (10 mL) was added and the mixture was filtered and concentrated. The crude product was purified by column chromatography on silica using CHCl$_3$→CHCl$_3$/10% MeOH+0.4% aqueous ammonia to yield 0.546 g of the product as a yellow solid (yield 98%); $^1$H NMR (CDCl$_3$) δ 8.13–8.07 (m, 1H), 7.70–7.64 (m, 1H), 7.16–7.12 (m, 1H), 3.78–3.73 (m, 4H), 3.55–3.49 (m, 2H), 3.44–3.36 (m, 2H), 3.19–3.13 (m, 2H), 3.06–3.00 (m, 6H), 2.05–1.95 (m, 2H); $^{13}$C NMR (CDCl$_3$) δ 147.88, 137.39, 131.60 127.81, 122.66, 118.02, 66.23, 54.45, 51.02, 49.30, 48.27, 46.16, 29.46; MS (posES-FIA) m/z=372 (M+H$^+$). To a solution of 1-[4-(4-morpholinylsulfonyl)-2-nitrophenyl]-1,4-diazepane (0.445 g, 1.20 mmol) in 30 mL of a 4:1 EtOH:THF solvent system was added Raney-Ni (100 mg suspension in EtOH) followed by hydrazine monohydrate (300 mg, 6.00 mmol). The mixture was stirred vigorously for 4 h and then filtered through celite that was pretreated with water. The filtrate was concentrated, and then re-dissolved in CH$_3$CN, concentrated again and finally toluene was added and the mixture concentrated once more to give a brown solid. The crude product was purified by column chromatography (SiO$_2$, CHCl$_3$/MeOH/NH$_3$ 9:1:0.4%) to give 0.365 g (yield 89%) of the pure product as a solid. The free base was converted to its HCl salt; $^1$H NMR (DMSO-d6) δ 9.34 (s, 2H), 7.23–7.16 (m, 2H), 7.04–6.98 (m, 1H), 3.65–3.60 (m, 4H), 3.35–3.20 (m, 6H), 3.11–3.04 (m, 2H), 2.86–2.80 (m, 4H), 2.09–1.99 (m, 2); MS (posESI) m/z=341 (M+H$^+$).

Intermediate 17

4-Chloro-N-(2-methoxy-phenyl)-3-nitrobenzenesulfonamide (Scheme 5, Method 5)

4-Chloro-3-nitrobenzenesulfonamide (1.73 g, 6.78 mmol) was dissolved in CH$_2$Cl$_2$ (7.0 mL). o-Anisidine (1.00 g, 8.13 mmol) was added dropwise at room temperature, followed by a slow addition of pyridine (2.0 mL). After 16 h of continued stirring, the reaction mixture was diluted with EtOAc (50 mL) and washed with 1 M HCl (3×50 mL). The organic phase was dried (MgSO$_4$) filtered and evaporated to a brown solid, upon which re-crystallization from ethanol/water gave 2.22 g (95%) of the product as white crystals. $^1$H NMR (CDCl$_3$) δ 8.20 (s, 1H), 7.80 (dd, 1H), 7.56 (d, 1H), 7.53 (d, 1H), 7.13 (t, 1H), 6.96 (t, 1H), 6.76 (d, 1H), 3.66 (s, 3H). The sulfonamide proton was not observed.

Intermediate 18

4-Chloro-3-nitro-N-phenyl-benzenesulfonamide (Scheme 5, Method 5)

Two portions of 4-Chloro-3-nitrobenzenesulfonamide (1.73 g, 6.78 mmol) were dissolved in CH$_2$Cl$_2$ (7.0 mL) in reaction flasks. Aniline (757 mg, 8.13 mmol) was added drop-wise at room temperature, followed by slow additions of pyridine (2.0 mL). After 16 h of continued stirring, the reaction mixtures were diluted with ethyl acetate (50 mL) and washed with 1 M HCl (3×50 mL). The organic phases were dried (MgSO$_4$) and evaporated to brown solids, which upon re-crystallization from ethanol/water gave off-white solid of the product 2.04 g (96%): $^1$H NMR (CDCl$_3$, 400 MHz) δ 8.24 (d, 1H), 7.80 (dd, 1H), 7.61 (d, 1H), 7.30 (t, 2H), 7.20 (t, 1H), 7.09 (d, 2H), 6.79 (bs, 1H); MS (CI) 310.8 (M−H)$^−$; Purity (HPLC, Hichrom 200×4.6 mm I.D.)>98%.

General procedure for reactions between 4-Chloro-3-nitro-N-aryl-benzenesulfonamides and amines (R$^5$) (Scheme 5, Method 5)

Solutions of Intermediate 17 (343 mg, 1.00 mmol) and Intermediate 12 (313 mg, 1.00 mmol) in CH$_3$CN (5 mL) were treated with K$_2$CO$_3$ (276 mg, 2.00 mmol) and amines (R$^5$) (1.30 mmol) and heated to 80° C. for 16 h. The reaction mixtures were diluted with ethyl acetate (50 mL), washed with saturated Na$_2$CO$_3$ (3×50 mL), dried (Na$_2$SO$_4$) and evaporated to products that could be used for the next step without purification.

Intermediate 19

N-(2-Methoxyphenyl)-4-(3-methyl-piperazin-1-yl)-3-nitrobenzenesulfonamide (Scheme 5, Method 5)

A solution of Intermediate 17 (343 mg, 1.00 mmol) and K$_2$CO$_3$ (276 mg, 2.00 mmol) in CH$_3$CN (5 mL) was treated with 2-methylpiperazine (130 mg, 1.30 mmol). After 16 h of stirring at 80° C., the reaction mixture was diluted with EtOAc (50 mL) and washed with saturated Na$_2$CO$_3$ (aq) (3×50 mL). The organic phases were dried (Na$_2$SO$_4$) and evaporated to give 398 mg of a yellow foam of the title compound (98%). $^1$H NMR (CDCl$_3$) δ 8.16 (d, 1H), 7.70 (dd, 1H), 7.50 (d, 1H), 7.06 (t, 1H), 6.97 (d, 1H), 6.91 (t, 1H), 6.75 (d, 1H), 3.69 (s, 3H), 2.92–3.17 (m, 6H), 2.61 (t, 1H), 1.05 (d, 3H). The sulfonamide and amine protons were not observed.

Intermediate 20

4-(Hexahydro-pyrrolo[1,2-a]pyrazin-2-yl)-N-(2-methoxyphenyl)-3-nitro-benzenesulfonamide (Scheme 5, Method 5)

A solution of Intermediate 17 (343 mg, 1.00 mmol) and K$_2$CO$_3$ (276 mg, 2.00 mmol) in CH$_3$CN (5 mL) was treated with octahydropyrrolo[1,2-a]pyrazine (164 mg, 1.30 mmol). After 16 h of stirring at 80° C., the reaction mixture was diluted with EtOAc (50 mL) and washed with saturated Na$_2$CO$_3$ (3×50 mL). The organic phases were dried (Na$_2$SO$_4$) and evaporated to give 407 mg a yellow foam of the title compound (94%). $^1$H NMR (CDCl$_3$) δ 8.16 (s, 1H), 7.70 (dd, 1H), 7.50 (d, 1H), 7.06 (t, 1H), 7.00 (d, 1H), 6.91 (t, 1H), 6.75 (d, 1H), 3.69 (s, 3H), 3.02–3.33 (m, 5H), 2.80 (t, 1H), 2.39 (t, 1H), 2.18–2.22 (m, 2H), 1.76–1.85 (m, 3H), 1.37–1.40 (m, 1H). The sulfonamide and amine protons were not observed.

Intermediate 21

3-Nitro-N-phenyl-4-piperazin-1-yl-benzenesulfonamide (Scheme 5, Method 5)

The compound was prepared from Intermediate 18 and piperazine to give 362 mg bright orange solid (100%): $^1$H NMR (CDCl$_3$, 400 MHz) δ 8.16 (d, 1H), 7.68 (d, 1H), 7.27 (t, 2H), 7.15 (t, 1H), 7.08 (d, 2H), 7.01 (d, 1H), 3.13 (t, 4H), 2.98 (t, 4H); MS (CI) 362.8 (M+H)$^+$ 361.2 (M−H)$^-$; Purity (HPLC, Hichrom 200×4.6 mm I.D.) 91%.

Intermediate 22

4-(3-Methyl-piperazin-1-yl)-3-nitro-N-phenyl-benzenesulfonamide (Scheme 5, Method 5)

The compound was prepared from Intermediate 18 and 1-methylpiperazine to give 373 mg orange-brown solid (99%): $^1$H NMR (CDCl$_3$, 400 MHz) δ 8.17 (s, 1H), 7.68 (d, 1H), 7.27 (t, 2H), 7.15 (t, 1H), 7.08 (d, 2H), 7.00 (d, 1H), 3.14–3.22 (m, 2H), 2.97–3.06 (m, 4H), 2.64 (dd, 1H), 1.06 (d, 3H); MS (CI) 391.0 (M+H)$^+$ 389.4 (M−H)$^-$; Purity (HPLC, Hichrom 200×4.6 mm I.D.)>95%.

Intermediate 23

4-(4-Ethyl-piperazin-1-yl)-3-nitro-N-phenyl-benzenesulfonamide (Scheme 5, Method 5)

The compound was prepared from Intermediate 18 and 1-ethylpiperazine to give 386 mg orange foam (99%): $^1$H NMR (CDCl$_3$, 400 MHz) δ 8.19 (s, 1H), 7.72 (dd, 1H), 7.31 (t, 2H), 7.18 (t, 1H), 7.11 (d, 2H), 7.04 (d, 1H), 3.22 (bs, 4H), 2.60 (bs, 4H), 2.50 (q, 2H), 1.13 (t, 3H); MS (CI) 377.0 (M+H)$^+$ 375.4 (M−H)$^-$; Purity (HPLC, Hichrom 200×4.6 mm I.D.)>98%.

Intermediate 24

4-(Hexahydro-pyrrolo[1,2-a]pyrazin-2-yl)-3-nitro-N-phenyl-benzenesulfonamide (Scheme 5, Method 5)

The compound was prepared from Intermediate 18 and hexahydro-pyrrolo[1,2-a]2-pyrazine 372 mg orange foam (92%): $^1$H NMR (CDCl$_3$, 400 MHz) δ 8.16 (s, 1H), 7.67 (d, 1H), 7.27 (t, 2H), 7.14 (t, 1H), 7.08 (d, 2H), 7.03 (d, 1H), 3.02–3.35 (m, 5H), 2.83 (dd, 1H), 2.41 (t, 1H), 2.18–2.25 (m, 2H), 1.72–1.85 (m, 3H), 1.32–1.43 (m, 1H); MS (CI) 403.2 (m+H)$^+$ 401.0 (M−H)$^-$; Purity (HPLC, Hichrom 200×4.6 mm I.D.)>95%.

Intermediate 25

4-(5-Methyl-2,5-diaza-bicyclo[2.2.1]hept-2-yl)-3-nitro-N-phenyl-benzenesulfonamide (Scheme 5, Method 5)

The compound was prepared from Intermediate 18 and 5-methyl-2,5-diaza-bicyclo[2.2.1]2-heptane to give 374 mg yellow solid (96%): $^1$H NMR (CDCl$_3$, 400 MHz) δ 8.12 (d, 1H), 7.58 (d, 1H), 7.26 (t, 2H), 7.13 (t, 1H), 7.07 (d, 2H), 6.76 (d, 1H), 4.24 (bs, 1H), 3.46–3.49 (m, 2H), 2.88 (d, 1H), 2.80 (t, 2H); 2.33 (s, 3H), 1.89 (d, 1H), 1.53 (bs, 1H); MS (CI) 389.0 (M+H)$^+$ 387.0 (M−H)$^-$; Purity (HPLC, Hichrom 200×4.6 mm I.D.)>95%.

Intermediate 26

4-(trans-2,5-Dimethyl-piperazin-1-yl)-N-(2-methoxyphenyl)-3-nitro-benzenesulfonamide (Scheme 5, Method 5)

The compound was prepared from Intermediate 17 and 4-(trans-2,5-dimethyl-piperazine to give 409 mg of yellow solid resulted (97%): $^1$H NMR (CDCl$_3$, 400 MHz) δ 7.94 (d, 1H), 7.76 (dd, 1H), 7.50 (dd, 1H), 7.28 (d, 1H), 7.10 (t, 1H), 6.93 (t, 1H), 6.73 (d, 1H), 2.93–3.08 (m, 4H), 2.60 (dd, 1H), 2.31 (dd, 1 H), 1.01 (d, 3H), 0.73 (d, 3H); MS (CI) 420.8 (M+H)$^+$ 418.8 (M−H)$^-$; Purity (HPLC, Hichrom 200×4.6 mm I.D.)>95%.

General Procedure for Reduction of the Amino Groups (Scheme 5, Method 5)

Solutions of the nitro compounds (0.25 mmol) in THF (10 mL) and methanol (2 mL) were treated with Raney-Ni (100 mg) and hydrazine monohydrate (120 μl, 2.5 mmol). After stirring at room temperature for 7 h, the suspensions were filtered through celite and washed with ethyl acetate and ethanol. Evaporation with HCl in ether gave the products. Some of the products were without impurities, others had to be purified with HPLC ((YMC combiprep ODS-AQ, 50×20 mm I.D.).

Example 101

3-Amino-N-(2-methoxyphenyl)-4-(3-methyl-piperazin-1-yl)-benzenesulfonamide (Scheme 5, Method 5)

The compound was prepared from N-(2-methoxyphenyl)-4-(3-methylpiperazin-1-yl)-3-nitro-benzenesulfonamide to give 90 mg of the title compound (96%). $^1$H NMR (CDCl$_3$) δ 7.44 (d, 1H), 7.11 (d, 1H), 7.10 (d, 1H), 6.97 (t, 1H), 6.85 (d, 1H), 6.84 (t, 1H), 6.72 (d, 1H), 3.97 (bs, 2H), 3.62 (s, 3H), 2.91–3.06 (m, 5H), 2.56 (t, 1H), 2.23 (t, 1H), 1.41 (s, 1H), 1.05 (d, 3H). The sulfonamide protons were not observed. $^{13}$C NMR (CDCl$_3$) δ 149.4, 143.1, 141.4, 134.6, 125.4, 124.4, 121.0, 120.4, 119.2, 117.7, 113.2, 110.5, 55.6, 51.1, 50.8, 46.3, 30.3, 19.6. MS (CI neg) 375 (M−H$^+$), (CI pos) 377 (M+H$^+$).

Example 102

3-Amino-4-(hexahydro-pyrrolo[1,2-a]pyrazin-2-yl)-N-(2-methoxyphenyl)-benzenesulfonamide (Scheme 5, Method 5)

The compound was prepared from 4-(hexahydro-pyrrolo [1,2-a]pyrazin-2-yl)-N-(2-methoxyphenyl)-3-nitrobenzenesulfonamide to give 97 mg of the title compound (96%). $^1$H NMR (CDCl$_3$) δ 7.44 (d, 1H), 7.12 (d, 1H), 7.11 (d, 1H), 6.97 (t, 1H), 6.90 (d, 1H), 6.84 (t, 1H), 6.72 (d, 1H), 3.96 (bs, 2H), 3.62 (s, 3H), 3.19 (d, 1H), 3.09 (app t, 3H), 2.76 (t, 1H), 2.45 (t, 1H), 2.31–2.38 (m, 1H), 2.10–2.21 (m, 2H), 1.72–1.87 (m, 3H), 1.21 (t, 1H). The sulfonamide protons were not observed. $^{13}$C NMR (CDCl$_3$) δ 149.4, 143.1, 141.4, 134.4, 125.4, 124.7, 121.0, 120.5, 119.5, 117.7, 113.2, 110.5, 55.6, 55.0, 53.3, 52.0, 49.7, 30.3, 27.3, 21.2. MS (CI neg) 401 (M−H$^+$).

Example 103

3-Amino-N-phenyl-4-piperazin-1-yl-benzenesulfonamide hydrochloride (Scheme 5, Method 5)

The compound was prepared from N-phenyl-4-piperazin-1-yl-3-nitro benzenesulfonamide to give 15 mg yellow solid (18%): ¹H NMR (MeOD, 400 MHz) δ 7.57–7.61 (m, 2H), 7.40 (d, 1H), 7.23 (t, 2H), 7.13 (d, 2H), 7.07 (t, 1H), 3.45 (t, 4H), 3.20 (t, 4H); MS (CI) 333.0 (M+H)⁺ 331.4 (M–H)⁻; Purity (HPLC, Hichrom 200×4.6 mm I.D.) 96%.

Example 104

3-Amino-4-(3-methyl-piperazin-1-yl)-N-phenyl-benzenesulfonamide hydrochloride (Scheme 5, Method 5)

The compound was prepared from 4-(3-methyl-piperazin-1-yl)-N-3-nitrophenyl-benzenesulfonamide to give 33 mg white solid (35%): ¹H NMR (MeOD, 400 MHz) δ 7.57–7.62 (m, 2H), 7.35–7.41 (m, 1H), 7.12 (t, 2H), 7.02 (d, 2H), 6.97 (t, 1H), 3.53–3.58 (m, 1H), 3.31–3.40 (m, 2H), 3.16 (t, 2H), 2.99–3.05 (m, 1H), 2.79 (t, 1H), 1.27 (d, 3H); MS (CI) 346.8 (M+H)⁺ 345.4 (M–H)⁻; Purity (HPLC, Hichrom 200×4.6 mm I.D.) 100%.

Example 105

3-Amino-4-(4-ethyl-piperazin-1-yl)-N-phenyl-benzenesulfonamide hydrochloride (Scheme 5, Method 5)

The compound was prepared from 3-Amino-4-(4-ethyl-piperazin-1-yl)-N-phenyl-benzenesulfonamide to give 32 mg white solid (33%): ¹H NMR (MeOD, 400 MHz) δ 7.52–7.57 (m, 2H), 7.36 (d, 1H), 7.12 (t, 2H), 7.01 (d, 2H), 6.96 (t, 1H), 3.56 (d, 2H), 3.26 (t, 2H), 3.17–3.23 (m, 4H), 3.09 (t, 2H), 1.31 (t, 3H); MS (CI) 361.0 (M+H)⁺ 359.4 (M–H)⁻; Purity (HPLC, Hichrom 200×4.6 mm I.D.) 96%.

Example 106

3-Amino-4-(hexahydro-pyrrolo[1,2-a]pyrazin-2-yl)-N-phenyl-benzenesulfonamide hydrochloride (Scheme 5, Method 5)

The compound was prepared from 4-(hexahydro-pyrrolo[1,2-a]pyrazin-2-yl)-N-phenyl-3-nitro-benzenesulfonamide to give 50 mg white solid (49%): ¹H NMR (MeOD, 400 MHz) δ 7.63–7.69 (m, 2H), 7.47–7.52 (m, 1H), 7.23 (t, 2H), 7.13 (d, 2H), 7.08 (t, 1H), 3.08–3.78 (m, 8H), 2.12–2–35 (m, 4H), 1.79–1.88 (m, 1H); MS (CI) 372.8 (M+H)⁺ 371.4 (M–H)⁻; Purity (HPLC, Hichrom 200×4.6 mm I.D.) 100%.

Example 107

3-Amino-4-(5-methyl-2,5-diaza-bicyclo[2.2.1]hept-2-yl)-N-phenyl-benzenesulfonamide hydrochloride (Scheme 5, Method 5)

The compound was prepared from 4-(5-methyl-2,5-diaza-bicyclo[2.2.1]hept-2-yl)-N-phenyl-3-nitrobenzenesulfonamide to give 40 mg red solid (40%): ¹H NMR (MeOD, 400 MHz, major conformer at 300 K) δ 7.49–7.56 (m, 2H), 7.09–7.15 (m, 3H), 6.99–7.05 (m, 2H), 6.95 (t, 1H), 4.39 (bs, 1H), 4.30 (bs, 1H), 3.89 (d, 1H), 3.56 (bs, 2H), 3.09 (d, 1H), 2.88 (s, 3H), 2.34 (d, 1H), 2.20 (d, 1H); MS (CI) 359.0 (M+H)⁺ 357.4 (M–H)⁻; Purity (HPLC, Hichrom 200×4.6 mm I.D.) 93%.

Example 108

3-Amino-4-(trans-2,5-dimethyl-piperazin-1-yl)-N-(2-methoxy-phenyl)-benzenesulfonamide hydrochloride (Scheme 5, Method 5)

The compound was prepared from 4-(trans-2,5-dimethyl-piperazin-1-yl)-N-(2-methoxy-phenyl)-3-nitrobenzenesulfonamide to give 60 mg white solid (61%): ¹H NMR (MeOD, 400 MHz) δ 7.54–7.58 (m, 2H), 7.45 (d, 1H), 7.32 (d, 1H), 7.02 (t, 1H), 6.81 (d, 1H), 6.76 (t, 1H), 3.54–3.57 (m, 1H), 3.47 (s, 3H), 3.37 (d, 1H), 3.30–3.34 (m, 1H), 3.01 (t, 2H), 2.71 (t, 1H), 1.23 (d, 3H), 0.77 (d, 3H); MS (CI) 390.8 (M+H)⁺ 389.4 (M–H)⁻; Purity (HPLC, Hichrom 200× 4.6 mm I.D.) 96%.

Example 112

4-[4-(3,4-Dihydro-2H-quinoline-1-sulfonyl)-2-amino-phenyl]-[1,4]diazepane ditrifluoroacetic acid (Scheme 5, Method 5)

The compound was prepared from 1,2,3,4-tetrahydroquinoline 4-chloro-3-nitro-benzenesulfonyl chloride and [1,4]diazepane-1-carboxylic acid tert-butyl ester (430 μl, 2.2 mmol) to give (63%) as a solid. ¹H NMR (CD₃OD) δ 7.69–7.62 (m, 1H), 7.16–6.98 (m, 5H), 6.94–6.89 (m, 1H), 3.78–3.71 (m, 2H), 3.46–3.27 (m, 6H), 3.13–3.06 (m, 2H), 2.48–2.40 (m, 2H), 2.16–2.05 (m, 2H), 1.69–1.58 (m, 2H); MS m/z (M+1) 387.

Example 109

2-(3-Amino-4-[1,4]diazepan-1-yl-benzenesulfonyl)-benzamide diacetic acid (Scheme 5, Method 5)

The compound was prepared from 2-amino-benzamide, 4-chloro-3-nitro-benzenesulfonyl chloride and 1,4]diazepane-1-carboxylic acid tert-butyl to give (1%) as an oil. ¹H NMR (CD₃OD) δ 7.68–7.57 (m, 2H), 7.43–7.36 (m, 1H), 7.17–7.15 (m, 1H), 7.10–7.02 (m, 3H), 3.44–3.25 (m, 6H), 3.12–3.05 (m, 2H), 2.14–2.02 (m, 2H); MS m/z (M+1H) 390.

Example 111

2-[1,4]Diazepan-1-yl-5-(3,4-dihydro-1H-isoquinoline-2-sulfonyl)-aniline dihydrochloride (Scheme 5, Method 5)

The compound was prepared from 1,2,3,4-tetrahydroisoquinoline, 4-chloro-3-nitro-benzenesulfonyl chloride and 1,4]diazepane-1-carboxylic acid tert-butyl ester to give (93%) as a white solid. ¹H NMR (DMSO) δ 9.28 (s, 2 H), 7.12 (m, 7 H), 4.12 (s, 2 H), 3.20 (m, 8H), 3.02 (t, J=5.81 Hz, 2 H), 2.86 (t, J=6.07 Hz, 2 H), 2.00 (m, 2 H); MS m/z 387 (M+1).

Example 110

4-[4-(3-Fluoro-2-methoxy-phenylsulfamoyl)-2-amino-phenyl]-[1,4]diazepane ditrifluoroacetic acid (Scheme 5, Method 5)

The compound was prepared from 3-fluoro-2-methoxyaniline, 4-chloro-3-nitro-benzenesulfonyl chloride and 1,4]diazepane-1-carboxylic acid tert-butyl ester to give (43%) as a solid. ¹H NMR (DMSO) δ 9.70 (s, 1H), 8.79 (br s, 2H), 7.17–6.87 (m, 6H), 3.53 (s, 3H), 3.32–3.13 (m, 6H), 2.99–2.91 (m, 2H), 2.01–1.89 (m, 2H); MS m/z (M+1) 395.

Scheme 6, Method 6

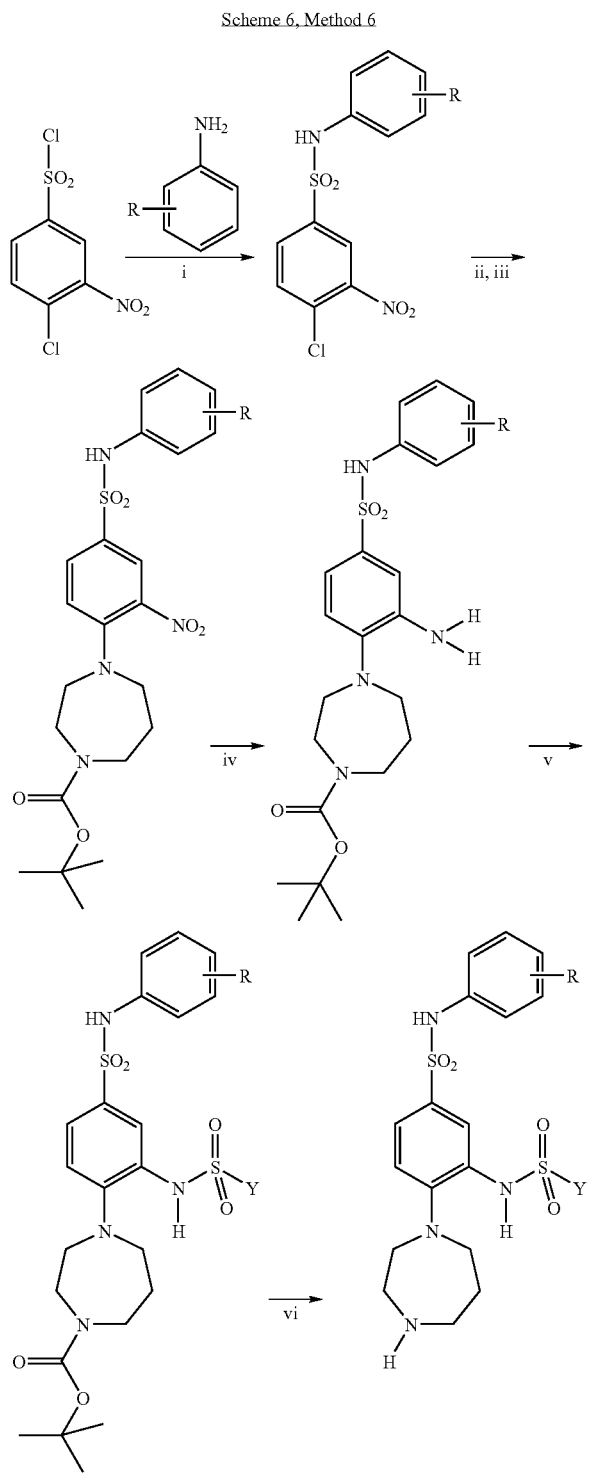

Legend to Scheme 2:
 i: Py, CH$_2$CL$_2$; ii: K$_2$CO$_3$, CH$_3$CN, diamine (i. e. homopiperazine); iii: (BOC)$_2$O, THF, NaOH; iv: Raney-Ni, Hydrazine monohydrate, THF/EtOH; v: sulfonylchloride (Y—SO$_2$—Cl), Py, Et$_3$N, CH$_2$CL$_2$; vi: HCl ether/MeOH Intermediate 27 tert-Butyl-4-[4-(anilinosulfonyl)-2-nitrophenyl]-1,4-diazepane-1-carboxylate (Scheme 6, Method 6)

Di-tert-butyl dicarbonate (0.921 g, 4.22 mmol) in THF (20.0 mL) was added to a solution of 4-(1,4-diazepan-1-yl)-3-nitro-N-phenylbenzenesulfonamide (0.530 g, 1.40 mmol) and NaOH (0.140 g, 3.50 mmol) dissolved in THF:water (30 mL, 1:1). The solution was stirred at room temperature for 3 h. The mixture was neutralized with 5 N HCl and then the THF was removed under vacuum. The aqueous phase was extracted with CHCl$_3$ (2×50 mL) and the combined organic layers were dried over Na$_2$SO$_4$, filtered and concentrated. Purification via flash column chromatography (SiO$_2$, using CHCl$_3$/MeOH/9.75:0.25) gave a solid, which was triturated with EtOAc/pentane to give 0.605 g (90%) of the pure product. $^1$H NMR (DMSO-d6) δ 9.84 (br s, 1H), 8.01–7.98 (m, 1H), 7.70–7.65 (m, 1H), 7.32–7.28 (m, 1H), 7.26–7.20 (m, 2H), 7.13–7.08 (m, 2H), 7.07–7.02 (m, 1H), 3.61–3.48 (m, 4H), 3.39–3.33 (m, 2H), 3.23–3.15 (m, 2H), 1.85–1.76 (m, 2H), 1.18 (s, 9H); MS (posESI-FIA) m/z=477 (M+H$^+$).
tert-Butyl-4-[2-nitro-4-(anilinosulfonyl)phenyl]-1,4-diazepane-1-carboxylate was reduced to the final product by treatment with Raney-Ni and hydrazine monohydrate using method C to yield 0.477 g (91%) of the free base; $^1$H NMR (DMSO-d6) δ 9.81 (s, 1H), 7.24–7.18 (m, 2H), 7.13–7.08 (m, 3H), 7.02–6.92 (mn, 3H), 4.99 (m, 2H), 3.53–3.45 (m, 4H), 3.02–2.94 (m, 4H), 1.86–1.79 (m, 2H), 1.42 (9H); MS (posESI-FIA) m/z=447 (M+H$^-$).

Example 97

4-(1,4-Diazepan-1-yl)-N-phenyl-3-[(methylsulfonyl)amino]benzenesulfonamide hydrochloride (Scheme 6, Method 6)

A mixture of tert-butyl 4-[2-amino-4-(anilinosulfonyl)phenyl]-1,4-diazepane-1-carboxylate (176 mg, 0.39 mmol), methylsulfonyl chloride (0.040 mL, 0.47 mmol) and pyridine (0.285 mL, 3.51 mmol) in CH$_2$CL$_2$ (5 mL) was stirred at room temperature overnight. The reaction mixture was quenched with NaHCO$_3$ aq (3×30 mL). The organic phase was separated, dried (MgSO$_4$) and filtered. The volatiles were evaporated followed by purification of the oily residue by chromatography (SiO$_2$, hexane/EtOAc 4:1) to give 110 mg of tert-butyl 4-{4-(anilinosulfonyl)-2-[(methylsulfonyl)amino]phenyl}-1,4-diazepane-1-carboxylate (yield 58%).

$^1$H NMR (CDCl$_3$) δ 7.90–7.85 (m, 1H), 7.50–7.43 (m, 1H), 7.30–7.24 (m, 2H), 7.20–7.08 (m, 4H), 6.84–6.79 (m, 1H), 3.65–3.51 (m, 4H), 3.12–3.06 (m, 1H), 3.04–2.96 (m, 6H), 2.04–1.91 (m, 2H), 1.49 (s, 3H); MS (posEI-DIP) m/z=524 (M+H$^+$).

tert-Butyl 4-{4-(anilinosulfonyl)-2-[(methylsulfonyl)amino]phenyl}-1,4-diazepane-1-carboxylate (0.077 g, 0.147 mmol) was dissolved in MeOH, and ether saturated with HCl gas was added. The mixture was stirred at room temperature for 4 h and then concentrated. The crude solid was dissolved in a small amount of MeOH, and ether was added. The precipitate was collected and dried to give 30 mg of the pure product as the HCl salt (yield 48%): $^1$H NMR (DMSO-d6) δ 7.72–7.70 (m, 1H), 7.46–7.42 (m, 1H), 7.25–7.20 (m, 3H), 7.14–7.09 (m, 2H), 7.03–6.99 (m, 1H), 3.45–3.15 (m, partly obscured by solvent signal, HDO, 6H), 2.96 (s, 3H), 2.02–1.95 (m, 2H); MS (posES-FIA) m/z=425 (M+H$^+$).

Example 96

4-(1,4-Diazepan-1-yl)-N-phenyl-3-[(phenylsulfonyl)amino]benzenesulfonamide hydrochloride (Scheme 6, Method 6)

To a solution of tert-butyl 4-[2-amino-4-(anilinosulfonyl)phenyl]-1,4-diazepane-1-carboxylate (0.268 g g, 0.599 mmol), pyridine (338 µL, 4.19 mmol) and Et$_3$N (337 µL, 2.40 mmol), in CH$_2$Cl$_2$ (8.0 mL) was added benzenesulfonyl chloride (153 µL, 1.20 mmol) in CH$_2$Cl$_2$ (2 mL). The mixture was stirred at room temperature for 16 h. The reaction mixture was washed with saturated aqueous NaHCO$_3$, dried with Na$_2$SO$_4$, filtered and concentrated. The crude material was dissolved in EtOH (5 mL) and KOH (0.134 g, 4.0 equiv.) was added. The reaction was stirred at room temperature for 2 days. Water (5 mL) was added to the reaction mixture and most of the EtOH was evaporated under vacuum. The water phase was extracted with CH$_2$Cl$_2$ (3×20 mL). The combined organic phases were dried with Na$_2$SO$_4$, filtered and concentrated. The crude boc-protected material was dissolved in MeOH, and ether saturated with HCl gas was added. The mixture was stirred for 16 h and then concentrated to give 0.543 g of the crude product, which was purified by reversed phase preparative HPLC to give 0.153 g of the pure product as the acetic acid salt which was converted to the HCl-salt: $^1$H NMR (DMSO-d6) δ 10.25 (s, 1H), 9.09 (br s, 2H), 7.68–7.58 (m, 4H), 7.54–7.48 (m, 2H), 7.46–7.42 (m, 1H), 7.23–7.16 (m, 3H), 7.05–6.28 (m, 3H), 3.35–3.15 (m, partly obscured by solvent signal HDO, 6H), 2.81–2.75 (m, 2H), 1.92–1.85 (m, 2H); MS (posES-FIA) m/z=487 (M+H$^+$).

Intermediate 28

N-Naphthalen-1-yl-3-nitro-4-piperazin-1-yl-benzenesulfonamide, hydrochloride 4-Chloro-3-nitrobenzenesulphonyl chloride (0.992 g, 3.87 mmol) was added to a solution of naphthalen-1-ylamine (0.665 g, 4.64 mmol) and pyridine (3.1 mL, 38.7 mmol) dissolved in DCM (5 mL). The solution was stirred at room temperature for 2 days and the volatiles were evaporated. The crude mixture was dissolved in EtOAc and the organic phase was washed with 1 N HCl, dried with MgSO$_4$, filtered and concentrated to give 1.1 g of naphthalen-1-yl-3-nitro-4-chloro-benzenesulfonamide. Naphthalen-1-yl-3-nitro-4-chloro-benzenesulfonamide was dissolved in CH$_3$CN (10 mL) and piperazine (0.683 g, 7.93 mmol) was added. The mixture was stirred at 65° C. for 16 hours. The mixture was concentrated and the crude product was purified by flash chromatography on silica using DCM→DCM/MeOH (10%)+aqueous NH$_3$ (0.4 as eluent to give 0.531 g of the free base which was converted to its HCl-salt.

$^1$H NMR (DMSO-d$_6$) δ 10.36 (brs, 1H), 9.33 (brs, 2H), 8.12 (D, J=2.1 Hz, 1H), 8.05–7.99 (m, 1H), 7.94–7.88 (m, 1H), 7.85–7.72 (m, 2H), 7.55–7.38 (m, 4H), 7.22–7.16 (m, 1H), 3.40–3.30 (m, obscured by solvent signal, 4H), 3.24–3.12 (m, 4H); MS (posES-FIA) m/z=413 (M+H).

Example 113

3-Amino-2-chloro-N-naphthalen-1-yl-4-piperazin-1-yl-benzenesulfonamide, hydrochloride To a solution of N-naphthalen-1-yl-3-nitro-4-piperazin-1-yl-benzenesulfonamide (0.4602 g, 11.2 mmol) in 40 mL of a 4:1 EtOH:THF solvent system was added Raney-Ni (~1.0 mL suspension in EtOH) followed by hydrazine monohydrate (2.80 g, 56.0 mmol). The mixture was stirred vigorously for 3 hours and then filtered through celite. The filtrate was concentrated and the crude product was triturated with MeOH/ether. The product was converted to its HCl-salt. Yield (90%) as the free base. An aliquot was purified by preparative LC/MS.

$^1$H NMR (DMSO-d6) δ 9.20–8.90 (brs 2H), 8.25–8.21 (m, 1H), 7.90–7.86 (m, 1H), 7.74 (d, J=8.48 Hz, 1H), 7.52–7.46 (m, 2H), 7.39–7.35 (m, 1H), 7.24–7.21 (m, 1H), 7.10 (d, J=8.48 Hz, 1H), 6.91 (m, d, J=8.48 Hz, 1H), 3.32–3.25 (m,, obscured by solvent signal, 4H), 3.03–2.98 (m, 4H); MS (posES-FIA) m/z=383.

Biological Tests

The ability of a compound according to the invention to bind a 5-HT$_6$ receptor, and to be pharmaceutically useful, can be determined using in vivo and in vitro assays known in the art.

(a) 5-HT$_6$ Intrinsic Activity Assay

Antagonists to the 5-HT$_6$ receptor were characterized by measuring inhibition of 5-HT induced increase in cAMP in HEK 293 cells expressing the human 5-HT$_6$ receptor (see Boess et al. (1997) Neuropharmacology 36: 713–720). Briefly, HEK293/5-HT$_6$ cells were seeded in polylysine coated 96-well plates at a density of 25,000/well and grown in DMEM (Dulbecco's Modified Eagle Medium) (without phenol-red) containing 5% dialyzed Foetal Bovine Serum for 48 h at 37° C. in a 5% CO$_2$ incubator. The medium was then aspirated and replaced by 0.1 ml assay medium (Hanks Balance Salt Solution containing 20 mM HEPES, 1.5 mM isobutylmethylxanthine and 1 mg/ml bovine serum albumin). After addition of test substances, 50 µl dissolved in assay medium, the cells were incubated for 10 min at 37° C. in a 5% CO$_2$ incubator. The medium was again aspirated and the cAMP content was determined using a radioactive cAMP kit (Amersham Pharmacia Biotech, BIOTRAK RPA559). The potency of antagonists was quantified by determining the concentration that caused 50% inhibition of 5-HT (at [5-HT]=8 times EC$_{50}$) evoked increase in cAMP, using the formula $K_{i,eff}=IC_{50}/(1+[5HT]/EC_{50})$.

The compounds in accordance with the invention have a selective affinity to 5-HT$_6$ receptors with $K_i$ values between 1 nM and 5 µM and they antagonized the 5-HT indiced increase of cAMP. There is correlation between the $K_i$ binding and the $K_{i,efficacy}$. Moreover, the compounds show good selectivity (>100 fold) against 5-HT$_{2a}$, 5-HT$_{2b}$, 5-HT$_{2c}$, 5-HT$_{1a}$, 5HT$_{1b}$.

(b) In vivo Assay of Reduction of Food Intake

For a review on serotonin and food intake, see Blundell, J. E. and Halford, J. C. G. (1998) Serotonin and Appetite Regulation. Implications for the Pharmacological Treatment of Obesity. CNS Drugs 9:473–495.

Obese (ob/ob) mouse is selected as the primary animal model for screening as this mutant mouse consumes high amounts of food resulting in a high signal to noise ratio. To further substantiate and compare efficacy data, the effect of the compounds on food consumption is also studied in wild type (C57BL/6J) mice. The amount of food consumed during 15 hours of infusion of compounds is recorded.

Male mice (obese C57BL/6JBom-Lep$^{ob}$ and lean wild-type C57B1/6JBom; Bomholtsgaard, Denmark) 8–9 weeks with an average body weight of 50 g (obese) and 25 g (lean) are used in all the studies. The animals are housed singly in cages at 23±1° C., 40–60% humidity and have free access to water and standard laboratory chow. The 12/12-h light/dark cycle is set to lights off at 5 p.m. The animals are conditioned for at least one week before start of study.

The test compounds are dissolved in solvents suitable for each specific compound such as cyclodextrin, cyclodextrin/methane sulfonic acid, polyethylene glycol/methane sulfonic acid, saline. Fresh solutions are made for each study. Doses of 30, 50 and 100 mg kg$^{-1}$ day$^{-1}$ are used. The purity of the test compounds is of analytical grade.

The animals are weighed at the start of the study and randomized based on body weight. Alzet osmotic minipumps (Model 2001D; infusion rate 8 μl/h) are used and loaded essentially as recommended by the Alzet technical information manual (Alza Scientific Products, 1997; Teeuwes and Yam, 1976). Continuous subcutaneous infusion with 24 hours duration is used. The minipumps are either filled with different concentrations of test compounds dissolved in vehicle or with only vehicle solution and maintained in vehicle pre-warmed to 37° C. (approx. 1 h). The minipumps are implanted subcutaneously in the neck/back region under short acting anesthesia (metofane/enflurane). This surgical procedure lasts approximately 5 min. It takes about 3 h to reach steady state delivery of the compound.

The weight of the food pellets are measured at 5 p.m. and at 8 p.m. for two days before (baseline) and one day after the implantation of the osmotic minipumps. The weigh-in is performed with a computer assisted Mettler Toledo PR 5002 balance. Occasional spillage is corrected for. At the end of the study the animals are killed by neck dislocation and trunk blood sampled for later analysis of plasma drug concentrations.

The plasma sample proteins are precipitated with methanol, centrifuged and the supernatant is transferred to HPLC vials and injected into the liquid chromatography/mass spectrometric system. The mass spectrometer is set for electrospray positive ion mode and Multiple Reaction Monitoring (MRM with the transition m/z 316⇒221).

A linear regression analysis of the standards forced through the origin is used to calculate the concentrations of the unknown samples.

Food consumption for 15 hours is measured for the three consecutive days and the percentage of basal level values is derived for each animal from the day before and after treatment. The values are expressed as mean ±SD and ±SEM from eight animals per dose group. Statistical evaluation is performed by Kruskal-Wallis one-way ANOVA using the percent basal values. If statistical significance is reached at the level of p<0.05, Mann-Whitney U-test for statistical comparison between control and treatment groups is performed.

The compounds according to the invention show an effect in the range of 50–150 mg/kg.

TABLE VII

| EXAMPLE | Dose (mg/Kg) | Reduction of Food Intake (%) po administration |
|---|---|---|
| 27 | 50 | 28 |
| 29 | 100 | 60 |

What is claimed is:
1. A compound of the formula (I)

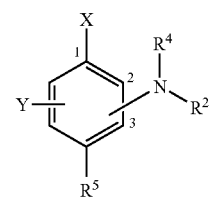

or a pharmaceutically acceptable salt thereof, wherein
X is

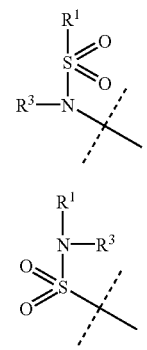

$R^1$ and $R^3$ are independently
(a) H
(b) $C_{1-6}$ alkyl,
(c) $C_{1-6}$ alkoxy,
(d) straight or branched $C_{1-6}$ hydroxyalkyl,
(e) straight or branched $C_{1-6}$ alkylhalides; or
(f) a group Ar;
Ar is
(a) phenyl,
(b) 1-naphthyl,
(c) 2-naphthyl,
(d) benzyl,
(e) cinnamoyl,
(f) a 5 to 7-membered, partially or completely saturated, heterocyclic ring containing 1 to 4 heteroatoms, selected from oxygen, nitrogen and sulfur, or
(g) a bicyclic ring system consisting of two heterocyclic rings as defined under (f), or a bicyclic ring system consisting of one benzene ring and one heterocyclic ring as defined under (f);
alternatively, $R^1$ and $R^3$ are linked to form a group $(CH_2)_2O$, $(CH_2)_4O$, or $(CH_2)_{3-5}$ in formula (Ib);
optionally, the group Ar is substituted with
(a) Y, or
(b) a 5 to 7-membered, partially or completely saturated, heterocyclic ring each containing 1 to 4 heteroatoms selected from oxygen, nitrogen or sulfur;
Y is
(a) H,
(b) halogen,
(c) $C_{1-6}$ alkyl,
(d) $CF_3$,
(e) hydroxy,
(f) $C_{1-6}$ alkoxy, (g) $C_{1-4}$ alkenyl;
(h) phenyl;
(i) phenoxy,
(j) benzyloxy,
(k) benzoyl,
(l) $OCF_3$,
(m) CN,
(n) straight or branched $C_{1-6}$ hydroxyalkyl,
(o) straight or branched $C_{1-6}$ alkylhalides,
(p) $NH_2$,
(q) $NHR^6$,
(r) $NR^6R^7$,
(s) $NO_2$,
(t) $NHSO_2R^6$,
(u) $NR^6COR^7$, or
(v) —$CO_2R^6$;
$R^2$ and $R^4$ are independently:
(a) —$SO_2R^1$,
(b) H,
(c) $C_{1-6}$ alkyl,
(d) $C_1$–$C_3$ alkenyl,
(e) $C_1$–$C_3$ alkylaryl,
(f) Ar as defined above for $R^1$,
(g) —C(=O)$R^6$,
(h) —C(O)$NR^6R^7$,
(i) —C(S)$NR^6R^7$,
(j) —$CO_2R^6$;
(k) —C(S)$R^6$;
(l) straight or branched $C_{1-6}$ hydroxyalkyl, or
(m) straight or branched $C_{1-6}$ alkylhalides;
alternatively, $R^2$ and $R^4$ are linked to form a group $(CH_2)_2O$, $(CH_2)_4O$, or $(CH_2)_{3-5}$ in formula (I);
$R^5$ is selected from the group consisting of the following chemical groups:

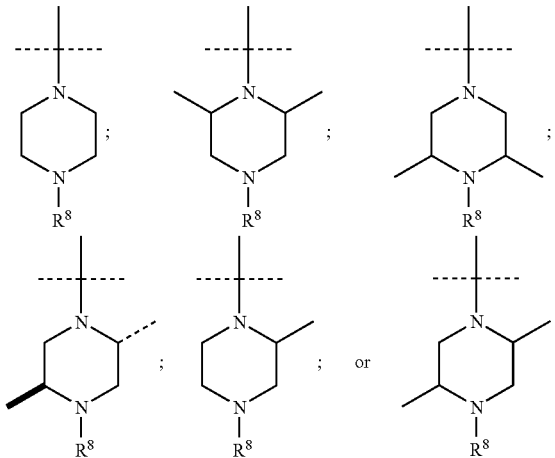

$R^6$ and $R^7$ are independently
(a) H,
(b) $C_{1-6}$ alkyl,
(c) $C_{3-7}$ cycloalkyl, or
(d) Ar, as defined above for $R^1$;
alternatively, $R^6$ and $R^7$ are linked to form a group $(CH_2)_2O$, $(CH_2)_4O$ or $(CH_2)_{3-5}$;
$R^8$ is
(a) H, or
(b) $C_{1-6}$ alkyl.

2. A compound according to claim 1 wherein $R^1$ is a group Ar;

Ar is
(a) phenyl,
(b) 1-naphthyl,
(c) 2-naphthyl, or
(f) a 5 to 7-membered, partially or completely saturated, heterocyclic ring containing 1 to 4 heteroatoms, selected from oxygen, nitrogen and sulfur;
the group Ar is substituted with Y, wherein Y is
(a) H,
(b) halogen,
(c) $C_{1-6}$ alkyl,
(d) $CF_3$,
(f) $C_{1-6}$ alkoxy,
(g) $C_{1-4}$ alkenyl;
(h) phenyl;
(l) $OCF_3$, or
(n) straight or branched $C_{1-6}$ hydroxyalkyl.

3. A compound according to claim 1, wherein the group

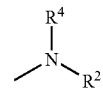

is attached to the phenyl ring in 2-position and 3-position.

4. A compound according to claim 1, wherein $R^2$ is —$SO_2R^1$.

5. A compound according to claim 1, wherein $R^3$ and $R^4$ are independently H, methyl or ethyl.

6. A compound according to claim 1, wherein $R^5$ is selected from the group consisting of the following chemical groups:

wherein $R^8$ is H or methyl.

7. A compound according to claim 1, wherein $R^6$ and $R^7$ are independently
(a) H,
(b) $C_{1-6}$ alkyl,
(c) $C_{3-7}$ cycloalkyl, or
(d) Ar.

8. A compound according to claim 1, wherein the compound is selected from the group consisting of:
N-[2-{ethyl[(3-fluorophenyl)sulfonyl]amino}-4-(4-methyl-1-piperazinyl)phenyl]-3-fluorobenzenesulfonamide,
N-[2-[ethyl(phenylsulfonyl)amino]-4-(4-methyl-1-piperazinyl)phenyl]benzenesulfonamide,
3-fluoro-N-[2-{[(3-fluorophenyl)sulfonyl]amino}-4-(4-methyl-1-piperazinyl) phenyl]benzenesulfonamide,
N-{5-(4-methyl-1-piperazinyl)-2-[(8-quinolinylsulfonyl)amino]phenyl}-7-quinolinesulfonamide,
N-[2-chloro-4-({4-(4-methyl-1-piperazinyl)-2-[(phenylsulfonyl)amino]anilino}sulfonyl)phenyl]acetamide, 3,4-dimethoxy-N-{4-(4-methyl-1-piperazinyl)-2-[(phenylsulfonyl)amino]phenyl}benzenesulfonamide,
3-methoxy-4-methyl-N-{4-(4-methyl-1-piperazinyl)-2-[(phenylsulfonyl)amino]phenyl}benzenesulfonamide,
4-methyl-N-{4-(4-methyl-1-piperazinyl)-2-[(methylsulfonyl)amino]phenyl}benzenesulfonamide,
3,4-dimethoxy-N-{4-(4-methyl-1-piperazinyl)-2-[(methylsulfonyl)amino]phenyl}benzenesulfonamide,
3-cyano-N-{4-(4-methyl-1-piperazinyl)-2-[(methylsulfonyl)amino]phenyl}benzenesulfonamide,
N-{4-(1-piperazinyl)-2-[(phenylsulfonyl)amino]phenyl}-1-naphthalenesulfonamide,
5-(dimethylamino)-N-{4-(1-piperazinyl)-2-[(phenylsulfonyl)amino]phenyl}-1-naphthalenesulfonamide,
N-[2-[(phenylsulfonyl)amino]-4-(1-piperazinyl)phenyl]-8-quinolinesulfonamide,
2,4,6-trimethyl-N-[2-[(phenylsulfonyl)amino]-4-(1-piperazinyl)phenyl]benzenesulfonamide,
4-methyl-N-[2-[(phenylsulfonyl)amino]-4-(1-piperazinyl)phenyl]benzenesulfonamide,
2,5-dimethoxy-N-[2-[(phenylsulfonyl)amino]-4-(1-piperazinyl)phenyl]benzenesulfonamide,
2-methyl-N-[2-[(phenylsulfonyl)amino]-4-(1-piperazinyl)phenyl]benzenesulfonamide,
2,4-difluoro-N-[2-[(phenylsulfonyl)amino]-4-(1-piperazinyl)phenyl]benzenesulfonamide,
4-butoxy-N-[2-[(phenylsulfonyl)amino]-4-(1-piperazinyl)phenyl]benzenesulfonamide,
3,5-dimethyl-N-[2-[(phenylsulfonyl)amino]-4-(1-piperazinyl)phenyl]-4-isoxazolesulfonamide,
5-fluoro-2-methyl-N-[2-[(phenylsulfonyl)amino]-4-(1-piperazinyl)phenyl]benzenesulfonamide,
4-(methylsulfonyl)-N-[2-[(phenylsulfonyl)amino]-4-(1-piperazinyl)phenyl]benzenesulfonamide,
2-(methylsulfonyl)-N-[2-[(phenylsulfonyl)amino]-4-(1-piperazinyl)phenyl]benzenesulfonamide,
2-methoxy-4-methyl-N-[2-[(phenylsulfonyl)amino]-4-(1-piperazinyl)phenyl]benzenesulfonamide,
4-methoxy-2-methyl-N-[2-[(phenylsulfonyl)amino]-4-(1-piperazinyl)phenyl]benzenesulfonamide,
N-[2-amino-4-(1-piperazinyl)phenyl]-3-fluorobenzenesulfonamide,
N-[2-(ethylamino)-4-(1-piperazinyl)phenyl]-3-fluorobenzenesulfonamide,
3-amino-N-(3-chlorophenyl)-4-(4-methyl-1-piperazinyl)benzenesulfonamide hydrochloride,
3-amino-N-(2-methoxyphenyl)-4-(4-methyl-1-piperazinyl)benzenesulfonamide hydrochloride,
3-amino-N-(2-methoxyphenyl)-4-(1-piperazinyl)benzenesulfonamide hydrochloride,
3-amino-N-phenyl-4-piperazin-1-yl-benzenesulfonamide hydrochloride,
3-amino-4-(4-ethyl-piperazin-1-yl)-N-phenyl-benzenesulfonamide hydrochloride,
3-amino-4-(trans-2,5-dimethylpiperazin-1-yl)-N-(2-methoxy-phenyl)benzenesulfonamide hydrochloride, and
3-amino-2-chloro-N-naphthalen-1-yl-4-piperazin-1-yl-benzenesulfonamide, hydrochloride.

9. A process for the preparation of a compound of claim 1 comprising:
(a) introduction of a cyclic diamine into a halogen and nitro substituted benzene under mild and basic conditions;
(b) reduction of the nitro to a corresponding amine;
(c) symmetric or asymmetric sulfonylation of the amine by a sulfonylchloride;
(d) introduction of groups $R^3$ and $R^4$ by alkylation reactions in basic conditions.

10. A pharmaceutical composition comprising a compound of claim 1 and a pharmaceutically acceptable diluent or carrier.

11. A method for the treatment of obesity, comprising administering to a mammal in need of such treatment an effective amount of a compound of claim 1.

12. A method for the reduction of food intake, the method comprising administering to a mammal in need of such treatment an effective amount of a compound of claim 1.

13. The method of claim 12, wherein the mammal in need of such treatment is an obese mammal.

14. A method for the treatment of a disorder of the central nervous system selected from anxiety, depression, panic attacks, memory disorders, sleep disorders, binge disorders, migraine, anorexia, bulimia, obsessive compulsive disorders, psychoses, Alzheimer's disease, Parkinson's disease, Huntington's chorea, schizophrenia, and/or Attention Deficit Hyperactive Disorder, the method comprising administering to a mammal in need of such treatment an effective amount of a compound of claim 1.

15. The method of claim 14, wherein the disorder is depression.

16. The method of claim 14, wherein the disorder is anxiety.

17. The method of claim 14, wherein the disorder is schizophrenia.

18. The method of claim 14, wherein the disorder is sleep disorders.

19. A compound of the formula (II)

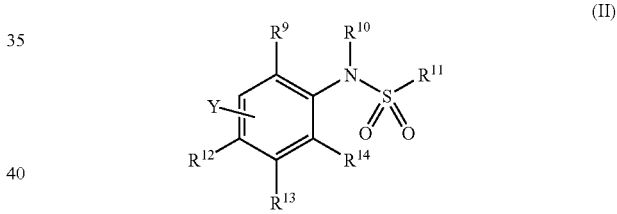

or a pharmaceutically acceptable salt thereof, wherein
$R^9$, $R^{12}$ and $R^{14}$ are H; or
two of $R^9$, $R^{12}$ and $R^{14}$ are H; and the remaining of $R^9$, $R^{12}$ and $R^{14}$ is
(a) —NH$_2$,
(b) —NHR$^6$,
(c) —NR$^6$R$^7$,
(d) —NH(CO)R$^6$,
(e) —NH(CS)R$^6$, or
(f) —NO$_2$;
$R^{10}$ is a group $R^3$;
$R^{11}$ is a group $R^1$;
in which each of $R^1$ and $R^3$, independently, is:
(a) H
(b) $C_{1-6}$ alkyl,
(c) $C_{1-6}$ alkoxy,
(d) straight or branched $C_{1-6}$ hydroxyalkyl,
(e) straight or branched $C_{1-6}$ alkylhalides; or
(f) a group Ar;
Ar is
(a) phenyl,
(b) 1-naphthyl,
(c) 2-naphthyl,
(d) benzyl, (e) cinnamoyl, (f) a 5 to 7-membered, partially or completely saturated, heterocyclic ring containing 1 to 4 heteroatoms, selected from oxygen, nitrogen and sulfur, or (g) a bicyclic ring system consisting of two heterocyclic rings as defined under (f), or a bicyclic ring system consisting of one benzene ring and one hetero cyclic ring as defined under (f);

alternatively, $R^1$ and $R^3$ are linked to form a group $(CH_2)_2O$, $(CH_2)_4O$, or $(CH_2)_{3-5}$; optionally, the group Ar is substituted with (a) Y, or (b) a 5 to 7-membered, partially or completely saturated, heterocyclic ring each containing 1 to 4 heteroatoms selected from oxygen, nitrogen or sulfur;

Y is

H;

$R^{13}$ is a group $R^5$; and is selected from the group consisting of the following chemical groups:

$R^6$ and $R^7$ are independently (a) H, (b) $C^{1-6}$ alkyl, (c) $C^{3-7}$ cycloalkyl, or (d) Ar, as defined above for $R^1$;

alternatively, $R^6$ and $R^7$ are linked to form a group $(CH_2)_2O$, $(CH_2)_4 O$ or $(CH_2)_{3-5}$;

$R^8$ is (a) H, or (b) $C_{1-6}$ alkyl.

20. A compound according to claim 19 wherein $R^{13}$ is a group $R^5$ selected from and $R^8$ is (a) H, or (b) $C_{1-6}$ alkyl;

with the proviso that only one of $R^9$, $R^{12}$ and $R^{14}$ is —$NH_2$, —$NHR^6$, —$NR^6R^7$, —$NH(CO)R^6$, —$NH(CS)R^6$, —$NO_2$; the other ones are H.

21. A compound according to claim 19, which is the compound N-[4-nitro-5-(piperazinyl)phenyl]benzenesulfonamide, or N-[4-amino-5-(piperazinyl)phenyl]benzenesulfonamide.

22. A process for the preparation of a compound of claim 19 comprising:

(a) introduction of a cyclic diamine into a halogen and nitro substituted benzene under mild and basic conditions;

(b) reduction of the nitro to a corresponding amine;

(c) selective introduction of a sulfonylamide group by a sulphonylchloride reacting with the amine;

(d) introduction of a sulfonylanimo group by an aromatic nucleophilic substitution reaction.

23. A pharmaceutical composition comprising a compound of claim 19 and a pharmaceutically acceptable diluent or carrier.

24. A method for the treatment of a disorder of the central nervous system selected from anxiety, depression, panic attacks, memory disorders, sleep disorders, binge disorders, migraine, anorexia, bulimia, obsessive compulsive disorders, psychoses, Alzheimer's disease, Parkinson's disease, Huntington's chorea, schizophrenia, and/or Attention Deficit Hyperactive Disorder, the method comprising administering to a mammal in need of such treatment an effective amount of a compound of claim 19.

25. The method of claim 24, wherein the disorder is depression.

26. The method of claim 24, wherein the disorder is anxiety.

27. The method of claim 24, wherein the disorder is schizophrenia.

28. The method of claim 24, wherein the disorder is sleep disorders.

29. The compound of claim 20, wherein $R^8$ is H or methyl.

30. A compound that is N-[2-({[(E)-2-phenylethenyl]sulfonyl}amino)-5 -(1-piperazinyl)phenyl]benzenesulfonamide.

31. A compound that is 3-amino-N-(2-methoxyphenyl)-4-(3-methyl-1-piperazinyl)benzenesulfonamide hydrochloride.

* * * * *

UNITED STATES PATENT AND TRADEMARK OFFICE
CERTIFICATE OF CORRECTION

PATENT NO. : 7,173,035 B2
APPLICATION NO. : 10/143335
DATED : February 6, 2007
INVENTOR(S) : Bremberg et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 396 days Delete the phrase "by 396 days" and insert -- by 461 days--

Signed and Sealed this

Twenty-fourth Day of July, 2007

JON W. DUDAS
*Director of the United States Patent and Trademark Office*